United States Patent
Sato et al.

(10) Patent No.: US 7,960,416 B2
(45) Date of Patent: Jun. 14, 2011

(54) STABLE EMULSION COMPOSITION

(75) Inventors: Jun Sato, Kawanishi (JP); Hikaru Taira, Ikeda (JP); Eiji Nara, Kawanishi (JP); Harold Jack Stevens, Garner, NC (US)

(73) Assignee: Takeda Pharmaceutical Company Limited, Osaka (JP)

( * ) Notice: Subject to any disclaimer, the term of this patent is extended or adjusted under 35 U.S.C. 154(b) by 1398 days.

(21) Appl. No.: 10/485,637

(22) PCT Filed: Aug. 3, 2001

(86) PCT No.: PCT/US01/24487
§ 371 (c)(1),
(2), (4) Date: Aug. 5, 2004

(87) PCT Pub. No.: WO03/013513
PCT Pub. Date: Feb. 20, 2003

(65) Prior Publication Data
US 2004/0253276 A1    Dec. 16, 2004

(51) Int. Cl.
*A61K 31/41* (2006.01)
*A61K 31/18* (2006.01)
(52) U.S. Cl. .......... 514/359; 514/383; 514/602
(58) Field of Classification Search .......... 514/359, 514/383, 602
See application file for complete search history.

(56) References Cited

U.S. PATENT DOCUMENTS

| | | | |
|---|---|---|---|
| 5,576,016 A | 11/1996 | Amselem et al. | 424/450 |
| 5,635,491 A | 6/1997 | Seki et al. | 514/53 |
| 5,814,324 A | 9/1998 | Sato et al. | 424/405 |
| 6,495,604 B1 * | 12/2002 | Ichimori et al. | 514/602 |
| 2003/0212114 A1 | 11/2003 | Sato et al. | 514/357 |

FOREIGN PATENT DOCUMENTS
WO    WO99/46242    *    9/1999

OTHER PUBLICATIONS

Supplementary European Search Report dated Aug. 31, 2009, in corresponding EP 01965853.3, 3 pages.
Washington, C., "Stability of lipid emulsions for drug delivery," Advanced Drug Delivery Reviews, 1996, 20:131-145.

* cited by examiner

*Primary Examiner* — San-ming Hui
(74) *Attorney, Agent, or Firm* — Foley & Lardner LLP

(57) ABSTRACT

An emulsion composition comprising (1) a compound (I) represented by the formula (I) wherein each symbol is as defined in the specification (2) an anionic synthetic phospholipid in a proportion of about 0.0001 about 5% (W/V) relative to the composition in total, and (3) a naturally-occurring phospholipid in a proportion of about 0.1 about 10% (W/V) relative to the composition in total is provided.

(I)

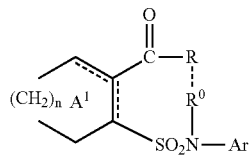

36 Claims, No Drawings

STABLE EMULSION COMPOSITION

TECHNICAL FIELD

The present invention relates to an emulsion composition having improved stability.

BACKGROUND

WO 99/46242 describes that a compound represented by the formula:

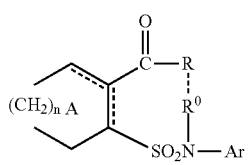

(Iaa)

wherein R represents an aliphatic hydrocarbon group optionally having substituents, an aromatic hydrocarbon group optionally having substituents, a heterocyclic group optionally having substituents, a group represented by the formula: $OR^1$ (wherein $R^1$ represents a hydrogen atom or an aliphatic hydrocarbon group optionally having substituents) or a group represented by the formula:

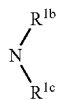

(wherein $R^{1b}$ represents a hydrogen atom or an aliphatic hydrocarbon group optionally having substituents, $R^{1c}$ is, same with or different from $R^{1b}$, a hydrogen atom or an aliphatic hydrocarbon group optionally having substituents, $R^0$ represents a hydrogen atom or an aliphatic hydrocarbon group, or R and $R^0$ represent a bond with each other, ring A is a cycloalkene substituted by 1 to 4 selected from (i) an aliphatic hydrocarbon group optionally having substituents, (ii) an aromatic hydrocarbon group optionally having substituents, (iii) a group represented by the formula: $OR^1$ (wherein $R^1$ represents the same meaning as mentioned above) and (iv) a halogen atom, Ar represents an aromatic hydrocarbon group optionally having substituents, a group represented by the formula:

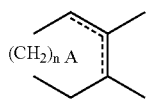

which can be a group represented by the formula:

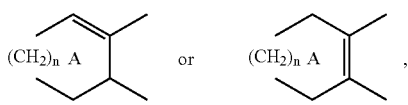

and n is an integer of 1 to 4, and a compound represented by the formula:

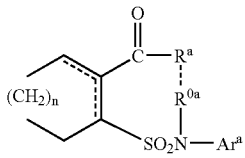

(Ie)

wherein $R^a$ represents an aliphatic hydrocarbon group optionally having substituents, an aromatic hydrocarbon group optionally having substituents, a heterocyclic group optionally having substituents, a group represented by the formula: $OR^{1a}$ (wherein $R^{1a}$ represents a hydrogen atom or an aliphatic hydrocarbon group optionally having substituents) or a group represented by the formula:

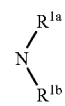

(wherein $R^{1a}$ represents the same meaning as defined above, $R^{1b}$ is, same with or different from $R^{1a}$, a hydrogen atom or an aliphatic hydrocarbon group optionally having substituents, $R^{0a}$ represents a hydrogen atom or an aliphatic hydrocarbon group, or $R^a$ and $R^{0a}$ represent a bond with each other, $Ar^a$ represents an aromatic hydrocarbon group optionally having substituents, a group represented by the formula:

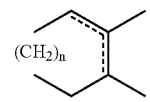

which can be a group represented by the formula:

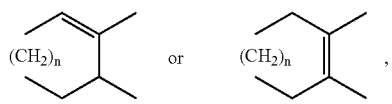

n represents an integer of 1 to 4, a salt thereof and a prodrug thereof have nitric oxide (NO) production-inhibiting effect and an inhibitory effect on the production of inflammatory cytokines such as TNF-α, IL-1, IL-6 and the like, and are useful as a prophylactic and therapeutic agent against the diseases including cardiac diseases, autoimmune diseases, inflammatory diseases, central nervous system diseases, infectious diseases, sepsis, septic shock and the like.

This publication also describes that an oily injection can be produced by dissolving, suspending or emulsifying this compound in a vegetable oil or propylene glycol.

The present invention aims at providing an emulsion composition, which contains the above compound, having improved stability.

DETAILED DESCRIPTION OF THE INVENTION

The above-mentioned aim has been accomplished by the present invention. The pH of the emulsion composition containing the above-mentioned compound is adjusted to not more than about 6, whereby the stability of the compound, the composition and the system has been improved and superior efficacy has been provided as described in further detail below. The present invention is based on this finding.

Accordingly, the present invention provides the following.

[1] An emulsion composition comprising (1) a compound (I) represented by the formula:

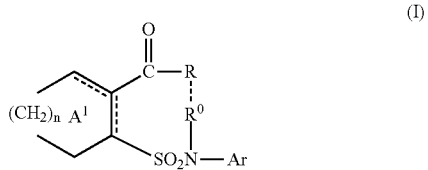

(I)

wherein R represents an aliphatic hydrocarbon group optionally having substituents, an aromatic hydrocarbon group optionally having substituents, a heterocyclic group optionally having substituents, a group represented by the formula: $OR^1$ (wherein $R^1$ represents a hydrogen atom or an aliphatic hydrocarbon group optionally having substituents) or a group represented by the formula:

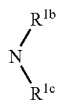

(wherein $R^{1b}$ represents a hydrogen atom or an aliphatic hydrocarbon group optionally having substitutents, $R^{1c}$ is, same with or different from $R^{1b}$, a hydrogen atom or an aliphatic hydrocarbon group optionally having substituents, $R^0$ represents a hydrogen atom or an aliphatic hydrocarbon group, or R and $R^0$ represent a bond with each other, ring $A^1$ is a cycloalkene optionally substituted by 1 to 4 selected from (i) an aliphatic hydrocarbon group optionally having substituents, (ii) an aromatic hydrocarbon group optionally having substituents, (iii) a group represented by the formula: $OR^1$ (wherein $R^1$ represents the same meaning as mentioned above) and (iv) a halogen atom, Ar represents an aromatic hydrocarbon group optionally having substituents, a group represented by the formula:

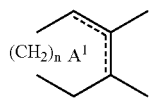

can be a group represented by the formula:

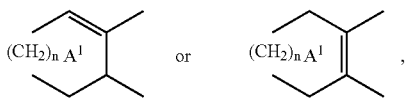

and n is an integer of 1 to 4, a salt thereof or a prodrug therefor,
(2) an anionic synthetic phospholipid in a proportion of about 0.0001-about 5% (W/V) relative to the entire composition, and
(3) a naturally-occurring phospholipid in a proportion of about 0.1-about 10% (W/V) relative to the entire composition,

[2] the composition of [1], wherein R is (1) ① linear or branched $C_{1-20}$ alkyl, ② $C_{3-10}$ cycloalkyl, ③ $C_{4-12}$ cycloalkylalkyl, ④ lower ($C_{3-6}$) alkenyl group or ⑤ lower ($C_{3-6}$) alkynyl group (wherein the substituent selected from substituent group A may form, together with ① linear or branched ($C_{1-20}$) alkyl, ② $C_{3-10}$ cycloalkyl, ③ $C_{4-12}$ cycloalkylalkyl, ⑤ lower ($C_{3-6}$) alkenyl group or ⑤ lower ($C_{3-6}$) alkynyl group, indanyl group or 1,2,3,4-tetrahydronaphthyl group optionally having 1 to 4 substituents selected from the substituent group A), optionally having 1 to 4 substituents selected from a group (hereinafter substituent group A) consisting of (i) a 5- to 8-membered ring group or a condensed ring group containing 1 to 4 hetero atoms selected from nitrogen atom (optionally oxidized), oxygen atom and sulfur atom, which is optionally substituted by 1 to 3 substituent(s) selected from $C_{1-4}$ alkyl, hydroxy, oxo and $C_{1-4}$ alkoxy, (ii) oxo group, (iii) hydroxyl group, (iv) $C_{1-6}$ alkoxy group, (v) $C_{3-10}$ cycloalkyloxy group, (vi) $C_{6-10}$ aryloxy group, (vii) $C_{7-19}$ aralkyloxy group, (viii) a 5- to 8-membered ring group or a condensed ring-oxy group containing 1 to 4 hetero atoms selected from nitrogen atom (optionally oxidized), oxygen atom and sulfur atom, which is optionally substituted by 1 to 3 substituent(s) selected from $C_{1-4}$ alkyl, hydroxy, oxo and $C_{1-4}$ alkoxy, (ix) $C_{1-6}$ alkylthio group (the sulfur atom may be oxidized), (x) $C_{3-10}$ cycloalkylthio group (the sulfur atom may be oxidized), (xi) $C_{6-10}$ arylthio group (the sulfur atom may be oxidized), (xii) $C_{7-19}$ aralkylthio group (the sulfur atom may be oxidized), (xiii) a 5- to 8-membered ring group or a condensed ring-thio group containing 1 to 4 hetero atoms selected from nitrogen atom (optionally oxidized), oxygen atom and sulfur atom, which is optionally substituted by 1 to 3 substituent(s) selected from $C_{1-4}$ alkyl, hydroxy, oxo and $C_{1-4}$ alkoxy, (xiv) a 5- to 8-membered ring group or a condensed ring-sulfinyl group containing 1 to 4 hetero atoms selected from nitrogen atom (optionally oxidized), oxygen atom and sulfur atom, which is optionally substituted by 1 to 3 substituent(s) selected from $C_{1-4}$ alkyl, hydroxy, oxo and $C_{1-4}$ alkoxy, (xv) a 5- to 8-membered ring group or a condensed ring-sulfonyl group containing 1 to 4 hetero atoms selected from nitrogen atom (optionally oxidized), oxygen atom and sulfur atom, which is optionally substituted by 1 to 3 substituent(s) selected from $C_{1-4}$ alkyl, hydroxy, oxo and $C_{1-4}$ alkoxy, (xvi) nitro group, (xvii) halogen atom, (xviii) cyano group, (xix) carboxyl group, (xx) $C_{1-10}$ alkoxy-carbonyl group, (xxi) $C_{3-6}$ cycloalkyloxy-carbonyl group, (xxii) $C_{6-10}$ aryloxy-carbonyl group, (xxiii) $C_{7-19}$ aralkyloxy-carbonyl group, (xxiv) a 5- to 8-membered ring group or a condensed ring-oxycarbonyl group containing 1 to 4 hetero atoms selected from nitrogen atom (optionally oxidized), oxygen atom and sulfur atom, which is optionally substituted by 1 to 3 substituent(s) selected from $C_{1-4}$ alkyl, hydroxy, oxo and $C_{1-4}$ alkoxy, (xxv) $C_{6-10}$ arylcarbonyl group, (xxvi) $C_{1-6}$ alkanoyl group, (xxvii) $C_{3-5}$ alkenoyl group, (xxviii) $C_{6-10}$ aryl-carbonyloxy group, (xxix) $C_{2-6}$ alkanoyloxy group, (xxx) $C_{3-5}$ alkenoyloxy group, (xxxi) carbamoyl group or cyclic aminocarbonyl group optionally substituted by 1 or 2 substituent(s) selected from $C_{1-4}$ alkyl, phenyl, $C_{1-7}$ acyl and $C_{1-4}$ alkoxy-phenyl, (xxxii) thiocarbamoyl group optionally substituted by 1 or 2 substituent(s) selected from $C_{1-4}$ alkyl and phenyl, (xxxiii) carbamoyloxy group optionally substituted by 1 or 2 substituent(s) selected from $C_{1-4}$ alkyl and phenyl, (xxxiv) $C_{1-6}$ alkanoylamino group, (xxxv) $C_{6-10}$ arylcarbonylamino group, (xxxvi) $C_{1-10}$ alkoxy-carboxamide group, (xxxvii) $C_{6-10}$ aryloxy-carboxamide group, (xxxviii) $C_{7-19}$ aralkyloxy-carboxamide group, (xxxix) $C_{1-10}$ alkoxy-carbonyloxy group, (xxxx) $C_{6-10}$ aryloxy-carbonyloxy group, (xxxxi) $C_{7-19}$ aralkyloxy-carbonyloxy group, (xxxxii) $C_{3-10}$ cycloalkyloxy-carbonyloxy group, (xxxxiii) ureido group optionally substituted by 1 to 3 substituent(s) selected from $C_{1-4}$ alkyl group and phenyl group, and (xxxxiv) $C_{6-10}$ aryl group optionally having 1 to 4 substituents selected from a group consisting of the above-mentioned (i)-(xxxxiii), (2) $C_{6-14}$ aromatic hydrocarbon group optionally having 1 to 5 substituents selected from the group consisting of halogen atom, $C_{1-4}$ alkyl group, $C_{1-4}$ alkoxy group, $C_{1-4}$ alkoxy-carbonyl group, carboxyl group, nitro group, cyano group, hydroxyl group, $C_{1-4}$ alkanoylamino group, $C_{3-16}$ cycloalkyl group, $C_{6-10}$ aryl group, halogeno $C_{1-4}$ alkyl group, halogeno $C_{1-4}$ alkoxy group, $C_{1-4}$ alkylthio group, $C_{1-4}$ alkylsulfonyl group, $C_{1-4}$ alkanoyl group, 5-membered aromatic heterocyclic group, carbamoyl group, $C_{1-4}$ alkyl-carbamoyl group, $C_{1-4}$ alkoxy-carbonyl-$C_{1-4}$ alkyl-carbamoyl group and 1,3-diacylguanidino-$C_{1-4}$ alkyl group, (3) a 5- to 8-membered ring group or a condensed ring group containing 1 to 4 hetero atom selected from nitrogen atom (optionally oxidized), oxygen atom and sulfur atom, which optionally has 1 to 3 substituents selected from $C_{1-4}$ alkyl, hydroxy, oxo and $C_{1-4}$ alkoxy, (4) a group of the formula —$OR^1$ (wherein $R^1$ is (i) hydrogen atom or (ii) ① linear or branched $C_{1-20}$ alkyl, ② $C_{3-10}$ cycloalkyl, ③ $C_{4-12}$ cycloalkylalkyl, ④ lower ($C_{3-6}$) alkenyl group or ⑤ lower ($C_{3-6}$) alkynyl group (wherein the substituent selected from substituent group A may form, together with ① linear or branched $C_{1-20}$ alkyl, ② $C_{3-10}$ cycloalkyl, ③ $C_{4-12}$ cycloalkylalkyl, ④ lower ($C_{3-6}$) alkenyl group or ⑤ lower ($C_{3-6}$) alkynyl group, indanyl group or 1,2,3,4-tetrahydronaphthyl group optionally having 1 to 4 substituents selected from the substituent group A), which optionally has 1 to 4 substituents selected from the substituent group A), or (5) a group of the formula

(wherein $R^{1b}$ is (i) hydrogen atom or (ii) ① linear or branched $C_{1-20}$ alkyl, ② $C_{3-10}$ cycloalkyl, ③ $C_{4-12}$ cycloalkylalkyl, ④ lower ($C_{3-6}$) alkenyl group or ⑤ lower ($C_{3-6}$) alkynyl group (wherein the substituent selected from substituent group A may form, together with ① linear or branched $C_{1-20}$ alkyl, ② $C_{3-10}$ cycloalkyl, ③ $C_{4-12}$ cycloalkylalkyl, ④ lower ($C_{3-6}$) alkenyl group or ⑤ lower ($C_{3-6}$) alkynyl group, indanyl group or 1,2,3,4-tetrahydronaphthyl group optionally having 1 to 4 substituents selected from the substituent group A), which optionally has 1 to 4 substituents selected from the substituent group A), and $R^{1c}$ is the same or different from $R^{1b}$ and is (i) hydrogen atom or (ii) ① linear or branched $C_{1-20}$ alkyl, ② $C_{3-10}$ cycloalkyl, ③ $C_{4-12}$ cycloalkylalkyl, ④ lower ($C_{3-6}$) alkenyl group or ⑤ aliphatic hydrocarbon group optionally having a substituent of lower ($C_{3-6}$) alkynyl group (wherein the substituent selected from substituent group A may form, together with ① linear or branched $C_{1-20}$ alkyl, ② $C_{3-10}$ cycloalkyl, ③ $C_{4-12}$ cycloalkylalkyl, ④ lower ($C_{3-6}$) alkenyl group or ⑤ lower ($C_{3-6}$) alkynyl group, indanyl group or 1,2,3,4-tetrahydronaphthyl group optionally having 1 to 4 substituents selected from the substituent group A) optionally having 1 to 4 substituents selected from substituent group A), $R^0$ represents a hydrogen atom, a linear or branched $C_{1-20}$ alkyl, a $C_{3-10}$ cycloalkyl, a $C_{4-12}$ cycloalkylalkyl, a lower ($C_{3-6}$) alkenyl group or a lower ($C_{3-6}$) alkynyl group, or R and $R^0$ represent a bond with each other, ring $A^1$ represents (1) ① linear or branched $C_{1-20}$ alkyl, ② $C_{3-10}$ cycloalkyl, $C_{4-12}$ cycloalkylalkyl, ④ lower ($C_{3-6}$) alkenyl group or ⑤ lower ($C_{3-6}$) alkynyl group, which optionally has 1 to 4 substituents selected from substituent group A (wherein the substituents selected from the substituent group A may form, together with ① linear or branched $C_{1-20}$ alkyl, ② $C_{3-10}$ cycloalkyl, ③ $C_{4-12}$ cycloalkylalkyl, ④ lower ($C_{3-6}$) alkenyl group or ⑤ lower ($C_{3-6}$) alkynyl group, indanyl group or 1,2,3,4-tetrahydronaphthyl group optionally having 1 to 4 substituents selected from the substituent group A), (2) a $C_{6-14}$ aromatic hydrocarbon group optionally having 1 to 5 substituents selected from the group consisting of halogen atom, $C_{1-4}$ alkyl group, $C_{1-4}$ alkoxy group, $C_{1-4}$ alkoxy-carbonyl group, carboxyl group, nitro group, cyano group, hydroxyl group, $C_{1-4}$ alkanoylamino group, $C_{3-6}$ cycloalkyl group, $C_{6-10}$ aryl group, halogeno $C_{1-4}$ alkyl group, halogeno $C_{1-4}$ alkoxy group, $C_{1-4}$ alkylthio group, $C_{1-4}$ alkylsulfonyl group, $C_{1-4}$ alkanoyl group, 5-membered aromatic heterocyclic group, carbamoyl group, $C_{1-4}$ alkyl-carbamoyl group, $C_{1-4}$ alkoxy-carbonyl-$C_{1-4}$ alkyl-carbamoyl group and 1,3-diacylguanidino-$C_{1-4}$ alkyl group, (3) a group of the formula —$OR^1$ (wherein $R^1$ is as defined above) or (4) cycloalkene optionally substituted by 1 to 4 selected from halogen atoms, and Ar represents a $C_{6-14}$ aromatic hydrocarbon group optionally having 1 to 5 substituents selected from the group consisting of halogen atom, $C_{1-4}$ alkyl group, $C_{1-4}$ alkoxy group, $C_{1-4}$ alkoxycarbonyl group, carboxyl group, nitro group, cyano group, hydroxyl group, $C_{1-4}$ alkanoylamino group, $C_{3-6}$ cycloalkyl group, $C_{6-10}$ aryl group, halogeno $C_{1-4}$ alkyl group, halogeno $C_{1-4}$ alkoxy group, $C_{1-4}$ alkylthio group, $C_{1-4}$ alkylsulfonyl group, $C_{1-4}$ alkanoyl group, 5-membered aromatic heterocyclic group, carbamoyl group, $C_{1-4}$ alkyl-carbamoyl group, $C_{1-4}$ alkoxy-carbonyl-$C_{1-4}$ alkyl-carbamoyl group and 1,3-diacylguanidino-$C_{1-4}$ alkyl group,

[3] the composition of [1], wherein the compound is selected from the group consisting of ① d-ethyl 6-[N-(2-chloro-4-fluorophenyl)sulfamoyl]-1-cyclohexene-1-carboxylate, ② d-ethyl 6-[N-(2,4-difluorophenyl)sulfamoyl]-1-cyclohexene-1-carboxylate, ③ ethyl 6-[N-(2-chlorophenyl)sulfamoyl]-1-cyclohexene-1-carboxylate and ④ ethyl 6-[N-(2-chloro-4-methylphenyl)sulfamoyl]-1-cyclohexene-1-carboxylate, or a salt thereof,

[4] the composition of [1], wherein the anionic synthetic phospholipid is a compound of the formula

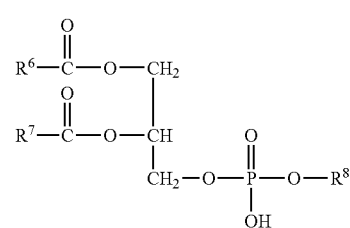

(II)

wherein $R^6$ and $R^7$ are the same or different and each is $C_{7-20}$ chain hydrocarbon group, and $R^8$ is

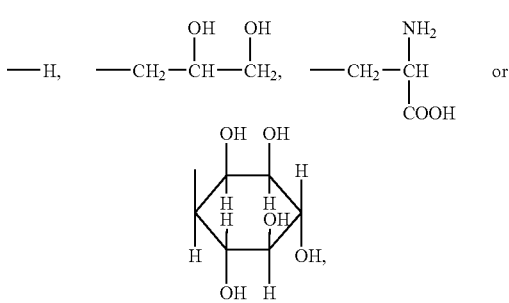

or a salt thereof,

[5] the composition of [1], wherein the anionic synthetic phospholipid is a compound of the formula

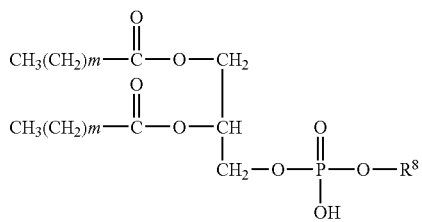

wherein m is an integer of 7-20, and $R^8$ is

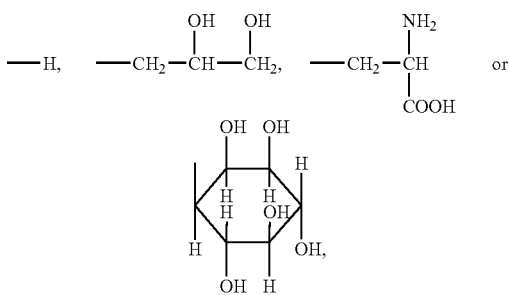

or a salt thereof,

[6] the composition of [1], wherein the anionic synthetic phospholipid is selected from the group consisting of dimyristoylphoshpatidylglycerol, dipalmitoylphosphatidylglycerol, distearoylphosphatidylglycerol, dioleoylphosphatidylglycerol, oleoylpalmitoylphosphatidylglycerol, dioctanoylphosphatidic acid, didecanoylphosphatidic acid, dilauroylphosphatidic acid, dimyristoylphosphatidic acid, dipalmitoylphosphatidic acid, diheptadecanoylphosphatidic acid, distearoylphosphatidic acid, dioleoylphosphatidic acid, arachidonylstearoylphosphatidic acid, dipalmitoylphosphatidylserine, dioleoylphosphatidylserine, dimyristoylphosphatidylinositol, dipalmitoylphosphatidylinositol, distearoylphosphatidylinositol, dioleoylphosphatidylinositol, dimyristoylphosphatidylserine and distearoylphosphatidylserine,

[7] the composition of [1], wherein the anionic synthetic phospholipid is dimyristoylphosphatidylglycerol,

[8] the composition of [1], wherein the naturally-occurring phospholipid is egg yolk lecithin or soybean lecithin,

[9] the composition of [1], wherein the naturally-occurring phospholipid is egg yolk lecithin,

[10] the composition of [1], wherein the anionic synthetic phospholipid is contained in a proportion of about 0.0001-about 2% (W/V) of the composition in total,

[11] the composition of [1], wherein the anionic synthetic phospholipid is contained in a proportion of about 0.2% (W/V) of the composition in total,

[12] the composition of [1], which comprises the compound (I), a salt thereof or a prodrug therefor in a proportion of about 0.001-about 95 wt % of the composition in total,

[13] the composition of [1], which comprises the compound (I), a salt thereof or a prodrug therefor in a proportion of about 0.01-about 30 wt % of the composition in total,

[14] the composition of [1], which comprises an oil component and/or water,

[15] the composition of [14], wherein the oil component is selected from the group consisting of vegetable oil, a partially hydrogenated vegetable oil, mono-acid glyceride, mixed acid glyceride and medium-size chain fatty acid glycerine ester,

[16] the composition of [14], wherein the oil component is a vegetable oil,

[17] the composition of [16], wherein the vegetable oil is selected from the group consisting of soybean oil, cottonseed oil, rapeseed oil, peanut oil, safflower oil, sesame oil, rice bran oil, corn germ oil, sunflower oil, poppy oil and olive oil,

[18] the composition of [16], wherein the vegetable oil is a soybean oil,

[19] the composition of [14], wherein the oil component is contained in a proportion of about 1-about 30 wt % of the composition in total,

[20] the composition of [14], wherein the phospholipid is contained in a proportion of about 0.1-about 150 wt % of the oil component,

[21] the composition of [1], which comprises glycerine,

[22] the composition of [1], which is an oil-in-water composition,

[23] the composition of [1], which has a pH adjusted to about 3-about 6,

[24] the composition of [1], which is for an injection, [25] the composition of [1], which is an injectable composition comprising 1% of d-ethyl 6-[N-(2-chloro-4-fluorophenyl)sulfamoyl]-1-cyclohexene-1-carboxylate, 20% of soybean oil, 1.2% of egg yolk lecithin, 0.2% (W/V) of dimyristoylphosphatidylglycerol and water, relative to the composition in total,

[26] the composition of [1], which is an injectable composition comprising 1% of d-ethyl 6-[N-(2-chloro-4-fluorophenyl)sulfamoyl]-1-cyclohexene-1-carboxylate, 20% of soybean oil, 1.2% of egg yolk lecithin, 0.2% (W/V) of distearoylphosphatidylglycerol and water, relative to the composition in total,

[27] the composition of [1], which comprises a disperse phase particle comprising anionic synthetic phospholipid, naturally-occurring phospholipid, an oil component and compound (I), a salt thereof or a prodrug therefor, and water wherein the disperse phase particle is dispersed,

[28] the composition of [27], wherein the disperse phase has an average particle size of about 25-about 500 nm,

[29] the composition of [1], which is an NO and/or cytokine production inhibitor,

[30] the composition of [1], which is an agent for preventing or treating cardiac disease, autoimmune disease, sepsis or septic shock,

[31] a method for stabilizing an emulsion composition comprising
(1) a compound represented by the formula:

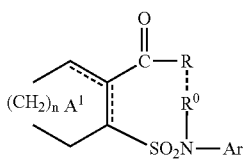
(I)

wherein R represents an aliphatic hydrocarbon group optionally having substituents, an aromatic hydrocarbon group optionally having substituents, a heterocyclic group optionally having substituents, a group represented by the formula: $OR^1$ (wherein $R^1$ represents a hydrogen atom or an aliphatic hydrocarbon group optionally having substituents) or a group represented by the formula:

(wherein $R^{1b}$ represents a hydrogen atom or an aliphatic hydrocarbon group optionally having substituents, $R^{1c}$ is, same with or different from $R^{1b}$, a hydrogen atom or an aliphatic hydrocarbon group optionally having substituents, $R^0$ represents a hydrogen atom or an aliphatic hydrocarbon group, or R and $R^0$ represent a bond with each other, ring $A^1$ is a cycloalkene optionally substituted by 1 to 4 selected from (i) an aliphatic hydrocarbon group optionally having substituents, (ii) an aromatic hydrocarbon group optionally having substituents, (iii) a group represented by the formula: $OR^1$ (wherein $R^1$ represents the same meaning as mentioned above) and (iv) a halogen atom, Ar represents an aromatic hydrocarbon group optionally having substituents, a group represented by the formula:

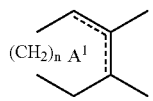

can be a group represented by the formula:

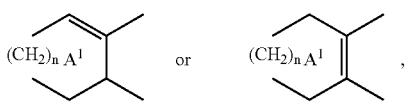

and n is an integer of 1 to 4, a salt thereof or a prodrug therefor,
(2) an anionic synthetic phospholipid in a proportion of about 0.0001-about 5% (W/V) relative to the composition in total, and
(3) a naturally-occurring phospholipid in a proportion of about 0.1-about 10% (W/V) relative to the composition in total,
wherein said composition is adjusted to have a pH of not more than 6,
[32] the stabilizing method of [31], wherein the stability during autoclave sterilization is improved,
[33] a method for preventing or treating cardiac disease, autoimmune disease, sepsis or septick shock, which comprises administrating to a mammal an effective amount of the composition of [1], and
[34] use of the composition of [1] for manufacturing an agent for preventing or treating cardiac disease, autoimmune disease, sepsis or septick shock.

The present invention also provides
[35] the composition of [1], wherein the compound of the formula (I) is a compound represented by the formula:

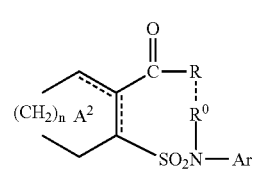
(Iaa)

wherein R represents an aliphatic hydrocarbon group optionally having substituents, an aromatic hydrocarbon group optionally having substituents, a heterocyclic group optionally having substituents, a group represented by the formula: $OR^1$ (wherein $R^1$ represents a hydrogen atom or an aliphatic hydrocarbon group optionally having substituents) or a group represented by the formula:

(wherein $R^{1b}$ represents a hydrogen atom or an aliphatic hydrocarbon group optionally having substituents, $R^{1c}$ is, same with or different from $R^{1b}$, a hydrogen atom or an aliphatic hydrocarbon group optionally having substituents), $R^0$ represents a hydrogen atom or an aliphatic hydrocarbon group, or R and $R^0$ represent a bond with each other, ring $A^2$ is a cycloalkene substituted by 1 to 4 substituents selected from (i) an aliphatic hydrocarbon group optionally having substituents, (ii) an aromatic hydrocarbon group optionally having substituents, (iii) a group represented by the formula: $OR^1$ (wherein $R^1$ represents the same meaning as mentioned above) and (iv) a halogen atom, Ar represents an aromatic hydrocarbon group optionally having substituents, a group represented by the formula:

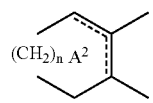

can be a group represented by the formula:

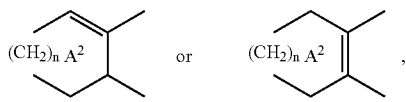

and n is an integer of 1 to 4, or a compound represented by the formula:

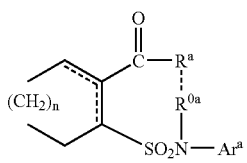
(Ie)

wherein $R^a$ represents an aliphatic hydrocarbon group optionally having substituents, an aromatic hydrocarbon group optionally having substituents, a heterocyclic group optionally having substituents, a group represented by the formula: $OR^{1a}$ (wherein $R^{1a}$ represents a hydrogen atom or an aliphatic hydrocarbon group optionally having substituents) or a group represented by the formula:

(wherein $R^a$ represents the same meaning as defined above, $R^1$ is, same with or different from $R^{1a}$, a hydrogen atom or an aliphatic hydrocarbon group optionally having substituents, $R^{1a}$ represents a hydrogen atom or an aliphatic hydrocarbon group, or $R^a$ and $R^{0a}$ represent a bond with each other, $Ar^a$ represents an aromatic hydrocarbon group optionally having substituents, a group represented by the formula:

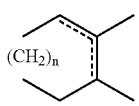

can be a group represented by the formula:

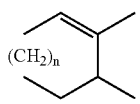 or 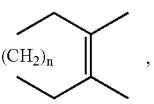, n represents an integer of 1 to 4,
[36] the composition of [35], wherein the compound represented by the formula (Iaa) is a compound represented by the formula:

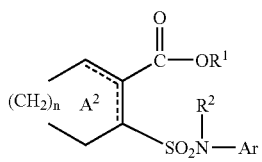
(Ibb)

wherein each symbols represents the same meaning as defined in [35],
[37] the composition of [35], wherein the ring $A^2$ is a cycloalkene substituted by lower alkyl, phenyl or halogen, $R^1$ is a lower alkyl group, Ar is a phenyl group optionally having substituents, and n is 2,
[38] the composition of [35], wherein the compound represented by the formula (Ie) is a compound of the formula:

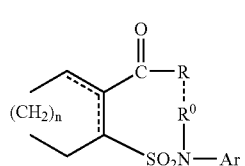
(Ia)

wherein R represents an aliphatic hydrocarbon group optionally having substituents, an aromatic hydrocarbon group optionally having substituents, a heterocyclic group optionally having substituents, a group represented by the formula: $OR^1$ (wherein $R^1$ represents a hydrogen atom or an aliphatic hydrocarbon group optionally having substituents) or a group represented by the formula:

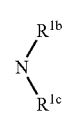

(wherein $R^{1b}$ represents a hydrogen atom or an aliphatic hydrocarbon group optionally having substituents, $R^{1c}$ is, same with or different from $R^{1b}$, a hydrogen atom or an aliphatic hydrocarbon group optionally having substituents), $R^0$ represents a hydrogen atom or an aliphatic hydrocarbon group, or R and $R^0$ represent a bond with each other, Ar represents an aromatic hydrocarbon group optionally having substituents, a group represented by the formula:

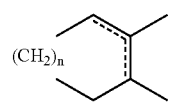

can be a group represented by the formula:

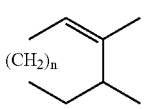 or 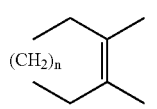, and n is an integer of 1 to 4, provided that when n is 1 or 2 and (i) $R^1$ is a hydrogen atom or an ethyl group, $R^0$ is a methyl group and Ar is a phenyl group or (ii) R and $R^0$ represent a bond with each other and Ar is a phenyl group, a 2-methylphenyl group, a 4-bromophenyl group, a 4-methoxyphenyl group or a 2,6-dimethylphenyl group, a group represented by the formula:

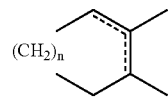

is a group represented by the formula:

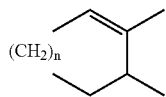

[39] the composition of [38], wherein the compound represented by the formula (Ia) is a compound represented by the formula:

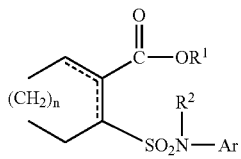
(Ib)

wherein $R^2$ represents a hydrogen atom or an aliphatic hydrocarbon group, $R^1$, Ar, n and the group represented by the formula:

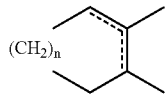

represent the same meanings defined in [38], provided that when n is 1 or 2, Ar is a phenyl group, $R^1$ is a hydrogen atom or an ethyl group and $R^2$ is a methyl group, the group represented by the formula:

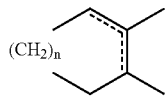

is a group represented by the formula:

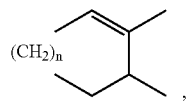,

[40] the composition of [39], wherein $R^1$ is a lower alkyl group optionally having substituents,

[41] the composition of [39], wherein $R^1$ is an ethyl group,

[42] the composition of [39], wherein $R^2$ is a hydrogen atom or a lower alkyl group,

[43] the composition of [39], wherein $R^2$ is a hydrogen atom,

[44] the composition of [39], wherein Ar is a phenyl group optionally having substituents,

[45] the composition of [39], wherein Ar is a phenyl group substituted by halogen or/and lower alkyl,

[46] the composition of [39], wherein Ar is a group represented by the formula:

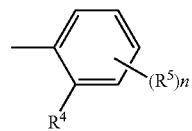

wherein $R^4$ and $R^5$ are same or different and represents a halogen atom or a lower alkyl group, and n is an integer of 0 to 2,

[47] the composition of [39], wherein the halogen atom is a fluoro atom or a chloro atom,

[48] the composition of [39], wherein the group represented by the formula:

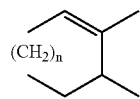

is a group represented by the formula:

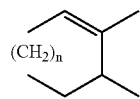

wherein n represents the same meaning as defined in [39],

[49] the composition of [39], wherein n is 1 to 3,

[50] the composition of [39], wherein $R^1$ is a lower alkyl group optionally having substituents, $R^2$ is a hydrogen atom or a lower alkyl group, Ar is a phenyl group optionally having substituents, n is 1, 2 or 3,

[51] the composition of [39], wherein $R^1$ is a lower alkyl group optionally having substituents, $R^2$ is a hydrogen atom, Ar is a phenyl group substituted by a halogen atom, and n is 2,

[52] the composition of [38], wherein the compound represented by the formula (Ia) is a compound represented by the formula:

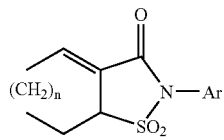
(Ic)

wherein Ar and n represent the same meanings as defined in [38],

[53] the composition of [52], wherein Ar is a phenyl group optionally having substituents, and n is 2,

[54] the composition of [38], wherein the compound represented by the formula (Ia) is a compound represented by the formula:

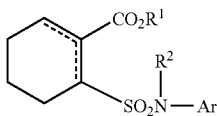 (Id)

wherein R$^1$, R$^2$ and Ar represent the same meanings as defined in [39], the group represented by the formula:

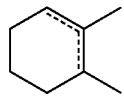

is a group represented by the formula:

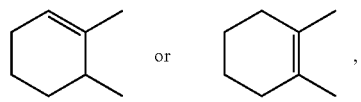

provided that when Ar is a phenyl group, R$^1$ is a hydrogen atom or an ethyl group and R$^2$ is a methyl group and the group represented by the formula:

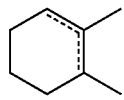

is a group represented by the formula:

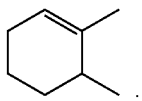.

[55] the composition of [35], wherein the compound represented by the formula (Ie) is a compound represented by the formula:

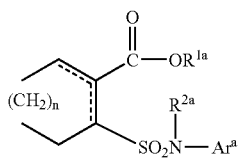 (If)

wherein R$^{2a}$ represents a hydrogen atom or an aliphatic hydrocarbon group, R$^{1a}$, Ar$^a$, n and the group represented by the formula:

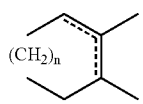

represent the same meanings as defined in [35], and [56] the composition of [35], wherein the compound represented by the formula (Ie) is a compound represented by the formula:

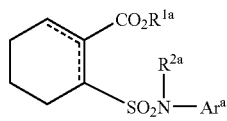 (Ig)

wherein R$^{1a}$, R$^{2a}$ and Ar$^a$ represent the same meanings as defined in [55] and the group represented by the formula:

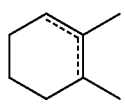

is a group represented by the formula:

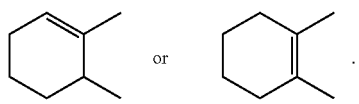.

In the specification, R represents an aliphatic hydrocarbon group optionally having substituents, an aromatic hydrocarbon group optionally having substituents, a heterocyclic group optionally having substituents, a group represented by the formula: OR$^1$ (wherein R$^1$ represents a hydrogen atom or an aliphatic hydrocarbon group optionally having substituents) or a group represented by the formula:

wherein R$^{1b}$ represents a hydrogen atom or an aliphatic hydrocarbon group optionally having substituents, R$^{1c}$ is, same with or different from R$^{1b}$, a hydrogen atom or an aliphatic hydrocarbon group optionally having substituents, or R forms a bond with R$^0$, and among them the group represented by the formula: OR$^1$ (wherein R$^1$ represents the same meaning as defined above) is preferred.

And, R$^a$ represents an aliphatic hydrocarbon group optionally having substituents, an aromatic hydrocarbon group optionally having substituents, a heterocyclic group optionally having substituents, a group represented by the formula: OR$^{1a}$ (wherein R$^{1a}$ represents a hydrogen atom or an aliphatic hydrocarbon group optionally having substituents) or a group represented by the formula:

(wherein R$^{1a}$ represents the same meaning as defined above, R$^{1b}$ is, same with or different from R$^{1a}$, a hydrogen atom or an aliphatic hydrocarbon group optionally having substituents), or form a bond with $R^{0a}$, and among them the group represented by the formula: $OR^{1a}$ (wherein $R^{1a}$ represents the same meaning as defined above) is preferred.

When R and $R^0$ represent a bond with each other, the compound represented by the formula (Iaa) can be represented by the formula:

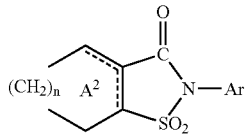
(Ihh)

wherein each symbol represents the same meaning as defined above, and specifically can be represented by the formula:

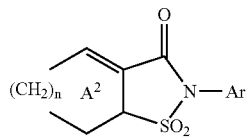
(Icc)

wherein each symbol represents the same meaning as defined above, or the formula:

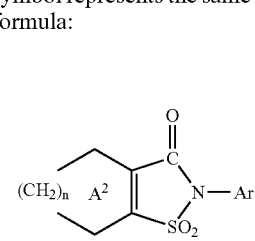
(Iii)

wherein each symbol represents the same meaning as defined above.

When R and $R^0$ represent a bond with each other, the compound represented by the formula (Ia) can be represented by the formula:

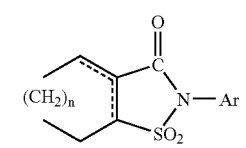
(Ih)

wherein each symbol represents the same meaning as defined above, and specifically can be represented by the formula:

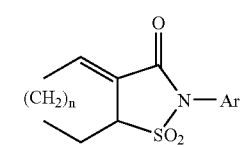
(Ic)

wherein each symbol represents the same meaning as defined above, or the formula:

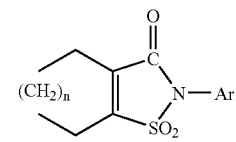
(Ii)

wherein each symbol represents the same meaning as defined above.

When $R^a$ and $R^{0a}$ represent a bond with each other, the compound represented by the formula (Ie) can be represented by the formula:

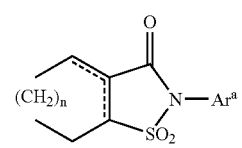
(Ij)

wherein each symbol represents the same meaning as defined above, and specifically can be represented by the formula:

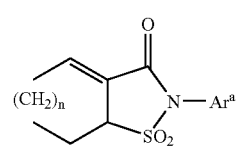
(Ik)

wherein each symbol represents the same meaning as defined above, or the formula:

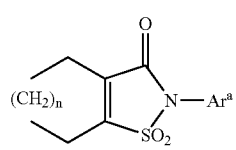
(Im)

wherein each symbol represents the same meaning as defined above.

When R is a group represented by the formula: $OR^1$ (wherein $R^1$ represents the same meaning as defined above), the compound represented by the formula (Iaa) can be represented by the formula:

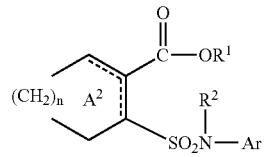
(Ibb)

wherein each symbol represents the same meaning as defined above, and specifically can be represented by the formula:

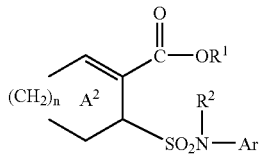

(Inn)

wherein each symbol represents the same meaning as defined above, or the formula:

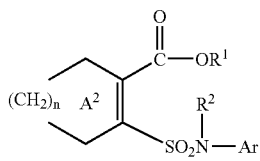

(Ioo)

wherein each symbol represents the same meaning as defined above.

When R is a group represented by the formula: $OR^1$ (wherein $R^1$ represents the same meaning as defined above), the compound represented by the formula (Ia) can be represented by the formula:

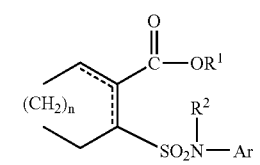

(Ib)

wherein each symbol represents the same meaning as defined above, and specifically can be represented by the formula:

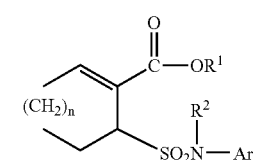

(In)

wherein each symbol represents the same meaning as defined above, or the formula:

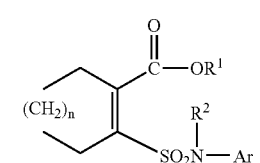

(Io)

wherein each symbol represents the same meaning as defined above.

When $R^a$ is a group represented by the formula: $OR^{1a}$ (wherein $R^{1a}$ represents the same meaning as defined above), the compound represented by the formula (Ie) can be represented by the formula:

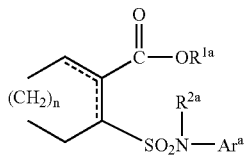

(If)

wherein each symbol represents the same meaning as defined above, and specifically can be represented by the formula:

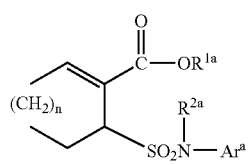

(Ip)

wherein each symbol represents the same meaning as defined above, or the formula:

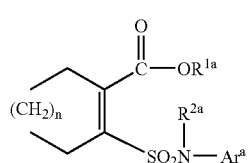

(Iq)

wherein each symbol represents the same meaning as defined above.

As the compound represented by the formula (Iaa), the compound represented by the formula (Icc) or the formula (Inn) is preferred, as the compound represented by the formula (Ia), the compound represented by the formula (Ic) or the formula (In) are preferred, and as the compound represented by the formula (Ie), the compound represented by the formula (Ik) or the formula (Ip) are preferred, Similarly, the compound represented by the formula (Id) can be represented by the formula:

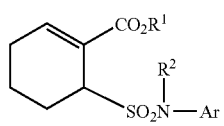

(Ir)

wherein each symbol represents the same meaning as defined above, or the formula:

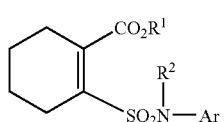

(Is)

wherein each symbol represents the same meaning as defined above, and the compound represented by the formula (Ig) can be represented by the formula:

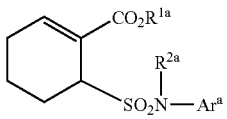
(It)

wherein each symbol represents the same meaning as defined above, or the formula:

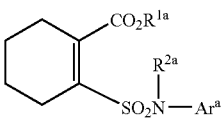
(Iu)

wherein each symbol represents the same meaning as defined above.

As the compound represented by the formula (Id), the compound represented by the formula (Ir) is preferred, as the compound represented by the formula (Ig), the compound represented by the formula (It) is preferred.

In the compound represented by the formula (Ia), when n is 1 or 2, and (i) $R^1$ is a hydrogen atom or an ethyl group, $R^0$ is a methyl group and Ar is a phenyl group, or (ii) R and $R^0$ represent a bond with each other and Ar is a phenyl group, a 2-methylphenyl group, a 4-bromophenyl group, a 4-methoxyphenyl group or a 2,6-dimethylphenyl group, a group represented by the formula:

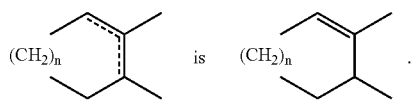

Furthermore, when n is 1 to 4, and (i) $R^1$ is a hydrogen atom or a lower alkyl group optionally having substituents, $R^1$ is a lower alkyl group optionally having substituents, and Ar is a phenyl group optionally having substituents, or (ii) R and $R^0$ represent a bond with each other and Ar is a phenyl group optionally having substituents, a group represented by the formula:

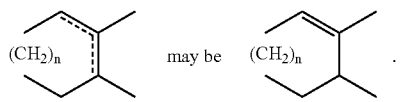

In the compound represented by the formula (Ib), when n is 1 or 2, $R^1$ is a hydrogen atom or an ethyl group, $R^0$ is a methyl group, and Ar is a phenyl group, a group represented by the formula:

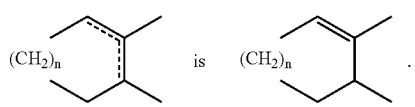

Furthermore, when n is 1 to 4, and $R^1$ is a hydrogen atom or a lower alkyl group optionally having substituents, $R^0$ is a lower alkyl group optionally having substituents, and Ar is a phenyl group optionally having substituents, a group represented by the formula:

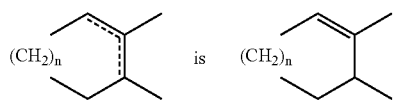

Thus, in one embodiment, the present invention provides for an emulsion composition comprising a compound of the formula:

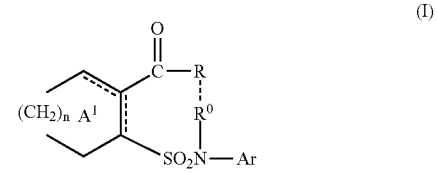
(I)

wherein R represents an optionally substituted aliphatic hydrocarbon group, an optionally substituted aromatic hydrocarbon group, an optionally substituted heterocyclic group, a group represented by the formula: $OR^1$ where $R^1$ represents a hydrogen atom or an optionally substituted aliphatic hydrocarbon group, or a group represented by the formula:

where $R^{1b}$ and $R^{1c}$ are each independently a hydrogen atom or an optionally substituted aliphatic hydrocarbon group), $R^0$ represents a hydrogen atom or an optionally substituted aliphatic hydrocarbon group, or taken together, R and $R^0$ represent a bond,

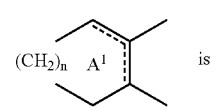

is

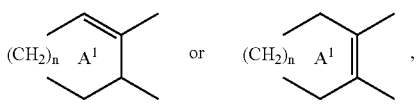

wherein n is an integer of 1 to 4, ring $A^1$ is a cycloalkene optionally substituted by 1 to 4 substituents selected from the group consisting of (i) an aliphatic hydrocarbon group optionally having substituents, (ii) an aromatic hydrocarbon group optionally having substituents, (iii) a group represented by the formula: $OR^1$ where $R^1$ represents a hydrogen atom or an aliphatic hydrocarbon group optionally having substituents, and (iv) a halogen atom, Ar represents an optionally substituted aromatic hydrocarbon group, a salt thereof or a prodrug therefor, (2) an anionic synthetic phospholipid in a proportion of about 0.0001 to about 5% weight per total volume relative to the composition in total, and (3) a naturally-occurring phospholipid in a proportion of about 0.1 to about 10% weight per total volume relative to the composition in total.

The present invention also provides for such an emulsion composition wherein R, $R^1$, $R^{1b}$, $R^{1c}$, $R^{1d}$, $A^1$ and Ar may be substituted with one to four substituents, each substituent independently selected from the group of substituents collectively identified as group Q.

The substituents of group Q consisting of (i) a 5- to 8-membered ring or condensed ring substituent group containing 1 to 4 hetero atoms selected from the group consisting of nitrogen atom which is optionally oxidized, oxygen atom and sulfur atom, where said ring is optionally substituted by 1 to 3 substituents selected from the group consisting of $C_{1-4}$ alkyl, hydroxy, oxo and $C_{1-4}$ alkoxy, (ii) oxo substituent group, (iii) hydroxyl substituent group, (iv) $C_{1-6}$ alkoxy substituent group, (v) $C_{3-10}$ cycloalkyloxy substituent group, (vi) $C_{6-10}$ aryloxy substituent group, (vii) $C_{7-19}$ aralkyloxy substituent group, (viii) a 5- to 8-membered ring or condensed ring-oxy substituent group containing 1 to 4 hetero atoms selected from the group consisting of nitrogen atom which is optionally oxidized, oxygen atom and sulfur atom, where said ring-oxy substituent group is optionally substituted by 1 to 3 substituents selected from the group consisting of $C_{1-4}$ alkyl, hydroxy, oxo and $C_{1-4}$ alkoxy, (ix) $C_{1-6}$ alkylthio substituent group where the sulfur atom may be optionally oxidized, (x) $C_{3-10}$ cycloalkylthio substituent group where the sulfur atom may be optionally oxidized, (xi) $C_{6-10}$ arylthio substituent group where the sulfur atom may be optionally oxidized, (xii) $C_{7-19}$ aralkylthio substituent group where the sulfur atom may be optionally oxidized, (xiii) a 5- to 8-membered ring or condensed ring-thio substituent group containing 1 to 4 hetero atoms selected from the group consisting of nitrogen atom which is optionally oxidized, oxygen atom and sulfur atom, where said ring-thio substituent group is optionally substituted by 1 to 3 substituents selected from the group consisting of $C_{1-4}$ alkyl, hydroxy, oxo and $C_{1-4}$ alkoxy, (xiv) a 5- to 8-membered ring or condensed ring-sulfinyl substituent group containing 1 to 4 hetero atoms selected from the group consisting of nitrogen atom which is optionally oxidized, oxygen atom and sulfur atom, where said ring-sulfinyl substituent group is optionally substituted by 1 to 3 substituents selected from the group consisting of $C_{1-4}$ alkyl, hydroxy, oxo and $C_{1-4}$ alkoxy, (xv) a 5- to 8-membered ring group or a condensed ring-sulfonyl group containing 1 to 4 hetero atoms selected from the group consisting of nitrogen atom which is optionally oxidized, oxygen atom and sulfur atom, where said ring-sulfonyl substituent group is optionally substituted by 1 to 3 substituents selected from the group consisting of $C_{1-4}$ alkyl, hydroxy, oxo and $C_{1-4}$ alkoxy, (xvi) nitro substituent group, (xvii) halogen atom, (xviii) cyano substituent group, (xix) carboxyl substituent group, (xx) $C_{1-10}$ alkoxy-carbonyl substituent group, (xxi) $C_{3-6}$ cycloalkyloxy-carbonyl substituent group, (xxii) $C_{6-10}$ aryloxy-carbonyl substituent group, (xxiii) $C_{7-19}$ aralkyloxy-carbonyl substituent group, (xxiv) a 5- to 8-membered ring or condensed ring-oxycarbonyl substituent group containing 1 to 4 hetero atoms selected from the group consisting of nitrogen atom which is optionally oxidized, oxygen atom and sulfur atom, where said ring-oxycarbonyl substituent group is optionally substituted by 1 to 3 substituents selected from the group consisting of $C_{1-4}$ alkyl, hydroxy, oxo and $C_{1-4}$ alkoxy, (xxv) $C_{6-10}$ arylcarbonyl substituent group, (xxvi) $C_{1-6}$ alkanoyl substituent group, (xxvii) $C_{3-5}$ alkenoyl substituent group, (xxviii) $C_{6-10}$ arylcarbonyloxy substituent group, (xxix) $C_{2-6}$ alkanoyloxy substituent group, (xxx) $C_{3-5}$ alkenoyloxy substituent group, (xxxi) carbamoyl substituent group or cyclic aminocarbonyl substituent group optionally substituted by 1 or 2 substituents selected from the group consisting of $C_{1-4}$ alkyl, phenyl, $C_{1-7}$ acyl and $C_{1-4}$ alkoxy-phenyl, (xxxii) thiocarbamoyl substituent group optionally substituted by 1 or 2 substituents selected from the group consisting of $C_{1-4}$ alkyl and phenyl, (xxxiii) carbamoyloxy substituent group optionally substituted by 1 or 2 substituents selected from the group consisting of $C_{1-4}$ alkyl and phenyl, (xxxiv) $C_{1-6}$ alkanoylamino substituent group, (xxxv) $C_{6-10}$ aryl-carbonylamino substituent group, (xxxvi) $C_{1-10}$ alkoxy-carboxamide substituent group, (xxxvii) $C_{6-10}$ aryloxy-carboxamide substituent group, (xxxviii) $C_{7-19}$ aralkyloxy-carboxamide substituent group, (xxxix) $C_{1-10}$ alkoxy-carbonyloxy substituent group, (xxxx) $C_{6-10}$ aryloxy-carbonyloxy substituent group, (xxxxi) $C_{7-19}$ aralkyloxy-carbonyloxy substituent group, (xxxxii) $C_{3-10}$ cycloalkyloxy-carbonyloxy substituent group, (xxxxiii) ureido substituent group optionally substituted by 1 to 3 substituents selected from the group consisting of $C_{1-4}$ alkyl and phenyl, and (xxxxiv) $C_{6-10}$ aryl substituent group optionally having 1 to 4 substituents selected from the group consisting of $C_{1-4}$ alkyl and phenyl.

The present invention further provides for an emulsion composition as described above, wherein R is (1) ①linear or branched $C_{1-20}$ alkyl, ② $C_{3-10}$ cycloalkyl, ③ $C_{4-12}$ cycloalkylalkyl, ④ lower ($C_{3-6}$) alkenyl group or ⑤ lower ($C_{3-6}$) alkynyl group optionally having 1 to 4 substituents each independently selected from the group Q; wherein when two substituents from group Q substitute said linear or branched $C_{1-20}$ alkyl, $C_{3-10}$ cycloalkyl, $C_{4-12}$ cycloalkylalkyl, $C_{3-6}$ alkenyl or $C_{3-6}$ alkynyl, said substituents may be linked to form a ring; (2) $C_{6-14}$ aromatic hydrocarbon group optionally having 1 to 5 substituents selected from the group consisting of halogen atom, $C_{1-4}$ alkyl group, $C_{1-4}$ alkoxy group, $C_{1-4}$ alkoxy-carbonyl group, carboxyl group, nitro group, cyano group, hydroxyl group, $C_{1-4}$ alkanoylamino group, $C_{3-16}$ cycloalkyl group, $C_{6-10}$ aryl group, halogeno $C_{1-4}$ alkyl group, halogeno $C_{1-4}$ alkoxy group, $C_{1-4}$ alkylthio group, $C_{1-4}$ alkylsulfonyl group, $C_{1-4}$ alkanoyl group, 5-membered aromatic heterocyclic group, carbamoyl group, $C_{1-4}$ alkyl-carbamoyl group, $C_{1-4}$ alkoxy-carbonyl-$C_{1-4}$ alkyl-carbamoyl group and 1,3-diacylguanidino-$C_{1-4}$ alkyl group, (3) a 5- to 8-membered ring or a condensed ring group containing 1 to 4 hetero atoms selected from the group consisting of nitrogen atom which is optionally oxidized, oxygen atom and sulfur atom, where said ring group optionally has 1 to 3 substituents selected from the group consisting of $C_{1-4}$ alkyl, hydroxy, oxo and $C_{1-4}$ alkoxy, (4) a group of the formula —$OR^1$ wherein $R^1$ is (i) hydrogen atom or (ii) ① linear or branched $C_{1-20}$ alkyl, ② $C_{3-10}$ cycloalkyl, ③ $C_{4-12}$ cycloalkylalkyl, ④ lower $C_{3-6}$ alkenyl group or ⑤ lower $C_{3-6}$ alkynyl group optionally having 1 to 4 substituents, each independently selected from the group Q; wherein when two substituents from group Q substitute said linear or branched $C_{1-20}$ alkyl, $C_{3-10}$ cycloalkyl, $C_{4-12}$ cycloalkylalkyl, $C_{3-6}$ alkenyl or $C_{3-6}$ alkynyl, said substituents may be linked to form a ring; or (5) a group of the formula

wherein $R^{1b}$ and $R^{1c}$ are each independently a (i) hydrogen atom or (ii) ① linear or branched $C_{1-20}$ alkyl, ② $C_{3-10}$ cycloalkyl, ③ $C_{4-12}$ cycloalkylalkyl, ④ lower $C_{3-6}$ alkenyl group or ⑤ lower $C_{3-6}$ alkynyl group optionally substituted with 1 to four substituents each independently selected from the group Q; wherein when two substituents from group Q substitute said linear or branched $C_{1-20}$ alkyl, $C_{3-10}$ cycloalkyl, $C_{4-12}$ cycloalkylalkyl, $C_{3-6}$ alkenyl or $C_{3-6}$ alkynyl, said substituents may be linked to form a ring; $R^0$ represents a hydrogen atom, a linear or branched $C_{1-20}$ alkyl, a $C_{3-10}$ cycloalkyl, a $C_{4-12}$ cycloalkylalkyl, a lower ($C_{3-6}$) alkenyl group or a lower ($C_{3-6}$) alkynyl group, or R and $R^0$ represent a bond with each other, ring $A^1$ represents cycloalkene optionally substituted by 1 to 4 substituents, each independently selected from the group consisting of linear or branched $C_{1-20}$ alkyl, $C_{3-10}$ cycloalkyl, $C_{4-12}$ cycloalkylalkyl, $C_{3-6}$ alkenyl or $C_{3-6}$ alkynyl; optionally substituted with 1 to four substituents, each of said substituents independently selected from substituent group Q; wherein when two substituents from group Q substitute said linear or branched $C_{1-20}$ alkyl, $C_{3-10}$ cycloalkyl, $C_{4-12}$ cycloalkylalkyl, $C_{3-6}$ alkenyl or $C_{3-6}$ alkynyl, said substituents may be linked to form a ring; (2) a $C_{6-14}$ aromatic hydrocarbon group optionally having 1 to 5 substituents selected from the group consisting of halogen atom, $C_{1-4}$ alkyl group, $C_{1-4}$ alkoxy group, $C_{1-4}$ alkoxy-carbonyl group, carboxyl group, nitro group, cyano group, hydroxyl group, $C_{1-4}$ alkanoylamino group, $C_{3-6}$ cycloalkyl group, $C_{6-10}$ aryl group, halogeno $C_{1-4}$ alkyl group, halogeno $C_{1-4}$ alkoxy group, $C_{1-4}$ alkylthio group, $C_{1-4}$ alkylsulfonyl group, $C_{1-4}$ alkanoyl group, 5-membered aromatic heterocyclic group, carbamoyl group, $C_{1-4}$ alkyl-carbamoyl group, $C_{1-4}$ alkoxy-carbonyl-$C_{1-4}$ alkyl-carbamoyl group and 1,3-diacylguanidino-$C_{1-4}$ alkyl group; (3)—$OR^1$ wherein $R^1$ is (i) hydrogen atom or (ii) ① linear or branched $C_{1-20}$ alkyl, ② $C_{3-10}$ cycloalkyl, ③ $C_{4-12}$ cycloalkylalkyl, ④ lower $C_{3-6}$ alkenyl group or ⑤ lower $C_{3-6}$ alkynyl group optionally having 1 to 4 substituents, each independently selected from the group Q; wherein when two substituents from group Q substitute said linear or branched $C_{1-20}$ alkyl, $C_{3-10}$ cycloalkyl, $C_{4-12}$ cycloalkylalkyl, $C_{3-6}$ alkenyl or $C_{3-6}$ alkynyl, said substituents may be linked to form a ring; (4) halogen atoms and, Ar represents a $C_{6-14}$ aromatic hydrocarbon group optionally having 1 to 5 substituents selected from the group consisting of halogen atom, $C_{1-4}$ alkyl group, $C_{1-4}$ alkoxy group, $C_{1-4}$ alkoxycarbonyl group, carboxyl group, nitro group, cyano group, hydroxyl group, $C_{1-4}$ alkanoylamino group, $C_{3-6}$ cycloalkyl group, $C_{6-10}$ aryl group, halogeno $C_{1-4}$ alkyl group, halogeno $C_{1-4}$ alkoxy group, $C_{1-4}$ alkylthio group, $C_{1-4}$ alkylsulfonyl group, $C_{1-4}$ alkanoyl group, 5-membered aromatic heterocyclic group, carbamoyl group, $C_{1-4}$ alkyl-carbamoyl group, $C_{1-4}$ alkoxy-carbonyl-$C_{1-4}$ alkyl-carbamoyl group and 1,3-diacylguanidino-$C_{1-4}$ alkyl group.

The present invention further provides for an emulsion composition, as described above, wherein when two substituents from group Q substitute said linear or branched $C_{1-20}$ alkyl, $C_{3-10}$ cycloalkyl, $C_{4-12}$ cycloalkylalkyl, $C_{3-6}$ alkenyl or $C_{3-6}$ alkynyl, said substituents may be linked to form a ring; wherein said ring is an indanyl group or a 1,2,3,4-tetrahydronaphthyl group; and wherein said ring may be further substituted by 1 to 4 substituents each independently selected from group Q.

The present invention provides for an emulsion composition, wherein said anionic synthetic phospholipid is a compound of the formula

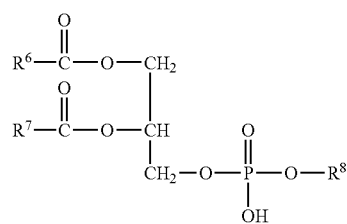

wherein $R^6$ and $R^7$ are the same or different and each is a $C_{7-20}$ chain hydrocarbon group, and $R^8$ is

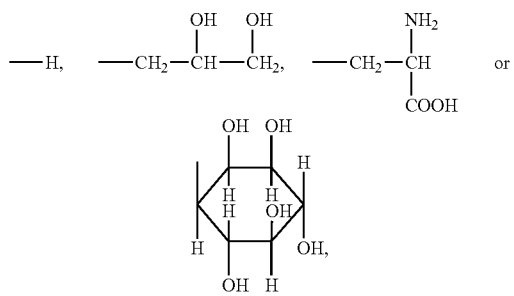

or a salt thereof.

The present invention provides for an emulsion composition as described above, wherein said anionic synthetic phospholipid is a compound of the formula

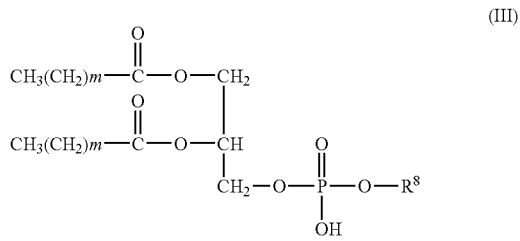

wherein m is an integer of 7-20, and $R^8$ is

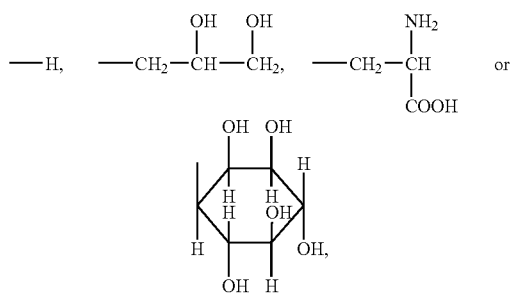

or a salt thereof.

Thus, in one embodiment, the present invention provides for an emulsion composition as described, wherein said anionic synthetic phospholipid is dimyristoylphosphatidylglycerol. The present invention provides for an emulsion composition wherein said naturally-occurring phospholipid is egg yolk lecithin or soybean lecithin. In a preferred embodiment, said naturally-occurring phospholipid is egg yolk lecithin.

The present invention provides for an emulsion composition comprising about 0.1 to about 3% weight per total volume of d-ethyl 6-[N-(2-chloro-4-fluorophenyl)sulfamoyl]-1-cyclohexene-1-carboxylate, about 5 to about 25% weight per total volume of soybean oil, about 1 to about 3% weight per total volume of egg yolk lecithin, about 0.05 to about 0.5% weight per total volume dimyristoyl phosphatidylglycerol and water.

The present invention provides for an emulsion composition comprising about 0.1 to about 3% weight per total volume of d-ethyl 6-[N-(2-chloro-4-fluorophenyl)sulfamoyl]-1-cyclohexene-1-carboxylate, about 5 to about 25% weight per total volume of soybean oil, about 1 to about 3% weight per total volume of egg yolk lecithin, about 0.05 to about 0.5% weight per total volume distearoyl phosphatidylglycerol and water.

The present invention further provides for an emulsion composition as described, wherein said anionic synthetic phospholipid is contained in a proportion of about 0.0001 to about 2% weight per total volume of the composition in total. Further, the invention provides for an emulsion composition, wherein said anionic synthetic phospholipid is contained in a proportion of about 0.2% weight per total volume of the composition in total.

The present invention further provides for an emulsion composition as described, wherein a compound of formula (I), a salt thereof or a prodrug therefor is in a proportion of about 0.001 to about 95 weight percent of the composition in total. Further, the invention provides for an emulsion composition, wherein a compound of formula (I), a salt thereof or a prodrug therefor is in a proportion of about 0.01 to about 30 weight percent of the composition in total.

The present invention provides for an emulsion composition as described, which further comprises a component selected from the group consisting of oil, water and a combination thereof. Further, the invention provides for an emulsion composition, further comprising an oil which is selected from the group consisting of vegetable oil, a partially hydrogenated vegetable oil, mono-acid glyceride, mixed acid glyceride and medium-size chain fatty acid glycerine ester. In a preferred embodiment, the oil is a vegetable oil. The present invention provides for an emulsion composition, wherein said vegetable oil is selected from the group consisting of soybean oil, cottonseed oil, rapeseed oil, peanut oil, safflower oil, sesame oil, rice bran oil, corn germ oil, sunflower oil, poppy oil and olive oil. A preferred vegetable oil is a soybean oil.

The present invention provides for an emulsion composition, wherein oil is in a proportion of about 1 to about 30 weight percent of the composition in total. Further, the invention provides for an emulsion composition, which further comprises glycerine.

The invention provides for an emulsion composition, which is an oil-in-water composition.

The invention provides for an emulsion composition, which has a pH from about 3 to about 6.

The invention provides for an emulsion composition, which is for an injection.

The invention provides for an emulsion composition comprising: about 1% weight per total volume of d-ethyl 6-[N-(2-chloro-4-fluorophenyl)sulfamoyl]-1-cyclohexene-1-carboxylate, about 20% weight per total volume of soybean oil, about 1.2% weight per total volume of egg yolk lecithin, and about 0.2% weight per total volume dimyristoyl phosphatidylglycerol and water.

The invention provides for an emulsion composition comprising: about 1% weight per total volume of d-ethyl 6-[N-(2-chloro-4-fluorophenyl)sulfamoyl]-1-cyclohexene-1-carboxylate, about 20% weight per total volume of soybean oil, about 1.2% weight per total volume of egg yolk lecithin, about 0.2% weight per total volume distearoyl phosphatidylglycerol and water.

The invention provides for an emulsion composition, as described above, which comprises a disperse phase particle comprising anionic synthetic phospholipid, naturally-occurring phospholipid, an oil component and compound (I), a salt thereof or a prodrug therefor, and water wherein the disperse phase particle is dispersed.

The invention provides for an emulsion composition wherein the disperse phase has an average particle size of about 25 to about 500 nm.

The invention provides for an emulsion composition which is a nitric oxide or cytokine production inhibitor, or a nitric oxide inhibitor and a cytokine production inhibitor.

The invention provides for an emulsion composition which is an agent for treating cardiac disease, autoimmune disease, sepsis or septic shock.

The invention further provides for a method for making an emulsion composition, as described, comprising the steps of: (a) adding an anionic synthetic phospholipid, and a naturally-occurring phospholipid to a compound represented by the formula:

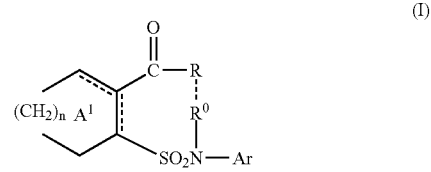

as described above, wherein R represents an optionally substituted aliphatic hydrocarbon group, an optionally substituted aromatic hydrocarbon group, an optionally substituted heterocyclic group, a group represented by the formula: OR$^1$ where R$^1$ represents a hydrogen atom or an optionally substituted aliphatic hydrocarbon group, or a group represented by the formula:

where R$^{1b}$ and R$^3$C are each independently a hydrogen atom or an optionally substituted aliphatic hydrocarbon group, R$^0$ represents a hydrogen atom or an optionally substituted aliphatic hydrocarbon group, or taken together, R and R$^0$ represent a bond,

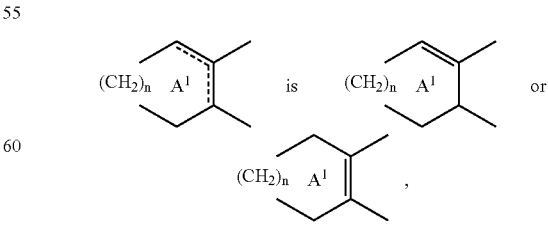

wherein n is an integer of 1 to 4,
ring A$^1$ is a cycloalkene optionally substituted by 1 to 4 substituents selected from the group consisting of (i) an aliphatic hydrocarbon group optionally having substituents, (ii) an aromatic hydrocarbon group optionally having substituents, (iii) a group represented by the formula: OR1 where R1 represents a hydrogen atom or an aliphatic hydrocarbon group optionally having substituents, and (iv) a halogen atom, Ar represents an optionally substituted aromatic hydrocarbon group, a salt thereof or a prodrug therefor, in oil and water to form an emulsion; and then, (b) adjusting said emulsion to a pH of not more than about 6 to form a stable emulsion.

The invention provides for a method, as described, whereby stability of said stable emulsion during autoclave sterilization is improved.

The invention provides for a method for treating cardiac disease, autoimmune disease, sepsis or septic shock, comprising administrating to a mammal in need thereof a pharmaceutically effective amount of the emulsion composition described above.

The present invention provides for use of the emulsion composition of the invention for manufacturing an agent for preventing or treating cardiac disease, autoimmune disease, sepsis or septic shock.

As the "aliphatic hydrocarbon group" of the "aliphatic hydrocarbon group optionally having substituents" (optionally substituted aliphatic hydrocarbon group) represented by R, $R^1$, $R^{1a}$, $R^{1b}$, $R^{1c}$, and the "aliphatic hydrocarbon group" represented by $R^0$, $R^{0a}$, $R^2$, $R^{2a}$, for example, an alkyl group, a cycloalkyl group, a cycloalkylalkyl group, an alkenyl group, an alkynyl group, etc. are preferred.

As the alkyl group, for example, a linear or branched alkyl group having 1 to 20 carbons (e.g., a methyl group, an ethyl group, a n-propyl group, an isopropyl group, a n-butyl group, an isobutyl group, a sec-butyl group, a tert-butyl group, a pentyl group, a hexyl group, a heptyl group, an octyl group, a nonyl group, a decyl group, a dodecyl group, etc.), etc. are preferred, and particularly, for example, a lower alkyl group having 1 to 6 carbons (e.g., a methyl group, an ethyl group, a n-propyl group, an isopropyl group, a n-butyl group, an isobutyl group, a sec-butyl group, a tert-butyl group, etc.), etc. are preferred.

As the cycloalkyl group, for example, a cycloalkyl group having 3 to 10 carbons (e.g., a cyclopropyl group, a cyclobutyl group, a cyclopentyl group, a cyclohexyl group, a cycloheptyl group, a cyclooctyl group, etc.), etc. are preferred, and particularly, for example, a cycloalkyl group having 3 to 6 carbons (e.g., a cyclopropyl group, a cyclobutyl group, a cyclopentyl group, a cyclohexyl group, etc.), etc. are preferred.

As the cycloalkylalkyl group, for example, a cycloalkylalkyl group having 4 to 12 carbons (e.g., a cyclopropylmethyl group, a cyclopentylmethyl group, a cyclohexylmethyl group, a cycloheptylmethyl group, etc.), etc. are preferred, and particularly, for example, a cycloalkylalkyl group having 4 to 8 (particularly, 4 to 7) carbons (e.g., a cyclopropylmethyl group, a cyclopentylmethyl group, a cyclohexylmethyl group, etc.), etc. are preferred.

As the alkenyl group, for example, a lower alkenyl group having 3 to 6 carbons (e.g., a propenyl group, a butenyl group, a pentenyl group, etc.), and particularly, for example, a lower alkenyl group having 3 or 4 carbons (e.g., a propenyl group, a butenyl group, etc.), etc. are preferred.

As the alkynyl group, for example, a lower alkynyl group having 3 to 6 carbons (e.g., a propynyl group, a butynyl group, a pentynyl group, etc.), and particularly, for example, a lower alkenyl group having 3 or 4 carbons (e.g., a propynyl group, a butynyl group, etc.), etc. are preferred.

As the "substituents" of the above mentioned "aliphatic hydrocarbon group optionally having substituents" (option-ally substituted aliphatic hydrocarbon group), for example, a heterocyclic group, an oxo group, a hydroxy group, a $C_{1-6}$ alkoxy group, a $C_{3-10}$ (particularly, $C_{3-6}$) cycloalkyloxy group, a $C_{6-10}$ aryloxy group, a $C_{7-19}$ (particularly, $C_{7-12}$) aralkyloxy group, a herocyclic oxy group, a $C_{1-6}$ alkylthio group (the sulfur atom may be oxidized), a $C_{3-10}$ (particularly, $C_{3-6}$) cycloalkylthio group (the sulfur atom may be oxidized), a $C_{6-10}$ arylthio group (the sulfur atom may be oxidized), a $C_{7-19}$ (particularly, $C_{7-12}$) aralkyloxy group (the sulfur atom may be oxidized), a herocyclic thio group, a herocyclic sulfinyl group, a herocyclic sulfonyl group, a nitro group, a halogen atom, a cyano group, a carboxyl group, a $C_{1-10}$ (particularly, $C_{1-6}$) alkoxy-carbonyl group, a $C_{3-6}$ cycloalkyloxy-carbonyl group, a $C_{6-10}$ aryloxy-carbonyl group, a $C_{7-19}$ (particularly, $C_{7-12}$) aralkyloxy-carbonyl group, a herocyclic oxycarbonyl group, a $C_{6-10}$ aryl-carbonyl group, $C_{1-6}$ alkanoyl group, $C_{3-5}$ alkenoyl group, a $C_{6-10}$ aryl-carbonyloxy group, a $C_{2-6}$ alkanoyloxy group, a $C_{3-5}$ alkenoyloxy group, a carbamoyl group optionally having substituents, a thiocarbamoyl group optionally having substituents, a carbamoyloxy group optionally having substituents, a $C_{1-6}$ arkanoylamino group, a $C_{6-10}$ aryl-carbonylamino group, a $C_{1-10}$ (particularly, $C_{1-6}$) alkoxy-carboxamide group, a $C_{6-10}$ aryloxy-carboxamide group, a $C_{7-19}$ (particularly, $C_{7-12}$) aralkyloxy-carboxamide group, a $C_{1-10}$ (particularly, $C_{1-6}$) alkoxy-carbonyloxy group, a $C_{6-10}$ aryloxy-carbonyloxy group, group, a $C_{7-19}$ (particularly, $C_{7-12}$) aralkyloxy-carbonyloxy group, a $C_{3-10}$ (particularly, $C_{3-6}$)cycloalkyloxy-carbonyloxy group, an ureido group optionally having substituents, a $C_{6-10}$ aryl group optionally having substituents, etc. are used.

These substituents are substituted at substitutable positions in the above mentioned "aliphatic hydrocarbon group", and the substituents are not limited to one and may be same or different and a few numbers (2 to 4).

As the "$C_{1-6}$ alkoxy group", for example, a methoxy group, an ethoxy group, a n-propoxy group, an isopropoxy group, a n-butoxy group, a tert-butoxy group, a n-pentyloxy group, a n-hexyloxy group, etc. are used, as the "$C_{3-10}$ cycloalkyloxy group", for example, a cyclopropyloxy group, a cyclohexyloxy group, etc. are used, as the "$C_{6-10}$ aryloxy group", for example, a phenoxy group, a naphtyloxy group, etc. are used, as the "$C_{7-19}$ aralkyloxy group", for example, a benzyloxy group, a 1-phenylethyloxy group, a 2-phenylethyloxy group, a benzhydryloxy group, a 1-naphthylmethyloxy group, etc. are used, as the "$C_{1-6}$ alkylthio group (the sulfur atom may be oxidized)", for example, a methylthio group, an ethylthio group, a n-propylthio group, a n-butylthio group, a methylsulfinyl group, a methylsulfonyl group, etc. are used, as the "$C_{3-10}$ cycloalkylthio group (the sulfur atom may be oxidized)", for example, a cyclopropylthio group, a cyclohexylthio group, a cyclopentylsulfinyl group, a cyclohexylsulfonyl group, etc. are used, as the "$C_{6-10}$ arylthio group (the sulfur atom may be oxidized)", for example, a phenylthio group, a naphthylthio group, a phenylsulfinyl group, a phenylsulfonyl group, etc. are used, as the "$C_{9-19}$ aralkylthio group (the sulfur atom may be oxidized)", for example, a benzylthio group, a phenylethylthio group, a benzhydrylthio group, a benzylsulfinyl group, a benzylsulfonyl group, etc. are used, as the "halogen atom", for example, a fluorine atom, a chlorine atom, a bromine atom, an iodine atom, ets. are used, as the "$C_{1-10}$ alkoxy-carbonyl group", for example, a methoxycarbonyl group, an ethoxycarbonyl group, a n-propoxycarbonyl group, an isopropoxycarbonyl group, a n-butoxycarbonyl group, a isobutoxycarbonyl group, a tert-butoxycarbonyl group, etc. are used, as the "$C_{3-6}$ cycloalkyloxycarbonyl group", for example, a cyclopropyloxycarbonyl group, a cyclopentyloxycarbonyl group, a cyclohexyloxycarbonyl group, a norbornyloxycarbonyl group, etc. are used, as the "$C_{6-10}$ aryloxy-carbonyl group", for example, a phenoxycarbonyl group, a naphtyloxycarbonyl group, etc. are used, as the "$C_{7-19}$ aralkyl-oxycarbonyl group", for example, a benzyloxycarbonyl group, a benzhydryloxycarbonyl group, a 2-phenethyloxycarbonyl group, etc. are used, as the "$C_{6-10}$ aryl-carbonyl group", for example, a benzoyl group, a naphtoyl group, a phenylacetyl group, etc. are used, as the "$C_{1-6}$ alkanoyl group", for example, a formyl group, an acetyl group, a propionyl group, a butyryl group, a valeryl group, a pivaloyl group, etc. are used, as the "$C_{3-5}$ alkenoyl group", for example, an acrynoyl group, a crotnoyl group, etc. are used, as the "$C_{6-10}$ aryl-carbonyloxy group", for example, a benzoyloxy group, a naphtoyloxy group, a phenylacetoxy group, etc. are used, as the "$C_{2-6}$ alkanoyloxy group", for example, an acetoxy group, a propionyloxy group, a butyryloxy group, a valeryloxy group, a pivaloyloxy group, etc. are used, as the "$C_{3-5}$ alkenoyl group", for example, an acrynoyloxy group, a crotnoyloxy group, etc. are used.

As the "carbamoyl group optionally having substituents" (optionally substituted carbamoyl group), for example, a carbamoyl group or a cyclicaminocarbonyl group, which may be substituted by 1 or 2 substituents selected from $C_{1-4}$ alkyl (e.g., methyl, ethyl, etc.), phenyl, $C_{1-7}$ acyl (e.g., acetyl, propionyl, benzoyl, etc.), $C_{1-4}$ alkoxy-phenyl (e.g., methoxyphenyl, etc.), etc. and specifically for example a carbamoyl group, a N-methylcarbamoyl group, a N-ethylcarbamoyl group, a N,N-dimethylcarbamoyl group, a N,N-diethylcarbamoyl group, a N-phenylcarbamoyl group, a N-acetylcarbamoyl group, a N-benzoylcarbamoyl group, a N-(p-methoxyphenyl)carbamoyl group, a 1-pyrrolydinylcarboyl group, a piperazinocarboyl group, a 1-piperazinylcarboyl group, a morpholinocarbamoyl group, etc. are used.

As the "thiocarbamoyl group optionally having substituents" (optionally substituted thiocarbamoyl group), for example, a thiocarbamoyl group which may be substituted by 1 or 2 substituents selected from $C_{1-4}$ alkyl (e.g., methyl, ethyl, etc.), phenyl, etc. and specifically for example a thiocarbamoyl group, a N-methylthiocarbamoyl group, a N-phenylthiocarbamoyl group, etc. are used.

As the "carbamoyloxy group optionally having substituents" (optionally substituted carbamoyloxy group), for example, a carbamoyloxy group which may be substituted by 1 or 2 substituents selected from $C_{1-4}$ alkyl (e.g., methyl, ethyl, etc.), phenyl, etc. and specifically for example a carbamoyloxy group, a N-methylcarbamoyloxy group, a N,N-dimethylcarbamoyloxy group, a N-ethylcarbamoyloxy group, a N-phenylcarbamoyloxy group, etc. are used.

As the "$C_{1-6}$ alkanoylamino group", for example, an acetoamide group, a propionamide group, a butyroamide group, a valeroamide group, a pivaroamide group, etc. are used, as the "$C_{6-10}$ aryl-carbonylamino group", for example, a benzamide group, a naphtoamide group, a phtalimide group, etc. are used, as the "$C_{1-10}$ alkoxy-carboxamide group", for example, a methoxycarboxamide ($CH_3OCONH-$) group, an ethoxycarboxamide group, a tert-butoxycarboxamide group, etc. are used, as the "$C_{6-10}$ aryloxy-carboxamide group", for example, a phenoxycarboxamide ($C_6H_5OCONH-$) group, etc. are used, as the "$C_{7-10}$ aralkyloxy-carboxamide group", for example, a benzyloxycarboxamide ($C_6H_5CH_2OCONH-$) group, a benzhydryloxycarboxamide group, etc. are used, as the "$C_{1-10}$ alkoxy-carbonyloxy group", for example, a methoxycarbonyloxy group, an ethoxycarbonyloxy group, a n-propoxycarbonyloxy group, an isopropoxycarbonyloxy group, a n-butoxycarbonyloxy group, a tert-butoxycarbonyloxy group, a n-pentyloxycarbonyloxy group, a n-hexyloxycarbonyloxy group, etc. are used, as the etc. are used, as the "$C_{6-10}$ aryloxy-carbonyloxy group", for example, a phenoxycarbonyloxy group, a naphthyloxycarbonyloxy group, etc. are used, as the "$C_{7-19}$ aralkyloxy-carbonyloxy group", for example, a benzylnoxycarbonyloxy group, a 1-phenylethyloxycarbonyloxy group, a 2-phenylethyloxycarbonyloxy group, a benzhydryloxycarbonyloxy group, etc. are used, and as the "$C_{3-10}$ cycloalkyloxy-carbonyloxy group", for example, a cyclopropyloxycarbonyloxy group, a cyclohexyloxycarbonyloxy group, etc. are used.

As the "ureido group optionally having substituents" (optionally substituted ureido group), for example, an ureido group optionally substituted by 1 to 3 substituents selected from a $C_{1-4}$ alkyl group (e.g., a methyl group, an ethyl group, etc.), a phenyl group, etc. are used, and for example an ureido group, a 1-methylureido group, a 3-methylureido group, a 3,3-dimethylureido group, a 1,3-dimethylureido group, a 3-phenylureido group, etc. used.

When a heterocyclic group, a heterocyclic oxy group, a heterocyclic thio group, a heterocyclic sulfinyl group, a hetrosulfonyl group or a heterocyclicoxycarbonyl group is used as the "substituents" of the "aliphatic hydrocarbon group optionally having substituents", the heterocyclic group represents a group formed by excluding one hydrogen atom which binds to the heterocycle, and it represents, for example, a 5- to 8-membered cyclic (preferably 5- to 6-membered cyclic) group containing 1 to a few, preferably 1 to 4 hetero atoms such as a nitrogen atom (optionally oxidized), an oxygen atom, a sulfur atom, etc., or a condensed cyclic group thereof. As these heterocyclic group, for example, a pyrrolyl group, a pyrazolyl group, an imidazolyl group, a 1,2,3-triazolyl group, a 1,2,4-triazolyl group, a tetrazolyl group, a furyl group, a thienyl group, an oxazolyl group, an isoxazolyl group, a 1,2,3-oxadiazolyl group, a 1,2,4-oxadiazolyl group, a 1,2,5-oxadiazolyl group, a 1,3,4-oxadiazolyl group, a thiazolyl group, an isothiazolyl group, a 1,2,3-thiadiazolyl group, a 1,2,4-thiadiazolyl group, a 1,2,5-thiadiazolyl group, a 1,3,4-thiadiazolyl group, a pyridyl group, a pyridazinyl group, a pyrimidinyl group, a pyrazinyl group, an indolyl group, a pyranyl group, a thiopyranyl group, a dioxynyl group, a dioxolyl group, a quinolyl group, a pyrido[2,3-d]pyrimidinyl group, 1,5-, 1,6-, 1,7-, 1,8-, 2,6- or 2,7-naphthyridyl group, a thieno[2,3-d]pyridyl group, a benzpyranyl group, a tetrahydrofuryl group, a tetrahydropyranyl group, a dioxoranyl group, a dioxanyl group, etc. are used.

These heterocyclic groups may be substituted at possible positions by 1 to 3 substituents selected from $C_{1-4}$ alkyl (e.g., methyl, ethyl, etc.), hydroxy, oxo, $C_{1-4}$ alkoxy (e.g., methoxy, ethoxy, etc.), etc.

As the "$C_{6-10}$ aryl group" the "$C_{6-10}$ aryl group optionally having substituents" (optionally substituted $C_{6-10}$ aryl group), for example, a phenyl group, a naphthyl group, etc. are used. The $C_{6-10}$ aryl group may be substituted at a substitutable position by a substituent selected from the those listed as a "substituent" (except for an optionally substituted $C_{6-10}$ aryl group) of the "aliphatic hydrocarbon optionally having substituents" (optionally substituted aliphatic hydrocarbon group)
    described above. Such a substituent is substituted at a substitutable position in a $C_{6-10}$ aryl group, and the number of such substituents is not limited to one, and, the same or different, more than one (2 to 4) substituents may exist.

In the "aliphatic hydrocarbon group optionally having substituents", the substituent together with the aliphatic hydrocarbon group may form an optionally substituted fused ring group, and as these condensed ring groups, an indanyl group, a 1,2,3,4-tetrahydronaphthyl group, etc. are used. This condensed ring group may be substituted at a substitutable position by a substituent selected from the those listed as a "substituent" of the "aliphatic hydrocarbon optionally having substituents" described above. Such a substituent is substituted at a substitutable position in a fused ring group, and the number of such substituents is not limited to one, and, the same or different, more than one (2 to 4) substituents may exist.

As R, $R^1$, $R^{1a}$, $R^{1b}$, $R^{1c}$, for example, a lower alkyl group having 1 to 6 carbon atoms (e.g., a methyl group, an ethyl group, a n-propyl group, an isopropyl group, a n-butyl group, an isobutyl group, a t-butoxycarbonylmethyl group, a hydroxyethyl group and the like) optionally having substituents, and of them a methyl group, an ethyl group, a n-propyl group, an isopropyl group, a n-butyl group, an isobutyl group, etc. are preferably used. Particularly, a methyl group, an ethyl group, a n-propyl group and the like, etc. are preferred, and an ethyl group is preferred particularly.

As $R^2$, $R^{2a}$, for example, a hydrogen atom, a lower alkyl group having 1 to 6 carbon atoms (e.g., a methyl group, an ethyl group, a n-propyl group, an isopropyl group, a n-butyl group, an isobutyl group, a t-butoxycarbonylmethyl group, a hydroxyethyl group and the like), etc. are preferably used, and a hydrogen atom, a methyl group, etc. are preferably used and particularly a hydrogen atom, etc. are preferably used.

As the "aromatic hydrocarbon group" of the "aromatic hydrocarbon group optionally having substituents" (optionally substituted aromatic hydrocarbon group) represented by R, for example, an aromatic hydrocarbon group having 6 to 14 carbon atoms (e.g., a phenyl group, a naphthyl group, a biphenyl group, an anthryl group, an indenyl group and the like) and the like, and particularly an aryl group having 6 to 10 carbon atoms and the like (e.g., phenyl and naphthyl groups) are preferred and a phenyl group and the like are particularly preferred.

As the "substituent" of the "aromatic hydrocarbon group optionally having substituents" represented by R, for example, a halogen atom (e.g., fluorine, chlorine, bromine, iodine and the like), a lower ($C_{1-4}$) alkyl group (e.g., a methyl group, an ethyl group, a propyl group, a butyl group and the like), a lower ($C_{1-4}$) alkoxy group (e.g., a methoxy group, an ethoxy group, a propoxy group, a butoxy group and the like), a lower ($C_{1-4}$) alkoxycarbonyl group (e.g., a methoxycarbonyl group, an ethoxycarbonyl group, a propoxycarbonyl group, a butoxycarbonyl group and the like), a carboxyl group, a nitro group, a cyano group, a hydroxyl group, an acylamino group (e.g., an alkanoylamino group having 1 to 4 carbon atoms such as an acetylamino group, a propyonylamino group, a butyrylamino group and the like), a cycloalkyl group having 3 to 6 carbon atoms (e.g., a cyclopropyl group, a cyclopentyl group and the like), an aryl group having 6 to 10 carbon atoms (e.g., a phenyl group, a naphthyl group, an indenyl group and the like), a halogeno-lower ($C_{1-4}$) alkyl group (e.g., a trifluoromethyl group, a trifluoroethyl group and the like), a halogeno-lower ($C_{1-4}$) alkoxy group (e.g., a trifluoromethoxy group, a 1,1,2,2-tetrafluoroethoxy group, a 2,2,3,3,3-pentafluoropropoxy group and the like), a lower ($C_{1-4}$) alkylthio group (e.g., a methylthio group, an ethylthio group, a propionylthio group and the like), a lower ($C_{1-4}$) alkylsulfonyl group (e.g., a methanesulfonyl group, an ethanesulfonyl group, a propanesulfonyl group and the like), a lower ($C_{1-4}$) alkanoyl group (e.g., a formyl group, an acetyl group, a propionyl group and the like), a 5-membered aromatic heterocyclic group (e.g., a 1,2,3-triazolyl group, a 1,2,4-triazolyl group, a tetrazolyl group, a thiazolyl group, an isothiazolyl group, an oxazolyl group, an isooxyazolyl group, a thiadiazolyl group, a thienyl group, a furyl group and the like), a carbamoyl group, a lower ($C_{1-4}$) alkyl-carbamoyl group (e.g., a methylcarbamoyl group, a dimethylcarbamoyl group, a propionylcarbamoyl group and the like), a lower ($C_{1-4}$) alkoxy-carbonyl-lower ($C_{1-4}$) alkyl-carbamoyl group (e.g., a butoxycarbonylmethylcarbamoyl group, an ethoxycarbonylmethylcarbamoyl group and the like), a 1,3-diacylguanidino-lower ($C_{1-4}$) alkyl group and the like (e.g., 1,3-diacetylguanidinomethyl, 1,3-bis-t-butoxycarbonylguanidinomethyl and the like) are used, and a halogen atom (e.g., fluorine, chlorine, bromine, iodine atoms and the like), a lower ($C_{1-4}$) alkyl group and the like (e.g., a methyl group, an ethyl group, a propyl group, a butyl group and the like) are preferably used, and a fluorine atom, a chlorine atom and a methyl group are more preferably used.

These substituents are substituted at substitutable positions in the aromatic hydrocarbon group, and the number of the substituents is preferably 1 to 5, more preferably 1 to 3, most preferably 1 to 2. When two or more of such substituents are present, they may be the same or different.

The "heterocyclic group" in the "heterocyclic group optionally having substituents" (optionally substituted heterocyclic group) represented by R means a 5- to 8-membered (preferably 5- to 6-membered) ring group having 1 to several, preferably 1 to 4, hetero atoms such as a nitrogen atom (optionally oxidized), an oxygen atom, a sulfur atom and the like, or a condensed ring group thereof. As these heterocyclic group, for example, a pyrrolyl group, a pyrazolyl group, an imidazolyl group, a 1,2,3-triazolyl group, a 1,2,4-triazolyl group, a tetrazolyl group, a furyl group, a thienyl group, an oxazolyl group, an isoxazolyl group, a 1,2,3-oxadiazolyl group, a 1,2,4-oxadiazolyl group, a 1,2,5-oxadiazolyl group, a 1,3,4-oxadiazolyl group, a thiazolyl group, an isothiazolyl group, a 1,2,3-thiadiazolyl group, a 1,2,4-thiadiazolyl group, a 1,2,5-thiadiazolyl group, a 1,3,4-thiadiazolyl group, a pyridyl group, a pyridazinyl group, a pyrimidinyl group, a pyrazinyl group, an indolyl group, a pyranyl group, a thiopyranyl group, a dioxynyl group, a dioxolyl group, a quinolyl group, a pyrido[2,3-d]pyrimidinyl group, 1,5-, 1,6-, 1,7-, 1,8-, 2,6- or 2,7-naphthyridyl group, a thieno[2,3-d]pyridyl group, a benzpyranyl group, a tetrahydrofuryl group, a tetrahydropyranyl group, a dioxoranyl group, a dioxanyl group, etc. are used.

These heterocyclic groups may be substituted at possible positions by 1 to 3 substituents selected from $C_{1-4}$ alkyl (e.g., methyl, ethyl, etc.), hydroxy, oxo, $C_{1-4}$ alkoxy (e.g., methoxy, ethoxy, etc.), etc.

As the "aromatic hydrocarbon group" of the "aromatic hydrocarbon group optionally having substituents" (optionally substituted aromatic hydrocarbon group) represented by Ar, $Ar^a$, for example, an aromatic hydrocarbon group having 6 to 14 carbon atoms (e.g., a phenyl group, a naphthyl group, a biphenyl group, an anthryl group, an indenyl group and the like) and the like, and particularly an aryl group having 6 to 10 carbon atoms and the like (e.g., phenyl and naphthyl groups) are preferred and a phenyl group and the like are particularly preferred.

As the "substituent" of the "aromatic hydrocarbon group optionally having substituents" represented by Ar, $Ar^a$, for example, a halogen atom (e.g., fluorine, chlorine, bromine, iodine and the like), a lower ($C_{1-4}$) alkyl group (e.g., a methyl group, an ethyl group, a propyl group, a butyl group and the like), a lower ($C_{1-4}$) alkoxy group (e.g., a methoxy group, an ethoxy group, a propoxy group, a butoxy group and the like), a lower ($C_{1-4}$) alkoxycarbonyl group (e.g., a methoxycarbonyl group, an ethoxycarbonyl group, a propoxycarbonyl group, a butoxycarbonyl group and the like), a carboxyl group, a nitro group, a cyano group, a hydroxyl group, an acylamino group (e.g., an alkanoylamino group having 1 to 4 carbon atoms such as an acetylamino group, a propyonylamino group, a butyrylamino group and the like), a cycloalkyl group having 3 to 6 carbon atoms (e.g., a cyclopropyl group, a cyclopentyl group and the like), an aryl group having 6 to 10 carbon atoms (e.g., a phenyl group, a naphthyl group, an indenyl group and the like), a halogeno-lower ($C_{1-4}$) alkyl group (e.g., a trifluoromethyl group, a trifluoroethyl group and the like), a halogeno-lower ($C_{1-4}$) alkoxy group (e.g., a trifluoromethoxy group, a 1,1,2,2-tetrafluoroethoxy group, a 2,2,3,3,3-pentafluoropropoxy group and the like), a lower ($C_{1-4}$) alkylthio group (e.g., a methylthio group, an ethylthio group, a propionylthio group and the like), a lower ($C_{1-4}$) alkylsulfonyl group (e.g., a methanesulfonyl group, an ethanesulfonyl group, a propanesulfonyl group and the like), a lower ($C_{1-4}$) alkanoyl group (e.g., a formyl group, an acetyl group, a propionyl group and the like), a 5-membered aromatic heterocyclic group (e.g., a 1,2,3-triazolyl group, a 1,2,4-triazolyl group, a tetrazolyl group, a thiazolyl group, an isothiazolyl group, an oxazolyl group, an isooxyazolyl group, a thiadiazolyl group, a thienyl group, a furyl group and the like), a carbamoyl group, a lower ($C_{1-4}$) alkyl-carbamoyl group (e.g., a methylcarbamoyl group, a dimethylcarbamoyl group, a propionylcarbamoyl group and the like), a lower ($C_{1-4}$) alkoxy-carbonyl-lower ($C_{1-4}$) alkyl-carbamoyl group (e.g., a butoxycarbonylmethylcarbamoyl group, an ethoxycarbonylmethylcarbamoyl group and the like), a 1,3-diacylguanidino-lower ($C_{1-4}$) alkyl group and the like (e.g., 1,3-diacetylguanidinomethyl, 1,3-bis-t-butoxycarbonylguanidinomethyl and the like) are used, and a halogen atom (e.g., fluorine, chlorine, bromine, iodine atoms and the like), a lower ($C_{1-4}$) alkyl group and the like (e.g., a methyl group, an ethyl group, a propyl group, a butyl group and the like) are preferably used, and a fluorine atom, a chlorine atom and a methyl group are more preferably used.

These substituents are substituted at substitutable positions in the aromatic hydrocarbon group, and the number of the substituents is preferably 1 to 5, more preferably 1 to 3, most preferably 1 to 2. When two or more of such substituents are present, they may be the same or different.

Typically, as Ar or $Ar^a$, for example, a phenyl group, a halogenophenyl group, a lower ($C_{1-4}$) alkylphenyl group, a lower ($C_{1-4}$) alkoxyphenyl group, a lower ($C_{1-4}$) alkoxycarbonylphenyl group, a carboxylphenyl group, a nitrophenyl group, a cyanophenyl group, a halogeno-lower ($C_{1-4}$) alkylphenyl group, a halogeno-lower ($C_{1-4}$) alkoxyphenyl group, a lower ($C_{1-4}$) alkanoylphenyl group, a 5-membered aromatic heterocycle-substituted phenyl group, a lower ($C_{1-4}$) alkoxy-carbonyl-lower ($C_{1-4}$) alkyl-carbamoylphenyl group, 1,3-diacylguanidino-lower ($C_{1-4}$) alkylphenyl group, a halogen- and lower ($C_{1-4}$) alkoxy-substituted phenyl group, a halogen- and lower ($C_{1-4}$) alkoxycarbonyl-substituted phenyl group, a halogen- and cyano-substituted phenyl group, a halogen- and 5-membered aromatic heterocycle-substituted phenyl group, a halogen- and lower ($C_{1-4}$) alkoxycarbonyl-lower ($C_{1-4}$) alkyl-carbamoyl-substituted phenyl group and the like are used.

As Ar or $Ar^a$, a halogenophenyl group, a lower ($C_{1-4}$) alkylphenyl group, a halogen- and lower ($C_{1-4}$) alkoxycarbonyl-substituted phenyl group and the like are preferably used.

As Ar or $Ar^a$, a group represented by formula:

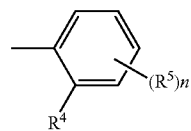

wherein $R^4$ and $R^5$ is the same or different and each represents a halogen atom or a lower alkyl group, and n is an integer of 0 to 2, with one in which at least one of $R^4$ and $R^5$ is a halogen atom being further preferred.

As the halogen atom represented by $R^4$ and $R^5$, a fluorine atom or a chlorine atom is preferred.

As the halogenophenyl group, for example, a 2,3-difluorophenyl group, a 2,3-dichlorophenyl group, a 2,4-difluorophenyl group, a 2,4-dichlorophenyl group, a 2,5-difluorophenyl group, a 2,5-dichlorophenyl group, a 2,6-difluorophenyl group, a 2,6-dichlorophenyl group, a 3,4-difluorophenyl group, a 3,4-dichlorophenyl group, a 3,5-difluorophenyl group, a 3,5-dichlorphenyl group, a 2-fluorophenyl group, a 2-chlorophenyl group, a 3-fluorophenyl group, a 3-chlorophenyl group, a 4-fluorophenyl group, a 4-chlorophenyl group, a 2-fluoro-4-chlorophenyl group, a 2-chloro-4-fluorophenyl group, a 4-bromo-2-fluorophenyl group, a 2,3,4-trifluorophenyl group, a 2,4,5-trifluorophenyl group, a 2,4,6-trifluorohenyl group and the like are used.

As the lower ($C_{1-4}$) alkylphenyl group, a 2-ethylphenyl group, a 2,6-diisopropylphenyl group and the like are preferably used, and as the lower ($C_{1-4}$) alkoxyphenyl group, for example, a 4-methoxyphenyl group and the like are preferably used.

As the lower ($C_{1-4}$) alkoxy-carbonylphenyl group, a 2-ethoxycarbonylphenyl group, a 2-methoxycarbonylphenyl group, a 4-methoxycarbonylphenyl group and the like are preferably used, and as the halogeno-lower ($C_{1-4}$) alkylphenyl group, for example, a 2-trifluoromethylphenyl group and the like are preferably used, and as the halogeno-lower ($C_{1-4}$) alkoxyphenyl group, a 2-trifluoromethoxyphenyl group, a 4-(2,2,3,3,3-pentafluoropropoxy)phenyl group and the like are preferably used.

As the lower ($C_{1-4}$) alkanoylphenyl group, for example, a 2-acetylphenyl group and the like are preferably used, and as the 5-membered aromatic heterocycle-substituted phenyl, for example, a 4-(2H-1,2,3-triazol-2-yl)phenyl group, a 4-(2H-tetrazol-2-yl)phenyl group, a 4-(1H-tetrazol-1-yl)phenyl group, a 4-(1H-1,2,3-triazol-1-yl)phenyl group and the like are preferably used, and as the lower ($C_{1-4}$) alkoxy-carbonyl-lower ($C_{1-4}$) alkyl-carbamoylphenyl group, for example, a 4-(N-ethoxycarbonylmethylcarbamoyl) phenyl group and the like are preferably used, and as the 1,3-diacylguanidino-lower ($C_{1-4}$) alkylphenyl group, for example, a 4-(1,3-bis-t-butoxycarbonylguanidinomethyl)phenyl group and the like are preferably used.

As the phenyl group substituted by halogen and lower ($C_{1-4}$) alkyl, for example, a 2-fluoro-4-methylphenyl group, a 2-chloro-4-methylphenyl group, a 4-fluoro-2-methylphenyl group and the like are preferably used, and as the phenyl group substituted by halogen and lower ($C_{1-4}$) alkoxycarbonyl, for example, a 2-chloro-4-methoxycarbonylphenyl group and the like are preferably used, and the phenyl group substituted by halogen and cyano, for example, a 2-chloro-4-cyanophenyl group and the like are preferably used, and as the phenyl group substituted by halogen and 5-membered aromatic heterocycle, for example, a 2-fluoro-4-(1H-1,2,4-triazol-1-yl)phenyl group and the like are preferably used, and as the phenyl group substituted by halogen and lower ($C_{1-4}$) alkoxycarbonyl-lower ($C_{1-4}$) alky-carbamoyl, for example, a 2-chloro-4-(N-t-butoxycarbonylmethylcarbamoyl)phenyl group, a 2-chloro-4-(N-ethoxycarbonylmethylcarbamoyl) phenyl group and the like are preferably used.

More specifically, as Ar or $Ar^a$, a phenyl group, a phenyl group substituted with 1 to 3 (particularly 1 to 2) halogen atoms (e.g., a 2,3-difluorophenyl group, a 2,3-dichlorophenyl group, a 2,4-difluorophenyl group, a 2,4-dichlorophenyl group, a 2,5-difluorophenyl group, a 2,5-dichlorophenyl group, a 2,6-difluorophenyl group, a 2,6-dichlorophenyl group, a 3,4-difluorophenyl group, a 3,4-dichlorophenyl group, a 3,5-difluorophenyl group, a 3,5-dichlorophenyl group, a 4-bromo-2-fluorophenyl group, a 2-fluorophenyl group, a 2-chlorophenyl group, a 3-fluorophenyl group, a 3-chlorophenyl group, a 4-fluorophenyl group, a 4-chlorophenyl group, a 2-fluoro-4-chlorophenyl group, a 2-chloro-4-fluorophenyl group, a 2,3,4-trifluorophenyl group, a 2,4,5-trifluorophenyl group and the like), a phenyl group substituted by halogen and lower ($C_{1-4}$) alkyl (e.g., a 2-chloro-4-methylphenyl group, a 4-fluoro-2-methylphenyl group and the like), etc. are preferred. Of them, a phenyl group substituted with 1 to 3 (particularly 1 to 2) halogen atoms (e.g., a 2,3-dichlorophenyl group, a 2,4-difluorophenyl group, a 2,4-dichlorophenyl group, a 2,6-diclorophenyl group, a 2-fluorophenyl group, a 2-chlorophenyl group, a 3-chlorophenyl group, a 2-chloro-4-fluorophenyl group, a 2,4,5-trifluorophenyl group and the like), a phenyl group substituted by halogen and lower ($Cl_4$) alkyl (e.g., a 2-chloro-4-methylphenyl group, a 4-fluoro-2-methylphenyl group and the like), etc. are preferred. Particularly, a 2,4-difluorophenyl group, a 2-chlorophenyl group, a 2-chloro-4-fluorophenyl group, a 2-chloro-4-methylphenyl group and the like are preferred, and a 2,4-difluorophenyl group, a 2-chloro-4-fluorophenyl group and the like are preferred.

In this specification, the ring $A^1$ represents a cycloalkene optionally substituted by 1 to 4 substituents selected from the group consisting of (i) an aliphatic hydrocarbon group optionally having substituents, (ii) an aromatic hydrocarbon group optionally having substituents, (iii) a group represented by formula $OR^1$ (wherein $R^1$ is as defined above) and (iv) a halogen atom and a cycloalkene optionally substituted by 1 to 4 substituents selected from the group consisting of (i) an aliphatic hydrocarbon group optionally having substituents, (ii) an aromatic hydrocarbon group optionally having substituents and (iv) a halogen atom are preferred.

In this specification, the ring $A^2$ represents a cycloalkene substituted by 1 to 4 substituents selected from the group consisting of (i) an aliphatic hydrocarbon group optionally having substituents, (ii) an aromatic hydrocarbon group optionally having substituents, (iii) a group represented by formula $OR^1$ (wherein $R^1$ is as defined above) and (iv) a halogen atom, and a cycloalkene substituted by 1 to 4 substituents selected from the group consisting of (i) an aliphatic hydrocarbon group optionally having substituents, (ii) an aromatic hydrocarbon group optionally having substituents and (iv) a halogen atom are preferred.

These substituents are substituted on substitutable carbon atoms in a ring $A^1$ or ring $A^2$, and when the ring $A^1$ or $A^2$ is substituted by two or more of such substituents, the substituents may be the same or different. A single carbon atom may be substituted by two substituents and different carbon atoms may be substituted by two or more substituents.

As the "aliphatic hydrocarbon group optionally having substituents" as a substituent on the ring $A^1$ and ring $A^2$, for example, the same substituents as the "aliphatic hydrocarbon group optionally having substituents" represented by R, $R^1$, $R^{1a}$, $R^{1b}$, $R^{1c}$ described above may be used.

As the "aromatic hydrocarbon group optionally having substituents" as a substituent on the ring $A^1$ and ring $A^2$, for example, the same substiuents as the "aromatic hydrocarbon group optionally having substituents" represented by Ar or $Ar^a$ described above may be used.

As the "heterocyclic group optionally having substituents" as a substituent on the ring $A^1$ and ring $A^2$, for example, the same substiuents as the "heterocyclic group" which is a substituent on the "aliphatic hydrocarbon group optionally having substituents" represented by R, $R^1$, $R^{1a}$, $R^{1b}$, $R^{1c}$.

As the substituents for the ring $A^1$ and ring $A^2$, 1 or 2 $C_{1-6}$ alkyl group (e.g., a $C_{1-4}$ alkyl group such as a methyl group, a tert-butyl group, etc.), a phenyl group, a halogen atom (e.g., fluorine, chlorine, bromine, iodine, etc.), etc. are preferably used.

The group represented by the formula:

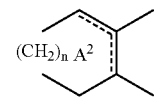

wherein n represents the same meaning as defined above, can be a group represented by the formula:

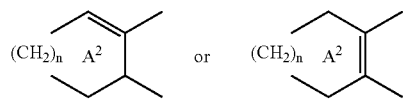

wherein n represents the same meaning as defined above, and preferably a group represented by the formula:

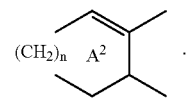

The group represented by the formula:

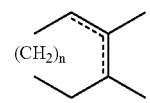

wherein n represents the same meaning as defined above, can be a group represented by the formula:

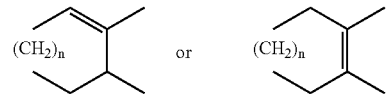

wherein n represents the same meaning as defined above, and preferably a group represented by the formula:

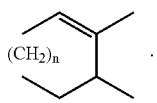

And, the group represented by the formula:

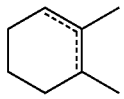

can be a group represented by the formula:

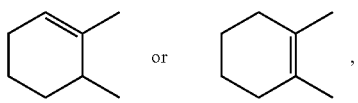

and preferably a group represented by the formula:

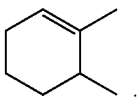

As the integer of 1 to 4 represented by n, 1 to 3 is preferred and 2 is more preferred.

As the compound represented by the formula (Iaa), the compound represented by the formula (Ibb) is preferred, and as the compound represented by the formula (Ia), the compound represented by the formula (Ib) is preferred.

As the compound represented by the formula (Ibb), the compound represented by the formula (Inn) is preferred, and as the compound represented by the formula (Ib), the compound represented by the formula (In) is preferred.

As the compound (Ibb), (Ib), a compound wherein $R^1$ is a lower alkyl group optionally having substituents, $R^2$ is a hydrogen atom or a lower alkyl group, Ar is a phenyl group optionally having substituents, n is 1, 2 or 3 is preferred, and a compound wherein $R^1$ is a lower alkyl group optionally having substituents, $R^2$ is a hydrogen atom, Ar is a phenyl group substituted by a halogen atom, n is 2 is more preferred, As the compound represented by the formula (Icc), (Ic), a compound wherein Ar is a phenyl group optionally having substituents, n is 2 is preferred.

As the leaving group represented by $X^1$, for example, a halogen atom (e.g., chlorine, bromine, iodine, etc.), etc. are preferred and a chlorine atom is more preferred.

When the compounds represented by formulae (I), (Iaa), (Ibb), (Icc), (Ia), (Ib), (Ic), (Id), (Ie), (If) and (Ig) have stereoisomers, any of such stereoisomers and mixtures thereof are included in the invention.

When a compound represented by formula (Iaa) is a compound represented by formula (Icc) or (Inn), when a compound represented by formula (Ia) is a compound represented by formula (Ic) or (In), when a compound represented by formula (Ie) is a compound represented by formula (Ik) or (Ip), when a compound represented by formula (Id) is a compound represented by formula (Ir), and when a compound represented by formula (Ig) is a compound represented by formula (It), then each compound can exist as an optical isomer with regard to the asymmetric carbon atom in a cycloalkene or cyclohexene ring, and any of such optical isomers and mixtures thereof are included in the invention.

A compound represented by formula (I) or (Ia) may preferably be d-ethyl 6-[N-(2,4-difluorophenyl)sulfamoyl]-1-cyclohexene-1-carboxylate, ethyl 6-[N-(2-chlorophenyl)sulfamoyl]-1-cyclohexene-1-carboxylate, ethyl 6-[N-(2-chloro-4-methylphenyl)sulfamoyl]-1-cyclohexene-1-carboxylate or d-ethyl 6-[N-(2-chloro-4-fluorophenyl)sulfamoyl]-1-cyclohexene-1-carboxylate as well as a salt thereof.

The compounds (I), (Iaa), (Ia), (Ib), (Ic), (Id), (Ie), (If), (Ig), (Ibb) and (Icc) (hereinafter simply referred to as an inventive Compound) may, for example, be converted into a salt with an inorganic base, organic base, inorganic acid, organic acid, basic or acidic amino acid. A salt with an inorganic base may, for example, be an alkaline metal salt such as sodium and potassium salts, an alkaline earth metal salt such as calcium and magnesium salts, aluminum and ammonium salts, and a salt with an organic base may, for example, be a salt with trimethylamine, triethylamine, pyridine, picoline, ethanolamine, diethanolamine, triethanolamine, dicyclohexylamine or N,N'-dibenzylethylenediamine. A salt with an inorganic acid may, for example, be a salt with hydrochloric acid, hydrobromic acid, nitric acid, sulfuric acid or phosphoric acid, and a salt with an organic acid may, for example, be a salt with formic acid, acetic acid, trifluoroacetic acid, fumaric acid, oxalic acid, tartaric acid, maleic acid, citric acid, succinic acid, malic acid, methanesulfonic acid, benzenesulfonic acid or p-toluenesulfonic acid. A salt with a basic amino acid may, for example, be a salt with arginine, lysine or ornithine, and a salt with acidic amino acid may, for example, be a salt with aspartic acid or glutamic acid.

A prodrug for an inventive Compound or a salt thereof is a compound which is converted into an inventive Compound under a physiological condition as a result of a reaction with an enzyme or gastric acid, thus a compound undergoing an enzymatic oxidation, reduction or hydrolyzation to form an inventive Compound and a compound hydrolyzed by gastric acid to form an inventive Compound. A prodrug for an inventive Compound may, for example, be a compound obtained by subjecting an amino group in an inventive Compound to an acylation, alkylation or phosphorylation (e.g., a compound obtained by subjecting an amino group in an inventive Compound to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation); a compound obtained by subjecting a hydroxy group in an inventive Compound to an acylation, alkylation, phosphorylation and boration (e.g., a compound obtained by subjecting a hydroxy group in an inventive Compound to an acetylation, palmitoylation, propanoylation, pivaloylation, succinylation, fumarylation, alanylation and dimethylaminomethylcarbonylation); a compound obtained by subjecting a carboxyl group in an inventive Compound to an esterification or amidation (e.g, a compound obtained by subjecting a carboxyl group in an inventive Compound to an ethylesterification, phenylesterification, carboxymethylesterification, dimethylaminomethylesterification, pivaloyloxymethylesterification, ethoxycarbonyloxyethylesterification, phthalidylesterification, (5-methyl-2-oxo-1,3-dioxolen-4-yl)methylesterification, cyclohexyloxycarbonylethylesterification and methylamidation) and the like. Any of these and other precursor or derivative compounds can be produced from the inventive Compound.

A prodrug for an inventive Compound may also be one which is converted into an inventive Compound under a physiological condition, such as those described in "IYAKU-HIN no KAIHATSU (Development of Pharmaceuticals)", Vol.7, Design of Molecules, p. 163-198, Published by HIROKAWA SHOTEN (1990).

The inventive Compound, a salt thereof and a prodrug therefor can be produced according to a method known per se, for example, a production method described in WO99/46242 or a method analogous thereto.

The inventive Compound, a salt thereof and a prodrug therefor may be a hydrate or non-hydrate.

The inventive Compound, a salt thereof and a prodrug therefor may be labeled with an isotope (e.g., $^3$H, $^{14}$C, $^{35}$S, $^{125}$I etc.) and the like.

According to the composition of the present invention, the inventive Compound, a salt thereof and a prodrug therefor having poor water solubility can be used effectively as a component of the composition constituted by an emulsifier.

The inventive Compound, a salt thereof and a prodrug therefor may exist in a state of a liquid or solid in an oil phase, and the composition of the present invention is an oil-in-water (O/W type) or S/O/W type emulsion composition.

The composition of the present invention can be produced using an anionic synthetic phospholipid and a naturally-occurring phospholipid.

The composition of the present invention consists of disperse phase particles containing an anionic synthetic phospholipid, a naturally-occurring phospholipid, an oil component and the inventive Compound, a salt thereof or a prodrug therefor, and water in which the disperse phase particles are dispersed.

As the anionic synthetic phospholipid, an anionic phospholipid wherein two chain hydrocarbon groups in a phospholipid molecule is constituted by a single molecule consisting of one or two kinds of fatty acids, and the like are used. An anionic synthetic phospholipid of the invention is characterized as a mostly homogeneous population of anionic phospholipid molecules having two hydrocarbon chains. The two hydrocarbon chains of the anionic phospholipid molecules are hydrocarbon chains (ie. fatty acids) that may be the same or different species of hydrocarbon chain. Each anionic phospholipid molecule may have two of the same fatty acid chains, or two different fatty acid chains. In the case of a synthetic anionic phospholipid of the invention with each phospholipid molecule having two different fatty acid chains, the order of chains proximal to the phosphate bound carbon is not critical and can vary within the population of mostly homogeneous molecules.

Specific examples of the anionic synthetic phospholipid include a group of the formula

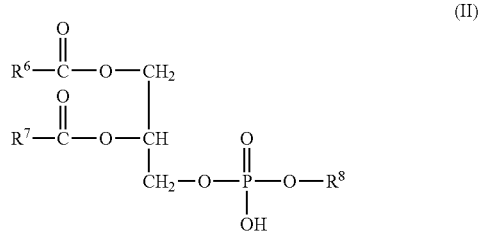

(II)

wherein $R^6$ and $R^7$ are the same or different and each is a $C_{7-20}$ chain hydrocarbon group, and $R^8$ is

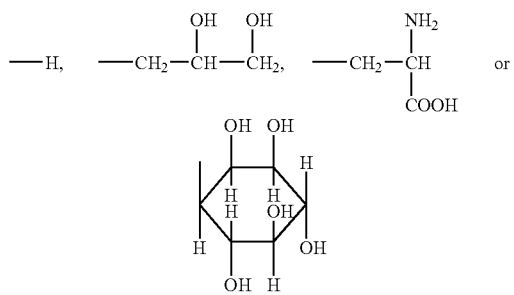

or a salt thereof and the like can be used.

The $C_{7-20}$ chain hydrocarbon group represented by $R^6$ and $R^7$ may be, for example, $C_{7-20}$ alkyl group, $C_{7-20}$ alkenyl group and the like, and $C_{7-20}$ alkyl group is particularly preferable. Furthermore, $C_{10-20}$ alkyl group is preferable, and particularly $C_{12-18}$ alkyl group is preferable.

As the anionic synthetic phospholipid, a group of the formula

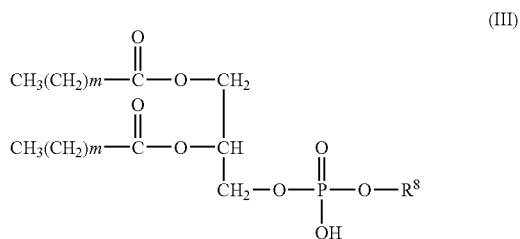

(III)

wherein m is an integer of 7-20, and $R^8$ is

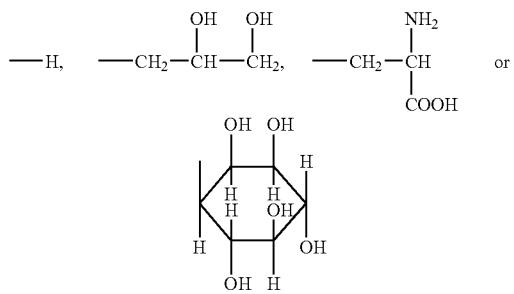

is preferable.

The m is preferably an integer of 10-20, and is particularly preferably an integer of 12-18.

The compounds (II) and (III) can be converted to a salt with an inorganic base, a salt with an organic base, a salt with a basic amino acid and the like. A salt with an inorganic base may, for example, be an alkaline metal salt such as sodium and potassium salts, an alkaline earth metal salt such as calcium and magnesium salts, aluminum and ammonium salts, and a salt with an organic base may, for example, be a salt with trimethylamine, triethylamine, pyridine, picoline, ethanolamine, diethanolamine, triethanolamine, dicyclohexylamine or N,N'-dibenzylethylenediamine. A salt with a basic amino acid may, for example, be a salt with arginine, lysine or ornitine. Of these, alkali metal salts such as sodium salt are particularly preferable.

More specifically, the anionic synthetic phospholipid may be, for example, an anionic synthetic phospholipid such as dimyristoylphosphatidylglycerol, dipalmitoylphosphatidylglycerol, distearoylphosphatidylglycerol, dioleoylphosphatidylglycerol, oleoylpalmitoylphosphatidylglycerol, dioctanoylphosphatidic acid, didecanoylphosphatidic acid, dilauroylphosphatidic acid, dimyristoylphosphatidic acid, dipalmitoylphosphatidic acid, diheptadecanoylphosphatidic acid, distearoylphosphatidic acid, dioleoylphosphatidic acid, arachidonylstearoylphosphatidic acid, dipalmitoylphosphatidylserine, dioleoylphosphatidylserine, dimyristoylphosphatidylinositol, dipalmitoylphosphatidylinositol, distearoylphosphatidylinositol, dioleoylphosphatidylinositol, dimyristoylphosphatidylserine, distearoylphosphatidylserine and the like, particularly preferably dimyristoylphosphatidylglycerol.

The anionic synthetic phospholipid can be used alone or as a mixture of two or more kinds thereof.

These anionic synthetic phospholipids can be chemically synthesized according to a method known per se or may be obtained by purification. It is also possible to use a commercially available anionic synthetic phospholipid.

The naturally-occurring phospholipid is a phospholipid mixture containing a pluralality (for example, two or more kinds) of molecular species depending on the composition of the fatty acid constituting the fatty acid ester. Naturally-occurring phospholipid is a heterogeneous mixture of phospholipids containing two or more molecular species of phospholipid as distinguished by the fatty ester component of the respective fatty acid chains.

Specifically, as the naturally-occurring phospholipid, for example, phospholipid obtained from natural products by purification, extraction and the like (e.g., non-anionic phospholipids such as egg yolk lecithin, soybean lecithin, phosphatidylcholine and the like), a hydrogenation composition of these and the like are used, preferably egg yolk lecithin. Particularly preferred is purified egg yolk lecithin capable of intravenous administration, which is described in the pharmaceutical product additive standard and the like.

It is also possible to use a non-ionic surfactant as an emulsifier instead of the naturally-occurring phospholipid or along with the naturally-occurring phospholipid.

The non-ionic surfactant is exemplified by polymer surfactants having a molecular weight of about 800-20000, such as polyoxyethylene-polyoxypropylene copolymer, polyoxyethylene alkyl ether, polyoxyethylene alkyl aryl ether, hydrogenated castor oilpolyoxyethylene derivative, polyoxyethylene sorbitan derivative, polyoxyethylene sorbitol derivative, polyoxyethylene alkyl ether sulfate and the like.

The naturally-occurring phospholipid and the non-ionic surfactant as an emulsifier can be used singly or in combination.

The composition of the present invention contains an anionic synthetic phospholipid in a proportion of about 0.0001-about 5%(W/V), preferably about 0.2%(W/V), of the entire composition. More specifically, the amount of the anionic synthetic phospholipid is desirably set to fall within the following ranges.

(1) approximately about 0.0001-about 5% (W/V)
(2) approximately about 0.0001-about 2% (W/V)
(3) approximately about 0.0001-about 0.5% (W/V)
(4) approximately about 0.0001-about 0.2% (W/V),
(5) approximately about 0.0001-0.17% (W/V)
(6) approximately about 0.0001-0.15% (W/V)
(7) approximately about 0.0001-0.125% (W/V)
(8) approximately about 0.0001-0.1% (W/V)
(9) approximately about 0.0001-less than about 0.02% (w/v) (preferably 0.0001-0.09% (W/V))
(10) approximately about 0.0001-about 0.08%(W/V)
(11) approximately about 0.0001-about 0.07%(W/V)
(12) approximately about 0.0001-about 0.05%(W/V)
(13) approximately about 0.0001-about 0.03%(W/V)
(14) approximately about 0.0001-about 0.02%(W/V)
(15) approximately about 0.0001-less than about 0.02% (W/V) (preferably 0.001-0.019% (W/V))
(16) approximately about 0.0001-0.015% (W/V)
(17) approximately about 0.0001-0.01% (W/V)
(18) approximately about 0.0001-0.009% (W/V)
(19) approximately about 0.0001-0.007% (W/V)
(20) approximately about 0.0001-0.005% (W/V)
(21) approximately about 0.0001-0.003% (W/V)
(22) approximately about 0.0001-0.001% (W/V)

In the above-mentioned (1)-(22), the lower limit may be set to not less than about 0.0005%, and in the above-mentioned (1)-(21), the lower limit may be set to not less than about 0.001%.

It is also possible to use the anionic synthetic phospholipid in a proportion of not less than about 5% (W/V) (for example, about 5-about 10%(W/V)), relative to the entire composition of the present invention.

The composition of the present invention contains a naturally-occurring phospholipid in a proportion of generally about 0.1-about 10% (W/V), preferably about 0.2-about 7% (W/V), more preferably about 0.5-about 5% (W/V), relative to the entire composition.

When a non-ionic surfactant is used as an emulsifier, the total amount of the naturally-occurring phospholipid and the non-ionic surfactant relative to the entire composition of the present invention is generally about 0.1-about 10% (W/V), preferably about 0.2-about 7% (W/V), more preferably about 0.5-about 5% (W/V).

In the composition of the present invention, the proportion of the total amount of the anionic synthetic phospholipid, naturally-occurring phospholipid and the non-ionic surfactant (hereinafter sometimes to be briefly referred to as an emulsifier) relative to the oil component is, for example, about 0.1-about 150 wt %, preferably about 0.5-about 125 wt %, more preferably about 1-about 100 wt %. The emulsifier is often used in a proportion of generally about 1-about 15 wt %, particularly about 1-about 10 wt %, relative to the an oil component.

By specifying the amounts of the anionic synthetic phospholipid and the naturally-occurring phospholipid to be used, the stability of the inventive Compound, a salt thereof and a prodrug therefor, and the composition of the present invention can be further improved.

As the oil component, any pharmaceutically acceptable fats and oils generally used for the preparation of fat emulsion in the field of pharmaceutical technology. Examples of the fats and oils include vegetable oil, fats and oils obtainable by partial hydrogenation of vegetable oils, oils obtainable by transesterification (simple glycerides and mixed glycerides), and glycerol esters of medium chain fatty acids.

The aforementioned fats and oils include, for example, a glycerol ester of a fatty acid having about 6 to 30 carbon atoms, preferably about 6 to 22 carbon atoms. Examples of the aforementioned fatty acid include saturated fatty acids such as caproic acid, caprylic acid, capric acid, lauric acid, myristic acid, palmitic acid, stearic acid, behenic acid and the like; unsaturated fatty acids such as palmitooleic acid, oleic acid, linoleic acid, arachidonic acid, icosapentaenoic acid, docosahexaenoic acid and the like.

Preferred examples of the oil component include vegetable oils such as soybean oil, cottonseed oil, rapeseed oil, peanut oil, safflower oil, sesame oil, rice bran oil, corn germ oil, sunflower oil, poppy oil, olive oil and the like. Of these vegetable oils, soybean oil and the like are preferably used. Particularly preferably, soybean oil that can be administered intravenously and described in Japan Pharmacopoeia, USP, EP, BP and the like is used.

As the fats and oils, triglyceride of a medium chain fatty acid having about 6 to 14 carbon atoms, preferably about 8 to 12 carbon atoms, can be also used. Preferable glycerine ester of a medium chain fatty acid is, for example, "Migriol 810" and "Migriol 812" (both trade names, manufactured by Huls Co., Ltd., available from Mitsuba Trading Co., Ltd.), a glyceryl tricaprylate (tricaprylin) such as "Panasate 800" (trade name, manufactured by NOF Corporation, Japan, and the ike.

The composition of the present invention contains an oil component in a proportion of, for example, about 1 to about 30 wt % by weight, preferably about 2 to about 25 wt %, and more preferably about 2.5 to about 22.5 wt %, of the entire composition.

The composition of the present invention can be prepared by mixing a disperse phase consisting of the inventive Compound, a salt thereof and a prodrug therefor (main drug), the oil component and emulsier, and water. Where necessary, a stabilizer for improving the stability of the aforementioned main drug, an isotonic agent for adjusting the osmotic pressure, an emulsifying-auxiliaries to enhance emulsifying capability, an emulsification stabilizer for enhancing the stability of the emulsifier and the like may be added.

Examples of the stabilizer include, for example, antioxidants (for example, ascorbic acid, tocopherol, sorbic acid, retinol and the like), chelating agents (for example, citric acid, tartaric acid and the like) and the like. The stabilizer is used in an amount of generally about 0.00001-about 10% (W/V), preferably about 0.0001-about 5% (W/V), relative to the entire composition of the present invention.

The isotonic agent includes, for example, glycerol, sugar alcohols, monosaccharides, disaccharides, amino acid, dextran, albumin and the like. These isotonic agents may be use singly or in combination.

Examples of the emulsifying-auxiliaries include fatty acids having about 6 to 30 carbon atoms, salts of these fatty acids, monoglycerides of the fatty acids. Examples of the aforementioned fatty acid include caproic acid, caprylic acid, capric acid, lauric acid, myristic acid, palmitic acid, stearic acid, behenic acid, palmitooleic acid, oleic acid, linolic acid, arachidonic acid, icosapentaenoic acid, docosahexaenoic acid and the like. Examples of the salts of include alkali metal salts such as sodium salt and potassium salt, calcium salt and the like.

Examples of the emulsifying stabilizer include cholesterol, cholesterol esters, tocopherol, albumin, fatty acid amide derivatives, polysaccharides, derivatives of fatty acid esters of polysaccharides and the like.

The concentration of the inventive Compound, a salt thereof or a prodrug therefor in the composition of the present invention varies depending on the pharmacological activities or kinetics in blood of the compound, and is usually about 0.001-about 5% (W/V), preferably about 0.01-about 2% (W/V), more preferably about 0.1-about 0.5% (W/V). It is also possible to set the content of the inventive Compound, a salt thereof or a prodrug therefor in the composition of the present invention to about 1-about 5000 mg, preferably about 10-about 2000 mg, more preferably about 100-about 1000 mg, per 100 ml of the composition. Furthermore, the content of the inventive Compound, a salt thereof or a prodrug therefor in the composition of the present invention can be adjusted to about 0.001-about 95 wt %, preferably about 0.01-about 30 wt %, more preferably about 0.1-about 3 wt %, based on the total volume of the composition.

The proportion (wt %) of the inventive Compound, a salt thereof or a prodrug therefor relative to the disperse phase comprising an oil component and an emulsifier is generally about 0.0047-about 24%, preferably about 0.047-about 9.4%, more preferably about 0.47-about 2.4%.

The composition of the present invention is adjusted to have a pH of not more than about 6, more specifically about 3-about 6, preferably about 3-about 5.5, more preferably about 3-about 5, still more preferably about 3-about 4.5.

The pH adjusting agent is exemplified by phosphoric acid, carbonic acid, citric acid, hydrochloric acid, sodium hydroxide and the like, with particular preference given to hydrochloric acid, sodium hydroxide and the like.

The composition of the present invention is preferably used as, for example, an injectable composition.

The composition of the present invention can be produced principally according to a known method or a method analogous thereto. The emulsification can be conducted in a conventional emulsifying technique. It is preferable to disperse or dissolve the inventive Compound, a salt thereof and a prodrug therefor in an oil component beforehand. For example, a mixture of (1) a disperse phase containing the oil component and the emulsifier, and (2) the inventive Compound, a salt thereof and a prodrug therefor is dispersed in water to give a composition consisting of an O/W type or S/O/W type emulsion.

Preferred examples of the method include a method comprising homogenizing a heterogeneous mixture containing a mixture of the main drug, an oil component, an emulsifier, and where necessary, an additive such as an isotonic agent and the like and water in the aforementioned emulsifying apparatus to give a roughly emulsified emulsion, followed by, if necessary, adding water, further homogenizing the resultant rough emulsion using an emulsifying apparatus and removing large particles by a filtering means such as a filter and the like to give an oil-in-water composition. The aforementioned mixture is generally heated to, for example, about 30-about 90° C., preferably about 40-about 80° C. to dissolve or disperse the main drug. Examples of the emulsifying apparatus for the emulsification of the heterogeneous mixture containing the aforementioned mixture and water include a conventional apparatus such as a homogenizer including a pressure jetting homogenizer, an ultrasonic homogenizer and the like, and a homomixer such as a high-rate mixer and the like. For removing large particles having a particle size of not less than about 5 μm, preferably not less than about 1 μm, more preferably not less than about 0.5 μm, the homogenized emulsion is frequently subjected to a filtering means such as a filter.

In the composition of the present invention, the mean particle size of the disperse phase wherein the inventive Compound, a salt thereof or a prodrug therefor is dissolved, is, for example, mostly about 0.01-about 5 μm (about 10-about 5000 nm), preferably about 0.02-about 1 μm (about 20-about 1000 nm), more preferably about 0.03-about 0.5 μm (about 30-about 500 nm).

In view of the stability of the composition of the present invention and biodistribution after administration, the mean particle size in the disperse phase wherein the inventive Compound, a salt thereof or a prodrug therefor is dissolved, is, for example, about 25-about 500 nm, preferably about 50-about 300 nm, more preferably about 100-about 300 nm (particularly about 150-about 260 nm).

A pyrogen can be removed from the composition of the present invention according to a method known per se.

The composition of the present invention is subjected to nitrogen gas displacement, sterilized and sealed as necessary.

Since the composition of the present invention has a pH adjusted to not more than about 6, the inventive Compound, a salt thereof and a prodrug therefor, as well as the composition of the present invention show superior stability even after sterilization in an autoclave etc. Particularly, because the composition of the present invention contains the anionic synthetic phospholipid and the naturally-occurring phospholipid in specific proportions, more superior stability can be maintained.

In the composition of the present invention, moreover, the concentration of the inventive Compound, a salt thereof and a prodrug therefor can be increased. By controlling the particle size of the disperse phase particle, retentivity in blood, blood vessel permeability and migration performance into inflammatory site can be enhanced. Therefore, the pharmacokinetics and biodistribution of the inventive Compound, a salt thereof and a prodrug therefor can be improved, thereby enabling targeting, which in turn leads to more effective administration of a drug with less side effect. Thus, the composition of the present invention is useful for the treatment of target disease particularly by an intravenous administration.

Since an inventive Compound, a salt thereof and a prodrug therefor have low toxicity, an nitric oxide (NO) production-inhibiting effect and an inhibitory effect on the production of an inflammatory cytokine such as TNF-α, IL-1 and IL-6, the composition of the present invention, which contains the inventive Compound, a salt thereof or a prodrug therefor is useful as a therapeutic and/or prophylactic agent in a mammal (e.g., cat, cattle, dog, horse, goat, monkey, human and the like) against heart disease, autoimmune disease, inflammatory disease, central nervous system disease, infectious disease, sepsis, septic shock and the like, including ichorrhemia, endotoxin shock, exotoxin shock, cardiac deficiency, shock, hypotension, rheumatoid arthritis, osteoarthritis, gastritis, ulcerative colitis, peptic ulcer, stress-induced gastric ulcer, Crohn's disease, autoimmune disease, post-transplant tissue failure and rejection, postischemic re-perfusion failure, acute coronary microvascular embolism, shock-induced vascular embolism (disseminated intravascular coagulation (DIC) and the like), ischemic cerebral disorder, arterial sclerosis, malignant anemia, Fanconi's anemia, drepanocythemia, pancreatitis, nephrose syndrome, nephritis, renal failure, insulin-dependent diabetes, insulin-independent diabetes, hepatic porphyria, alcoholism, Parkinson's disease, chronic leukemia, acute leukemia, tumor, myeloma, side effects of anticancer agents, infantile and adult respiratory distress syndrome, pulmonary emphysema, dementia, Alzheimer's disease, multiple sclerosis, vitamin E deficiency, aging, sunburn, muscular dystrophy, myocarditis, cardiomyopathy, myocardial infarction, sequela of myocardial infaction, osteoporosis, pneumonia, hepatitis, psoriasis, pain, cataract, influenza infection, malaria, human immunodeficiency virus (HIV) infection, radiation-induced failure, burn, in vitro fertilization efficiency, hypercalcemia, tonic spondylitis, osteopenia, bone Behcet's disease, osteomalacia, fracture, acute bacterial meningitis, *Helicobactor pylori* infection, invasive staphylococcal infection, tuberculosis, systemic mycosis, herpes simplex virus infection, varicella-helpes zoster virus infection, human papilloma virus infection, acute viral encephalitis, encephalitis, asthma, atopic dermatitis, allergic rhinitis, reflux esophargitis, fever, hyper cholesteremia, hyperglycemia, hyperlipidemia, diabetic complication, diabetic renal disease, diabetic neuropathy, diabetic retinopathy, gout, gastric atony, hemorrhoid, systemic lupus erythematosus, spinal damage, insomnia, schizophrenia, epilepsy, cirrhosis, hepatic failure, instable angina, valvular disease, dialysis-induced thrombocytopenia, acute ischemic cerebral apoplexy, acute cerebral thrombosis, cancer metastasis, urinary bladder cancer, mammary cancer, uterine cervical cancer, colon cancer, gastric cancer, ovarian cancer, prostate cancer, parvicellular pulmonary cancer, non-parvicellular pulmonary cancer, malignant melanoma, Hodgkin's disease, non-Hodgkin lymphoma and the like.

While the dose of the composition of the present invention may vary depending on the kind of the inventive Compound, age, body weight and condition, the dosage form, the mode and the period of the treatment, it may, for example, be generally about 0.01 to about 1000 mg/kg, preferably about 0.01 to about 100 mg/kg, more preferably about 0.1 to about 100 mg/kg, most preferably about 0.1 to about 50 mg/kg, and particularly about 1.5 to about 30 mg/kg, as the inventive Compound (Iaa) or (Ie), per day in a patient having a sepsis (adult weighing about 60 kg), said daily dose being given intravenously all at once or in several portions during a day. It is a matter of course that a lower daily dose may be sufficient or an excessive dose may be required since the dose may vary depending on various factors as discussed above.

The composition of the present invention can be used concurrently with a drug other than compound (I), a salt thereof and a prodrug therefor.

The drugs that can be used concurrently with the composition of the present invention (hereinafter sometimes to be briefly referred to as a combination drug) are, for example, antibacterial agent, antifungal agent, non-steroidal antiinflammatory drug, steroid, anticoagulant, platelet aggregation inhibitor, thrombolytic drug, immunomodulator, antiprotozoal, antibiotic, antitussive and expectorant drug, sedative, anesthetic, antiulcer drug, antiarrhythmic, hypotensive diuretic, tranquilizer, antipsychotic, antitumor drug, hypolipidemic drug, muscle relaxant, anticonvulsant, antidepressant, antiallergic drug, cardiac, antiarrhythmic, vasodilator, vasoconstrictor, hypotensive diuretic, antidiabetic drug, antinarcotic, vitamin, vitamin derivative, therapeutic agent for arthritis, antirheumatic, antiasthmatic, therapeutic agent for pollakiuria/anischuria, therapeutic agent for atopic dermatitis, therapeutic agent for allergic rhinitis, hypertensive drug, endotoxin-antagonist or -antibody, signal transduction inhibitor, inhibitor of inflammatory mediator activity, antibody to inhibit inflammatory mediator activity, inhibitor of anti-inflammatory mediator activity, antibody to inhibit anti-inflammatory mediator activity and the like. Of these, antibacterial agent, antifungal agent, non-steroidal antiinflammatory drug, steroid, anticoagulant and the like are preferable. Specific examples thereof include the following.

(1) Antibacterial Agent

① sulfa drug sulfamethizole, sulfisoxazole, sulfamonomethoxine, sulfamethizole, salazosulfapyridine, silver sulfadiazine and the like.

② quinoline antibacterial agent nalidixic acid, pipemidic acid trihydrate, enoxacin, norfloxacin, ofloxacin, tosufloxacin tosilate, ciprofloxacin hydrochloride, lomefloxacin hydrochloride, sparfloxacin, fleroxacin and the like.

③ antiphthisic isoniazid, ethambutol (ethambutol hydrochloride), p-aminosalicylic acid (calcium p-aminosalicylate), pyrazinamide, ethionamide, protionamide, rifampicin, streptomycin sulfate, kanamycin sulfate, cycloserine and the like.

④ antiacidfast bacterium drug diaphenylsulfone, rifampicin and the like.

⑤ antiviral drug idoxuridine, aciclovir, vidarabine, ganciclovir and the like.

⑥ anti-HIV agent zidovudine, didanosine, zalcitabine, indinavir sulfate ethanolate, ritonavir and the like.

⑦ antispirochetele

⑧ antibiotic tetracycline hydrochloride, ampicillin, piperacillin, gentamicin, dibekacin, kanendomycin, lividomycin, tobramycin, amikacin, fradiomycin, sisomicin, tetracycline, oxytetracycline, rolitetracycline, doxycycline, ampicillin, piperacillin, ticarcillin, cephalothin, cephapirin, cephaloridine, cefaclor, cephalexin, cefroxadine, cefadroxil, cefamandole, cefotoam, cefuroxime, cefotiam, cefotiam hexetil, cefuroxime axetil, cefdinir, cefditoren piboxil, ceftazidime, cefpiramide, cefsulodin, cefinenoxime, cefpodoxime proxetil, cefpirome, cefozopran, cefepime, cefsulodin, cefinenoxime, cefinetazole, cefminox, cefoxitin, cefbuperazone, latamoxef, flomoxef, cefazolin, cefotaxime, cefoperazone, ceftizoxime, moxalactam, thienamycin, sulfazecin, aztreonam or a salt thereof, griseofulvin, lankacidin-group antibiotics (J. Antibiotics, 38, 877-885 (1985)) and the like.

(2) Antifungal Agent

① polyethylene antibiotic (e.g., amphotericin B, nystatin, trichomycin)

② griseofulvin, pyrrolnitrin and the like

③ cytosine metabolism antagonist (e.g., flucytosine)

④ imidazole derivative (e.g., econazole, clotrimazole, miconazole nitrate, bifonazole, croconazole)

⑤ triazole derivative (e.g. fluconazole, itraconazole, azole compound [2-[(1R,2R)-2-(2,4-difluorophenyl)-2-hydroxy-1-methyl-3-(1H-1,2,4-triazol-1-yl)propyl]-4-[4-(2,2,3,3-tetrafluoropropoxy)phenyl]-3(2H,4H)-1,2,4-triazolone]

⑥ thiocarbamic acid derivative (e.g. trinaphthol)

⑦ echinocandin derivative (e.g., caspofungin, micafungin, anidulafungin) and the like.

(3) non-Steroidal Antiinflammatory Drug acetaminophen, phenacetin, ethenzamide, sulpyrine, antipyrin, migrenin, aspirin, mefenamic acid, flufenamic acid, diclofenac sodium, loxoprofen sodium, phenylbutazone, indomethacin, ibuprofen, ketoprofen, naproxen, oxaprozin, flurbiprofen, fenbufen, pranoprofen, floctafenine, epirizole, tiaramide hydrochloride, zaltoprofen, gabexate mesilate, camostat mesilate, urinastatin, colchicine, probenecid, sulfinpyrazone, benzbromarone, allopurinol, gold sodium thiomalate, sodium hyaluronate, sodium salicylate, morphine hydrochloride, salicylic acid, atropine, scopolamine, morphine, pethidine, levorphanol, ketoprofen, naproxen, oxymorphone or a salt thereof, and the like.

(4) Steroid dexamethasone, hexestrol, methimazole, betamethasone, triamcinolone, triamcinolone acetonide, fluocinonide, fluocinolone acetonide, prednisolone, methylprednisolone, cortisone acetate, hydrocortisone, fluorometholone, beclometasone dipropionate, estriol and the like.

(5) Anticoagulant heparin sodium, sodium citrate, activated protein C, tissue factor pathway inhibitor, antithrombin III, dalteparin sodium, warfarin potassium, argatroban, gabexate, sodium citrate and the like.

(6) Platelet Aggregation Inhibitor ozagrel sodium, ethyl icosapentate, beraprost sodium, alprostadil, ticlopidine hydrochloride, pentoxifylline, dipyridamole and the like.

(7) Thrombolytic Drug tisokinase, urokinase, streptokinase and the like.

(8) Immunomodulator cyclosporin, tacrolimus, gusperimus, azathioprine, antilymphocyte serum, dried sulfonated immunoglobulin, erythropoietin, colony-stimulating factor, interleukin, interferon and the like.

(9) Antiprotozoal metronidazole, tinidazole, diethylcarbamazine citrate, quinine hydrochloride, quinine sulfate and the like.

(10) Antitussive and Expectorant Drug ephedrine hydrochloride, noscapine hydrochloride, codeine phosphate, dihydrocodeine phosphate, isoproterenol hydrochloride, ephedrine hydrochloride, methylephedrine hydrochloride, noscapine hydrochloride, alloclamide, chlophedianol, picoperidamine, chloperastine, protokylol, isoproterenol, salbutamol, terbutaline, oxymetabanol, morphine hydrochloride, dextromethorphan hydrobromide, oxycodone hydrochloride, dimemorphan phosphate, tipepidine hibenzate, pentoxyverine citrate, clofedanol hydrochloride, benzonatate, guaifenesin, bromhexine hydrochloride, ambroxol hydrochloride, acetylcysteine, ethyl cysteine hydrochloride, carbocysteine and the like.

(11) Sedative chlorpromazine hydrochloride, atropine sulfate, phenobarbital, barbital, amobarbital, pentobarbital, thiopental sodium, thiamylal sodium, nitrazepam, estazolam, flurazepam, haloxazolam, triazolam, flunitrazepam, bromovalerylurea, chloral hydrate, triclofos sodium and the like.

(12) Anesthetic (12-1) Local Anesthetic cocaine hydrochloride, procaine hydrochloride, lidocaine, dibucaine hydrochloride, tetracaine hydrochloride, mepivacaine hydrochloride, bupivacaine hydrochloride, oxybuprocaine hydrochloride, ethyl aminobenzoate, oxethazaine) and the like.

(12-2) General Anesthetic

① inhalation anesthetic (e.g., ether, halothane, nitrous oxide, isoflurane, enflurane), ② intravenous anesthetic (e.g., ketamine hydrochloride, droperidol, thiopental sodium, thiamylal sodium, pentobarbital) and the like.

(13) Antiulcer Drug metoclopromide, histidine hydrochloride, lansoprazole, metoclopramide, pirenzepine, cimetidine, ranitidine, famotidine, urogastrone, oxethazaine, proglumide, omeprazole, sucralfate, sulpiride, cetraxate, gefarnate, aldioxa, teprenone, prostaglandin and the like.

(14) Antiarrhythmic

① Na channel blocker (e.g., quinidine, procainamide, disopyramide, ajmaline, lidocaine, mexiletine, phenitoin), ② β-blocker (e.g., propranolol, alprenolol, bufetolol, oxprenolol, atenolol, acebutolol, metoprolol, bisoprolol, pindolol, carteolol, arotinolol, ③ K channel blocker (e.g., amiodarone), ④ Ca channel blocker (e.g., verapamil, diltiazem) and the like.

(15) Hypotensive Diuretic hexamethonium bromide, clonidine hydrochloride, hydrochlorothiazide, trichlormethiazide, furosemide, ethacrynic acid, bumetamide, mefruside, azosemide, spironolactone, potassium canrenoate, triamterene, amiloride, acetazolamide, D-mannitol, isosorbide, aminophyllin and the like.

(16) Tranquilizer diazepam, lorazepam, oxazepam, chlordiazepoxide, medazepam, oxazolam, cloxazolam, clotiazepam, bromazepam, etizolam, fludiazepam, hydroxyzine and the like.

(17) Antipsychotic chlorpromazine hydrochloride, prochlorperazine, trifluoperazine, thioridazine hydrochloride, perphenazine maleate, fluphenazine enanthate, prochlorperazine maleate, levomepromazine maleate, promethazine hydrochloride, haloperidol, bromperidol, spiperone, reserpine, clocapramine dihydrochloride, sulpiride, zotepine and the like.

(18) Antitumor Drug

6-O—(N-chloroacetylcarbamoyl)fumagillol, bleomycin, methotrexate, actinomycin D, mitomycin C, daunorubicin, adriamycin, neocarzinostatin, cytosine arabinoside, fluorouracil, tetrahydrofuryl-5-fluorouracil, picibanil, lentinan, levamisole, bestatin, azimexon, glycyrrhizin, doxorubicin hydrochloride, aclarubicin hydrochloride, bleomycin hydrochloride, peplomycin sulfate, vincristine sulfate, vinblastine sulfate, irinotecan hydrochloride, cyclophosphamide, melphalan, busulphan, thiotepa, procarbazine hydrochloride, cisplatin, azathioprine, mercaptopurine, tegafur, carmofur, cytarabine, methyltestosterone, testosterone propionate, testosterone enanthate, mepitiostane, fosfestol, chlormadinone acetate, leuprorelin acetate, buserelin acetate and the like.

(19) Hypolipidemic Drug clofibrate, ethyl 2-chloro-3-[4-(2-methyl-2-phenylpropoxy)phenyl]propionate (Chem. Pharm. Bull, 38, 2792-2796 (1990)), pravastatin, simvastatin, probucol, bezafibrate, clinofibrate, nicomol, cholestyramine, dextran sulfate sodium and the like.

(20) Muscle Relaxant pridinol, tubocurarine, pancuronium, tolperisone hydrochloride, chlorphenesin carbamate, baclofen, chlormezanone, mephenesin, chlorzoxazone, eperisone, tizanidine and the like.

(21) Anticonvulsant phenyloin, ethosuximide, acetazolamide, chlordiazepoxide, trimethadione, carbamazepine, phenobarbital, primidone, sulthiame, sodium valproate, clonazepam, diazepam, nitrazepam and the like.

(22) Antidepressant imipramine, clomipramine, noxiptiline, phenelzine, amitriptyline hydrochloride, nortriptyline hydrochloride, amoxapine, mianserin hydrochloride, maprotiline hydrochloride, sulpiride, fluvoxamine maleate, trazodone hydrochloride and the like.

(23) Antiallergic Drug diphenhydramine, chlorpheniramine, tripelennamine, metodilamine, clemizole, diphenylpyraline, methoxyphenamine, disodium cromoglycate, tranilast, repirinast, amlexanox, ibudilast, ketotifen, terfenadine, mequitazine, azelastine, epinastine, ozagrel hydrochloride, pranlkast hydrate, seratrodast and the like.

(24) Cardiac trans-pi-oxocamphor, terephyllol, aminophyllin, etilefrine, dopamine, dobutamine, denopamine, ubidecarenone aminophyllin, bencirin, amrinone, pimobendan, digitoxin, digoxin, methyldigoxin, lanatoside C, G-strophanthin and the like.

(25) Vasodilator oxyfedrine, diltiazem, tolazoline, hexobendine, bamethan, clonidine, methyldopa, guanabenz and the like.

(26) Vasoconstrictor dopamine, dobutamine denopamine and the like.

(27) Hypotensive Diuretic hexamethonium bromide, pentolinium, mecamylamine, ecarazine, clonidine, diltiazem, nifedipine and the like.

(28) Antidiabetic Drug tolbutamide, chlorpropamide, acetohexamide, glibenclamide, tolazamide, acarbose, epalrestat, troglitazone, glucagon, glymidine, glipzide, phenformin, buformin, metformin and the like.

(29) Antinarcotic levallorphan, nalorphine, naloxone or a salt thereof and the like.

(30) Fat-Soluble Vitamin

① vitamin A: vitamin $A_1$, vitamin $A_2$ and retinol palmitate
② vitamin D: vitamin $D_1$, $D_2$, $D_3$, $D_4$ and $D_5$
③ vitamin E: α-tocopherol, β-tocopherol, γ-tocopherol, δ-tocopherol, dl-α-tocopherol nicotinate
④ vitamin K: vitamin $K_1$, $K_2$, $K_3$ and $K_4$
⑤ folic acid (vitamin M) and the like.

(31) Vitamin Derivative various derivatives of vitamins, for example, vitamin $D_3$ derivatives such as 5,6-trans-cholecalciferol, 2,5-hydroxycholecalciferol, 1-α-hydroxycholecalciferol and the like, vitamin $D_2$ derivatives such as 5,6-trans-ergocalciferol and the like.

(32) Antiasthmatic isoprenaline hydrochloride, salbutamol sulfate, procaterol hydrochloride, terbutaline sulfate, trimetoquinol hydrochloride, tulobuterol hydrochloride, orciprenaline sulfate, fenoterol hydrobromide, ephedrine hydrochloride, ipratropium bromide, oxitropium bromide, flutropium bromide, theophyline, aminophyllin, disodium cromoglycate, tranilast, repirinast, anrexanone, ibudilast, ketotifen, terfenadine, mequitazine, azelastine, epinastine, ozagrel hydrochloride, pranlkast hydrate, seratrodast, dexamethasone, prednisolone, hydrocortisone, beclometasone dipropionate and the like.

(33) Therapeutic Agent for Pollakiuria/Anischuria flavoxate hydrochloride and the like.

(34) Atopic Dermatitis disodium cromoglycate and the like.

(35) Therapeutic Agent for Allergic Rhinitis disodium cromoglycate, chlorpheniramine maleate, alimemazine tartrate, clemastine fumarate, homochlorcyclizine hydrochloride, terfenadine, mequitazine and the like;

(36) Hypertensive Drug dopamine, dobutamine, denopamine, digitoxin, digoxin, methyldigoxin, lanatoside C, G-strophanthin and the like.

(37) Others hydroxicam, diaserine, megestrol acetate, nicerogolin, prostaglandins and the like.

A combined use of the composition of the present invention and a combination drug provides the following effects.

(1) The dose of the compound (I), a salt thereof and a prodrug therefor can be reduced than a sole administration of the composition of the present invention.

(2) A synergistic therapeutic effect can be achieved against the above-mentioned sepsis, septic shock, inflammatory diseases, infectious diseases and the like.

(3) A broad range of therapeutic effect can be achieved against various diseases developed in association with viral infection and the like.

With regard to the use of the composition of the present invention and a combination drug, the composition of the present invention and the combination drug are free of any limitation on the timing of the administration or the composition of the present invention, and the combination drug may be simultaneously administered to the administration object, or may be administered with time difference. The dose of the combination drug follows a clinical dose and can be appropriately determined depending on the administration object, administration route, disease, combination and the like.

The mode of administration of the composition of the present invention and the combination drug is not particularly limited, as long as the composition of the present invention and the combination drug are combined for administration. While the mode of such administration varies depending on the kind of the combination drug and the like, for example, (1) administration of a single preparation obtained by simultaneous addition of the composition of the present invention and the combination drug, (2) simultaneous administration of two kinds of preparations obtained by separate preparation of the composition of the present invention and a pharmaceutical composition of the combination drug, by a single administration route, (3) time stagger administration of two kinds of preparations obtained by separate preparation of the composition of the present invention and a pharmaceutical composition of the combination drug, by a single administration route, (4) simultaneous administration of two kinds of preparations obtained by separate preparation of the composition of the present invention and a pharmaceutical composition of the combination drug, by different administration routes, (5) time stagger administration of two kinds of preparations obtained by separate preparation of the composition of the present invention and a pharmaceutical composition of the combination drug, by different administration routes, such as administration in the order of the composition of the present invention and then a pharmaceutical composition of the combination drug, or in a reversed order, and the like are exemplified.

A pharmaceutical composition of the combination drug has low toxicity and can be administered safely by admixing the combination drug with, for example, a pharmacologically acceptable carrier according to a method known per se to give a pharmaceutical composition, such as tablets (inclusive of sugar-coated tablets and film-coated tablets), powders, granules, capsules, (inclusive of soft capsules), liquids, injections, suppositories, sustained release agents and the like, for oral or parenteral (e.g., topical, rectal or intravenous administration) administration. An injection can be administered intravenously, intramuscularly, subcutaneously, into the organs or directly into the lesion.

As the pharmacologically acceptable carrier usable for the production of the pharmaceutical composition of a combination drug, there are mentioned various conventional organic or inorganic carriers as a material for the preparation. Examples thereof include excipients, lubricants, binders and disintegrators for solid preparations, and solvents, solubilizing aids, suspending agents, isotonic agents, buffers and soothing agents for liquid preparations. Where necessary, conventional additives such as antiseptics, antioxidants, coloring agents, sweeteners, absorbents, moistening agents and the like can be used appropriately in suitable amounts.

As the excipient, there are mentioned, for example, lactose, sucrose, D-mannitol, starch, corn starch, crystalline cellulose, light anhydrous silicic acid and the like.

As the lubricant, there are mentioned, for example, magnesium stearate, calcium stearate, talc, colloidal silica and the like.

As the binder, there are mentioned, for example, crystalline cellulose, saccharose, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

As the disintegrator, there are mentioned, for example, starch, carboxymethylcellulose, carboxymethylcellulose calcium, sodium carboxymethyl starch, L-hydroxypropylcellulose and the like.

As the solvent, there are mentioned, for example, injectable water, alcohol, propylene glycol, Macrogol, sesame oil, corn oil, olive oil and the like.

As the solubilizing aid, there are mentioned, for example, polyethylene glycol, propylene glycol, D-mannitol, benzyl benzoate, ethanol, tris-aminomethane, cholesterol, triethanolamine, sodium carbonate, sodium citrate and the like.

As the suspending agent, there are mentioned, for example, surfactants such as stearyl triethanolamine, sodium lauryl sulfate, lauryl aminopropionic acid, lecithin, benzalkonium chloride, benzethonium chloride, glyceryl monostearate and the like; hydrophilic polymers such as polyvinyl alcohol, polyvinylpyrrolidone, carboxymethylcellulose sodiium, methylcellulose, hydroxymethylcellulose, hydroxyethylcellulose, hydroxypropylcellulose and the like.

As the isotonic agent, there are mentioned, for example, glucose, D-sorbitol, sodium chloride, glycerine, D-mannitol and the like.

As the buffer, there are mentioned, for example, buffers such as phosphate, acetate, carbonate, citrate and the like.

As the soothing agent, there are mentioned, for example, benzyl alcohol and the like.

As the antiseptic, there are mentioned, for example, p-oxybenzoates, chlorobutanol, benzyl alcohol, phenethyl alcohol, dehydroacetic acid, sorbic acid and the like.

As the antioxidant, there are mentioned, for example, sulfite, ascorbic acid, α-tocopherol and the like.

When a combination drug is added to the composition of the present invention, the amount of the combination drug can be appropriately determined depending on the administration object, administration route, disease and the like, and can be adjusted as are the aforementioned compound (I), a salt thereof and a prodrug therefor.

When the composition of the present invention and a pharmaceutical composition of the combination drug are used in combination, the content of the combination drug in the pharmaceutical composition of the combination drug can be appropriately determined depending on the administration object, administration route, disease and the like. It is generally about 0.01-100 wt %, preferably about 0.1-50 wt %, more preferably about 0.5-20 wt %, based on the preparation in total.

The content of the additive, such as a carrier, in the pharmaceutical composition of the combination drug varies depending on the form of the preparation. It is generally about 1-99.99 wt %, preferably about 10-90 wt %, based on the preparation in total.

A combination drug can be prepared into an aqueous injection together with a dispersant (e.g., Tween 80 (ATLASPOWDER USA), HCO60 (NIKKO CHEMICALS), polyethylene glycol, carboxymethylcellulose, sodium arginate, hydroxypropylmethylcellulose, dextrin and the like, a stabilizing agent (e.g., ascorbic acid, sodium pyrosulfite and the like), a surfactant (e.g., polysorbate 80, Macrogol and the like), a solubilizing agent (e.g., glycerine, ethanol and the like), a buffering agent (e.g., phosphoric acid, alkali metal salt thereof, citric acid, alkali metal salt thereof and the like), an isotonic agent (e.g., sodium chloride, potassium chloride, mannitol, sorbitol, glucose and the like), a pH adjusting agent (hydrochloric acid, sodium hydroxide and the like), a preservative (ethyl p-hydroxybenzoate, benzoic acid, methylparaben, propylparaben, benzyl alcohol and the like), a solubilizer (e.g., conc. glycerine, meglumine and the like), a solubilizing aid (e.g., propylene glycol, sucrose and the like), a soothing agent (e.g., glucose, benzyl alcohol and the like) and the like, or by dissolving, suspending or emulsifying in a vegetable oil (e.g., olive oil, sesame oil, peanut oil, cottonseed oil, corn oil and the like) or a solubilizing aid such as propylene glycol and the like to form an oil-based injection formulation.

In addition, a combination drug may be used instead of the compound (I), a salt thereof or a prodrug therefor to give an emulsion composition for injection of the present invention.

An oral formulation can be produced by compressing a combination drug together with an excipient (e.g., lactose, sucrose, starch and the like), a disintegrant (e.g., starch, calcium carbonate and the like), a binder (e.g., starch, gum arabic, carboxymethyl cellulose, polyvinyl pyrrolidone, hydroxypropyl cellulose and the like) or a glidant (e.g., talc, magnesium stearate, polyethylene glycol 6000 and the like) as appropriate, followed by a coating process known per se for the purpose of masking a taste, forming an enteric coat, or achieving a sustained release. Such coating may, for example, be hydroxypropylmethyl cellulose, ethyl cellulose, hydroxymethyl cellulose, hydroxypropyl cellulose, polyoxyethylene glycol, Tween 80, Pluronic F68, cellulose acetate phthalate, hydroxypropylmethyl cellulose phthalate, hydroxymethyl cellulose acetate succinate, Eudragid (ROHME, Germany, a copolymer of methacrylic acid and acrylic acid), a dye (e.g., colcothar, titanium oxide and the like) as appropriate.

The preparation for oral administration may be either a rapid release preparation or a sustained release preparation.

For example, when a suppository is produced, a combination drug may be formulated also as an oil-based or aqueous solid or semi-solid or liquid suppository by a method known per se. An oil-based suppository base may, for example, be a higher fatty glyceride (e.g., cocoa butter, WITEPSOL (DYNAMIT NOBEL) and the like), a middle fatty acid (e.g., MYGLYOL (DYNAMIT NOBEL) and the like), or a vegetable oil (e.g., sesame oil, soybean oil, cottonseed oil and the like) and the like as appropriate. An aqueous base may, for example, be a polyethylene glycols or a propylene glycol, and an aqueous gel base may, for example, be a natural gum, a cellulose derivative, a vinyl polymer, an acrylic polymer and the like.

Examples of the above-mentioned sustained release preparation include sustained release microcapsule and the like.

A sustained release microcapsule can be prepared by a method known per se. For example, a sustained release preparation shown in the following [2] is preferably formed and administered.

A combination drug can be formed into a preparation for oral administration such as a solid preparation (e.g., powder, granule, tablet, capsule) and the like, or a preparation for rectal administration such as a suppository and the like, depending on the kind of the drug.

In the following, [1] an injection of the combination drug and preparation thereof, [2] a sustained release preparation or a rapid release preparation of a combination drug and preparation thereof, and [3] a sublingual tablet, buccal or oral cavity rapid disintegrator of a combination drug and preparation thereof are concretely explained.

[1] Injection and Preparation Thereof

An injection containing a combination drug dissolved in water is preferable. The injection may contain benzoate and/or salicylate.

The injection is obtained by dissolving both a combination drug and, where desired, benzoate and/or salicylate in water.

The salt of the above-mentioned benzoic acid and salicylic acid includes, for example, alkali metal salts such as sodium, potassium and the like, alkaline earth metal salts such as calcium, magnesium and the like, ammonium salt, meglumine salt, and organic acid salt such as tromethamol and the like, and the like.

The concentration of the combination drug in the injection is about 0.5-50 w/v %, preferably about 3-20 w/v %. The concentration of the benzoate and/or salicylate is preferably 0.5-50 w/v %, more preferably 3-20 w/v %.

The injection may contain additives generally used for injections, such as a stabilizing agent (e.g., ascorbic acid, sodium pyrosulfite and the like), a surfactant (e.g., polysorbate 80, Macrogol and the like), a solubilizing agent (e.g., glycerine, ethanol and the like), a buffering agent (e.g., phosphoric acid, alkali metal salt thereof, citric acid, alkali metal salt thereof and the like), an isotonic agent (e.g., sodium chloride, potassium chloride and the like), a dispersing agent (e.g., hydroxypropylmethylcellulose, dextrin), a pH adjusting agent (hydrochloric acid, sodium hydroxide and the like), a preservative (ethyl p-hydroxybenzoate, benzoic acid and the like), a solubilizer (e.g., conc. glycerine, meglumine and the like), a solubilizing aid (e.g., propylene glycol, sucrose and the like), a soothing agent (e.g., glucose, benzyl alcohol and the like) and the like as appropriate. These additives are added in a proportion generally employed for injections.

The injection is preferably adjusted to pH 2-12, preferably 2.5-8.0, by the use of a pH adjusting agent.

The injection can be obtained by dissolving both the combination drug and, where desired, benzoate and/or salicylate, and where necessary, the above-mentioned additives in water. These may be dissolved in any order in a suitable manner as in conventional production of injections.

The injectable aqueous solution is preferably heated and, in the same manner as with conventional injections, subjected to, for example, sterilization by filtration, high pressure sterilization by heating and the like to provide an injection.

The injectable aqueous solution is preferably subjected to high pressure sterilization by heating at, for example, 100° C.-121° C. for 5 min-30 min.

It may be prepared into an antibacterial solution, so that it can be used as a preparation for plural subdivided administrations.

[2] Sustained Release Preparation or Rapid Release Preparation and Preparation Thereof A sustained release preparation wherein a core containing a combination drug is covered on demand with a film forming agent, such as a water-insoluble material, a swellable polymer and the like, is preferable. For example, a sustained release preparation for oral administration once a day is preferable.

The water-insoluble material to be used for the film forming agent is, for example, cellulose ethers such as ethylcellulose, butylcellulose and the like; cellulose esters such as cellulose acetate, cellulose propionate and the like; polyvinyl esters such as poly(vinyl acetate), poly(vinyl butyrate) and the like; acrylic polymers such as acrylic acid/methacrylic acid copolymer, methyl methacrylate copolymer, ethoxyethyl methacrylate/cinnamoethyl methacrylate/aminoalkyl methacrylate copolymer, polyacrylic acid, polymethacrylic acid, methacrylic acid alkylamide copolymer, poly(methyl methacrylate), polymethacrylate, polymethacrylic amide, aminoalkyl methacrylate copolymer, poly(methacrylic anhydride) and glycidyl methacrylate copolymer, particularly Eudragits (Rohm Pharma) such as Eudragit RS-100, RL-100, RS-30D, RL-30D, RL-PO, RS-PO (ethyl acrylate.methyl methacrylate.trimethyl chloride methacrylate.ammonium ethyl copolymer), Eudragit NE-30D (methyl methacrylate-.ethyl acrylate copolymer) and the like, and the like; hydrogenated oils such as hydrogenated castor oil (e.g., ラブ リーワックス; "Lovely Wax" (Freund Inc.)) and the like) and the like; waxes such as carnauba wax, fatty acid glycerine ester, paraffin and the like; polyglycerine fatty acid ester and the like.

As the swellable polymer, a polymer having an acidic dissociable group, which shows pH-dependent swelling, is preferable, and a polymer having an acidic dissociable group, which shows less swelling in an acidic range, such as in the stomach, but otherwise in a neutral range, such as in the small intestine and large intestine, is preferable.

Examples of the polymer having an acidic dissociable group, which shows pH-dependent swelling, include crosslinking type polyacrylic acid polymers such as Carbomer 934P, 940, 941, 974P, 980, 1342 and the like, polycarbophil, carcium polycarbophil (all mentioned above are the product of BF Goodrich), HI-BIS-WAKO 103, 104, 105, 304 (all being products of Waco Pure Chemicals Industries, Ltd.) and the like.

The film forming agent to be used for the sustained release preparation may further contain a hydrophilic material.

Examples of the hydrophilic material include polysaccharides optionally having a sulfuric acid group such as pullulan, dextrin, alkali metal salt of alginic acid and the like; polysaccharides having a hydroxy alkyl group or a carboxy alkyl group such as hydroxypropylcellulose, hydroxypropylmethylcellulose, carboxymethylcellulose sodium and the like; methylcellulose, polyvinylpyrrolidone, polyvinyl alcohol, polyethylene glycol and the like.

The content of the water-insoluble material of the film forming agent for a sustained release preparation is about 30-about 90% (w/w), preferably about 35-about 80% (w/w), more preferably about 40-75% (w/w), and the content of the swellable polymer is about 3-about 30% (w/w), preferably about 3-about 15% (w/w). The film forming agent may further contain a hydrophilic material, in which case the content of the hydrophilic material for film forming agent is not more than about 50% (w/w), preferably about 5-about 40% (w/w), more preferably about 5-about 35% (w/w). As used herein, the above-mentioned % (w/w) is a percentage relative to the film forming agent composition wherein the solvent (e.g., water, lower alcohol such as methanol, ethanol and the like) has been removed from the film forming liquid agent.

A sustained release preparation is produced by preparing a core containing a drug as exemplarily mentioned below, and coating the resulting core with a film forming liquid agent prepared by dissolving by heating or dissolving or dispersing in a solvent a water-insoluble material, a swellable polymer and the like.

I. Preparation of Core Containing a Drug

The form of the core containing a drug (hereinafter sometimes simply referred to as a core) to be coated with a film forming agent is not particularly limited, but it is preferably formed into particles such as granules, subtilized granules and the like.

When the core is made of granules or subtilized granules, the average particle size thereof is preferably about 150-2,000 μm, more preferably about 500-about 1,400 μm.

The core can be prepared by a typical production method. For example, a drug is mixed with suitable excipients, binders, disintegrators, lubricants, stabilizers and the like, and subjected to wet extrusion granulation, fluidized bed granulation and the like.

The drug content of the core is about 0.5-about 95% (w/w), preferably about 5.0-about 80% (w/w), more preferably about 30-about 70% (w/w).

Examples of the excipient to be contained in the core include saccharides such as sucrose, lactose, mannitol, glucose and the like, starch, crystalline cellulose, calcium phosphate, corn starch and the like. Of these, crystalline cellulose and corn starch are preferable.

Examples of the binder include polyvinyl alcohol, hydroxypropylcellulose, polyethylene glycol, polyvinylpyrrolidone, Pluronic F68, gum arabic, gelatin, starch and the like. Examples of the disintegrator include carboxymethylcellulose calcium (ECG505), crosscarmelose sodium (Ac-Di-Sol), crosslinked polyvinylpyrrolidone (Crospovidone), low substituted hydroxypropylcellulose (L-HPC) and the like. Of these, hydroxypropylcellulose, polyvinylpyrrolidone and low substituted hydroxypropylcellulose are preferable. Examples of the lubricant and coagulation preventive include talc, magnesium stearate and inorganic salts thereof, and examples of the lubricant include polyethylene glycol and the like. Examples of the stabilizer include acids such as tartaric acid, citric acid, succinic acid, fumaric acid acid, maleic acid and the like.

The core can be also prepared, besides the above-mentioned production methods, by, for example, rolling granulation wherein a drug or a mixture of a drug and an excipient, a lubricant and the like is added by small portions while spraying a binder dissolved in a suitable solvent such as water, lower alcohol (e.g., methanol, ethanol and the like) and the like on an inert carrier particles to be the center of the core, a pan coating method, a fluidized bed coating method or a melt granulating method. Examples of the inert carrier particle include those prepared from sucrose, lactose, starch, crystalline cellulose and waxes, which preferably has an average particle size of about 100 μm-about 1,500 μm.

To separate the drug contained in the core from the film forming agent, the surface of the core may be coated with a protective agent. Examples of the protective agent include the aforementioned hydrophilic material, water-insoluble material and the like. As the protective agent, preferably polyethylene glycol, polysaccharides having a hydroxy alkyl group or a carboxy alkyl group, more preferably hydroxypropylmethylcellulose and hydroxypropylcellulose are used. The protective agent may contain, as a stabilizer, an acid such as tartaric acid, citric acid, succinic acid, fumaric acid acid, maleic acid and the like, and a lubricant such as talc and the like. When the protective agent is used, the amount to be coated is about 1-about 15% (w/w), preferably about 1-about 10% (w/w), more preferably about 2-about 8% (w/w), relative to the core.

The protective agent can be coated by a typical coating method. Specifically, the protective agent is, for example, spray-coated to the core by a fluidized bed coating method, a pan coating method, and the like.

II. Coating of Core with a Film Forming Agent

The core obtained in the aforementioned I is coated with a film forming liquid agent prepared by dissolving by heating or dissolving or dispersing in a solvent the aforementioned water-insoluble material, a pH-dependent swellable polymer, and a hydrophilic material to provide a sustained release preparation.

For coating a film forming liquid agent to a core, for example, a spray coating method and the like can be employed.

The composition ratio of the water-insoluble material, swellable polymer or hydrophilic material in the film forming liquid agent is suitable determined such that the content of each component of the coating film becomes the aforementioned content.

The coating amount of the film forming agent is about 1-about 90% (w/w), preferably about 5-about 50% (w/w), more preferably about 5-35% (w/w), relative to the core (exclusive of the coating amount of protective agent).

As the solvent for the film forming liquid agent, water and organic solvents can be used alone or in a mixture of the both. The mixing ratio (water/organic solvent: weight ratio) of water and the organic a solvent in the mixture can vary within the range of 1-100%, which is preferably 1-about 30%. The organic solvent is not subject to any particular limitation as long as it dissolves the water-insoluble material. For example, lower alcohols such as methyl alcohol, ethyl alcohol, isopropyl alcohol, n-butyl alcohol and the like, lower alkanone such as acetone and the like, acetonitrile, chloroform, methylene chloride and the like are used. Of these, lower alcohol is preferable, and ethyl alcohol and isopropyl alcohol are particularly preferable. Water and a mixture of water and an organic solvent is preferably used as a solvent of the film forming agent. Where necessary, the film forming liquid agent may contain an acid such as tartaric acid, citric acid, succinic acid, fumaric acid acid, maleic acid and the like for the stabilization of the film forming liquid agent.

When spray coating is employed, the method follows a conventional coating method, which is specifically spray coating of a film forming liquid agent to the core by, for example, a fluidized bed coating method, a pan coating method and the like. Where necessary, talc, titanium oxide, magnesium stearate, calcium stearate, light anhydrous silicic acid and the like may be added as a lubricant, and glycerine fatty acid ester, hydrogenated castor oil, triethyl citrate, cetyl alcohol, stearyl alcohol and the like may be added as a plasticizer.

After coating of a film forming agent, an antistatic agent such as talc and the like may be added as necessary.

A rapid release preparation may be a liquid (solution, suspension, emulsion and the like) or a solid (particles, pill, tablet and the like). While an oral administration agent, and a parenteral administration agent, such as injection and the like, are used, with preference given to an agent for oral administration.

A rapid release preparation may generally contain, in addition to the drug which is an active ingredient, carriers, additives and excipients (hereinafter sometimes simply referred to as an excipient) conventionally used in the field of preparation. The excipient for a preparation is not subject to any particular limitation as long as it is conventionally employed as an excipient for a preparation. For example, the excipient for the oral solid preparation includes lactose, starch, corn starch, crystalline cellulose (Asahi Kasei Corporation, Avicel PH101 and the like), powder sugar, granulated sugar, mannitol, light anhydrous silicic acid, magnesium carbonate, calcium carbonate, L-cysteine and the like, preferably corn starch and mannitol and the like. These excipients may be used alone or in combination. The content of the excipient is, for example, about 4.5-about 99.4 w/w %, preferably about 20-about 98.5 w/w %, more preferably about 30-about 97 w/w %, relative to the total amount of the rapid release preparation.

The drug content of the rapid release preparation is appropriately determined from the range of about 0.5-about 95%, preferably about 1-about 60%, relative to the total amount of the rapid release preparation.

When the rapid release preparation is an oral solid preparation, it generally contains a disintegrator in addition to the above-mentioned components. Examples of the disintegrator include calcium carboxymethylcellulose (manufactured by Gotoku Yakuhin, ECG-505), crosscarmelose sodium (e.g., Asahi Kasei Corporation, Actisol), Crospovidone (e.g., Colicone CL, BASF), low substituted hydroxypropylcellulose (Shin-Etsu Chemical Co., Ltd.), carboxymethyl starch (Matsutani Chemical Industry Co., Ltd., sodium carboxymethyl starch (manufactured by Kimura Sangyo, Exprotab), partially a starch (PCS, Asahi Kasei Corporation) and the like. For example, one capable of disintegrating granules by water absorption, swelling, forming a channel between the active ingredient constituting the core and an excipient upon contact with water and the like can be used. These disintegrators can be used alone or in combination. The amount of the disintegrator is appropriately determined depending on the kind of the combination drug to be used and amount thereof, design of the release preparation and the like. It is generally about 0.05-about 30 w/w %, preferably about 0.5-about 15 w/w %, relative to the total amount of the rapid release preparation.

When the rapid release preparation is an oral preparation, the oral solid preparation may further contain, in addition to the above-mentioned composition, routine additives used for solid preparation on demand. Examples of the additive include a binder (e.g., sucrose, gelatin, gum arabic powder, methylcellulose, hydroxypropylcellulose, hydroxypropylmethylcellulose, carboxymethylcellulose, polyvinylpyrrolidone, Pullulan, dextrin and the like), a lubricant (e.g., polyethylene glycol, magnesium stearate, talc, light anhydrous silicic acid (e.g., Aerosil (Nippon Aerosil)), a surfactant (e.g., anionic surfactant such as sodium alkylsulfate and the like, non-ionic surfactant such as polyoxyethylene fatty acid ester and polyoxyethylenesorbitan fatty acid ester, polyoxyethylene castor oil derivative and the like, and the like), a coloring agent (e.g., synthetic color, caramel, iron oxide red, titanium oxide, riboflavins), where necessary, a corrigent (e.g., a sweetener, flavor and the like), an absorbent, an antiseptic, a moistening agent, an antistatic agent and the like. As the stabilizer, an organic acid such as tartaric acid, citric acid, succinic acid, fumaric acid and the like may be added.

Examples of the above-mentioned binder preferably include hydroxypropylcellulose, polyethylene glycol, polyvinylpyrrolidone and the like.

The rapid release preparation can be prepared based on the conventional preparation method, by mixing each of the aforementioned components, and where necessary, further kneading and forming. The above-mentioned mixing can be performed by a conventional method, such as mixing, kneading and the like. Specifically, for example, when a rapid release preparation is formed into particles, a vertical granulator, a universal kneader (manufactured by Hata Tekkosho), a fluidized bed granulator FD-5S (Powrex Corporation) and the like are used for mixing, which is followed by granulating by wet extrusion granulation, fluidized bed granulation and the like, to give the preparation, as in the preparation of the core of the aforementioned sustained release preparation.

The rapid release preparation and the sustained release preparation thus obtained may be used as they are. Alternatively, after suitable separate preparation along with an excipient for a preparation and the like according to a conventional method, they may be administered simultaneously or at optional administration intervals. Alternatively, they may be prepared into a single preparation for oral administration (e.g., granule, subtilized granule, tablet, capsule and the like) as they are or along with excipient for preparation and the like as appropriate. The both preparations are converted to granules or subtilized granules and filled in a single capsule and the like to give a preparation for oral administration.

[3] A Sublingual Tablet, Buccal or Oral Cavity Rapid Disintegrator and Preparation Thereof The sublingual tablet, buccal preparation and oral cavity rapid disintegrator may be a solid preparation such as tablet and the like or an oral cavity mucous membrane adhesion tablet (film).

As the sublingual tablet, buccal or oral cavity rapid disintegrator, a preparation containing a combination drug and an excipient is preferable. It may contain auxiliaries such as a lubricant, an isotonic agent, a hydrophilic carrier, a water dispersible polymer, a stabilizer and the like. For easy absorption and enhanced bioavailability, β-cyclodextrin or β-cyclodextrin derivative (e.g., hydroxypropyl-β-cyclodextrin and the like) and the like may be contained.

Examples of the above-mentioned excipient include lactose, sucrose, D-mannitol, starch, crystalline cellulose, light anhydrous silicic acid and the like. Examples of the lubricant include magnesium stearate, calcium stearate, talc, colloidal silica and the like, particularly magnesium stearate and colloidal silica are preferable. Examples of the isotonic agent include sodium chloride, glucose, fructose, mannitol, sorbitol, lactose, saccharose, glycerine, urea and the like, particularly mannitol is preferable. Examples of the hydrophilic carrier include swellable hydrophilic carriers such as crystalline cellulose, ethylcellulose, crosslinked polyvinylpyrrolidone, light anhydrous silicic acid, silicic acid, dicalcium phosphate, calcium carbonate and the like, particularly crystalline cellulose (e.g., microcrystalline cellulose and the like) is preferable. Examples of the water dispersible polymer include gum (e.g., gum tragacanth, acacia gum, guar gum), alginate (e.g., sodium alginate), cellulose derivative (e.g., methylcellulose, carboxymethylcellulose, hydroxymethylcellulose, hydroxypropylcellulose, hydroxypropylmethylcellulose), gelatin, soluble starch, polyacrylic acid (e.g., carbomer), polymethacrylic acid, polyvinyl alcohol, polyethylene glycol, polyvinylpyrrolidone, polycarbofil, ascorbic palmitate and the like, with preference given to hydroxypropylmethylcellulose, polyacrylic acid, alginate, gelatin, carboxymethylcellulose, polyvinylpyrrolidone, polyethylene glycol and the like. Particularly, hydroxypropylmethylcellulose is preferable. Examples of the stabilizer include cysteine, thiosorbitol, tartaric acid, citric acid, sodium carbonate, ascorbic acid, glycine, sodium sulfite and the like, particularly, citric acid and ascorbic acid are preferable.

The sublingual tablet, buccal and oral cavity rapid disintegrator can be produced by mixing a combination drug and an excipient by a method known per se. Where desired, the above-mentioned auxiliaries such as a lubricant, an isotonic agent, a hydrophilic carrier, a water dispersible polymer, a stabilizer, a coloring agent, a sweetener, an antiseptic and the like may be contained. After mixing the above-mentioned components simultaneously or with time staggering, the mixture is compression formed under pressure to give sublingual tablet, buccal or oral cavity rapid disintegrator. To achieve a suitable hardness, a solvent such as water, alcohol and the like is used to moisten or wet as necessary before and after the compession forming. After the forming, the tablets are dried.

When a mucous membrane adhesion tablet (film) is produced, a combination drug and the above-mentioned water dispersible polymer (preferably, hydroxypropylcellulose, hydroxypropylmethylcellulose), an excipient and the like are dissolved in a solvent such as water and the like, and the obtained solution is cast to give a film. In addition, an additive such as a plasticizer, a stabilizer, an antioxidant, a preservative, a coloring agent, a buffer, a sweetener and the like may be added. To impart suitable elasticity to the film, glycols such as polyethylene glycol, propylene glycol and the like may be added, and to increase adhesion of the film to the oral cavity mucous membrane lining, bioadhesive polymer (e.g., polycarbofil, carbopol) may be added. The casting includes pouring the solution on a non-adhesive surface, spreading the solution in a uniform thickness (preferably about 10-1000µ) with a coating tool such as doctor blade and the like and drying the solution to give a film. The film thus formed may be dried at room temperature or under heating and cut into a desired surface area.

Examples of preferable oral cavity rapid disintegrator is a solid rapid diffusing administration agent having a net structure of a combination drug and water soluble or water diffusable carrier which are inert to the combination drug. The net structure can be obtained by sublimation of a solvent from the solid composition consisting of a solution obtained by dissolving a combination drug in a suitable solvent.

The oral cavity rapid disintegrator preferably contains, in addition to the combination drug, a matrix forming agent and a secondary component.

Examples of the matrix forming agent include animal proteins or vegetable proteins such as gelatins, dextrins, soybeans, wheat, psyllium seed protein and the like; rubber substances such as gum arabic, guar gum, agar, xanthan and the like; polysaccharides; alginic acids; carboxymethylcelluloses; carragheenans; dextrans; pectins; synthetic polymers such as polyvinylpyrrolidone and the like; a material derived from a gelatin-gum arabic complex and the like. In addition, saccharides such as mannitol, dextrose, lactose, galactose, trehalose and the like; cyclic saccharides such as cyclodextrin and the like; inorganic salts such as sodium phosphate, sodium chloride, aluminum silicate and the like; amino acid having 2 to 12 carbon atoms such as glycine, L-alanine, L-aspartic acid, L-glutamine acid, L-hydroxyproline, L-isoleucine, L-leucine, L-phenylalanine and the like are exemplified.

It is possible to introduce one or more matrix forming agents into a solution or suspension before preparation into a solid. Such matrix forming agent may exist with a surfactant or without a surfactant. The matrix forming agent can form a matrix, and also can help maintain the diffusion of the inventive Compound or a combination drug in the solution or suspension.

The composition may contain a secondary component such as a preservative, an antioxidant, a surfactant, a thickener, a coloring agent, a pH adjusting agent, a flavor, a sweetener, a taste masking reagent and the like. Examples of a suitable coloring agent include red, black and yellow ferric oxides and FD&C dyes of Elis and Eberald, such as FD&C blue NO. 2, FD&C red No. 40 and the like. A suitable flavor contains mint, raspberry, licorice, orange, lemon, grapefruit, caramel, vanilla, cherry, grape flavor and a combination of these. Suitable pH adjusting agent includes citric acid, tartaric acid, phosphoric acid, hydrochloric acid and maleic acid. Suitable sweetener includes aspartame, acesulfame K, thaumatin and the like. Suitable taste masking agent includes sodium bicarbonate, ion exchange resin, cyclodextrin inclusion compound, adsorbent substance and microcapsuled apomorphine.

The preparation contains a combination drug generally in a proportion of about 0.1-about 50 wt %, preferably about 0.1-about 30 wt %, and is capable of dissolving 90% or more of a combination drug in water for about 1 min-about 60 min, preferably about 1 min-about 15 min, more preferably about 2 min-about 5 min, such as the above-mentioned sublingual tablet, buccal and the like, and an oral cavity rapid disintegrator that disintegrates within 1-60 sec. preferably 1-30 sec, more preferably 1-10 sec, after being placed in an oral cavity is preferable.

The content of the above-mentioned excipient in the whole preparation is about 10-about 99 wt %, preferably about 30-about 90 wt %. The content of the β-cyclodextrin or β-cyclodextrin derivative relative to the whole preparation is 0-about 30 wt %. The content of the lubricant relative to the whole preparation is about 0.01-about 10 wt %, preferably about 1-about 5 wt %. The content of the isotonic agent relative to the whole preparation is about 0.1-about 90 wt %, preferably about 10-about 70 wt %. The content of the hydrophilic carrier relative to the whole preparation is about 0.1- about 50 wt %, preferably about 10-about 30 wt %. The content of the water dispersible polymer relative to the whole preparation is about 0.1-about 30 wt %, preferably about 10-about 25 wt %. The content of the stabilizer relative to the whole preparation is about 0.1-about 10 wt %, preferably about 1-about 5 wt %. The above-mentioned preparation may contain additives such as a coloring agent, a sweetener, an antiseptic and the like as necessary.

While the dose of the pharmaceutical composition of the combination drug varies depending on the kind of the combination drug, the patient's age, body weight and condition, the dosage form, the mode and the period of the treatment, the amount of the combination drug may, for example, be generally about 0.01 to about 1000 mg/kg, preferably about 0.01 to about 100 mg/kg, more preferably about 0.1 to about 100 mg/kg, most preferably about 0.1 to about 50 mg/kg, and particularly about 1.5 to about 30 mg/kg per day in a patient (adult weighing about 60 kg), said daily dose being given intravenously all at once or in several portions during a day. It is a matter of course that a lower daily dose may be sufficient or an excessive dose may be required since the dose may vary depending on various factors as discussed above.

The combination drug may be contained in any amount as long as a side effect does not pose a problem. While the daily dose of the combination drug may vary depending on the disease state, the age, sex, body weight and difference in sensitivity of the administration object, timing and interval of administration, characteristics of the pharmaceutical preparation, dispensing, kind, the kind of active ingredient and the like and is not particularly limited, the amount of the drug is generally about 0.001-2000 mg, preferably about 0.01-500 mg, more preferably about 0.1-100 mg, per 1 kg body weight of mammal by oral administration, which is generally administered all at once or in 2 to 4 portions during a day.

When the composition of the present invention and the pharmaceutical composition of a combination drug are concurrently administered, they may be administered at the same time, or the pharmaceutical composition of a combination drug may be administered first, and then the composition of the present invention may be administered. Alternatively, the composition of the present invention may be administered first, and then the pharmaceutical composition of a combination drug may be administered. For time stagger administration, the time difference varies depending on the active ingredient to be administered, dosage form and administration route. For example, when the pharmaceutical composition of a combination drug is to be administered first, the composition of the present invention is administered within 1 min-3 days, preferably 10 min-1 day, more preferably 15 min-1 hour, after the administration of the pharmaceutical composition of a combination drug. When the composition of the present invention is to be administered first, the pharmaceutical composition of a combination drug is administered within 1 min-1 day, preferably 10 min-6 hours, more preferably 15 min-1 hour, after the administration of the composition of the present invention.

EXAMPLES

The present invention is further described with referring to Reference Examples, Examples and Experiments, which are not intended to restrict the invention.

A $^1$H NMR spectrum was determined by a VARIAN GEMINI 200 (200 MHz) spectrometer using tetramethyl silane as an internal standard and represented as the entire 6 values in ppm. The number in a bracket when a solvent mixture was employed is the volume ratio of each mixture. A % is a % by weight unless otherwise specified. The ratio of the solvents in a chromatography on silica gel is the volume ratio of the solvents to be admixed.

A more polar diastereomer means a diastereomer having a smaller Rf value when determined by a normal phase thin layer chromatography under a same condition (for example using ethyl acetate/hexane as an eluent), which a less polar diastereomer means a diastereomer having a larger Rf value in such determination.

The meanings of the abbreviations as used in the Examples are as follows:

s: singlet d: doublet: t: triplet q: quartet

DD: double doublet tt: triple triplet m: multiplet br: broad

J: coupling constant

The Reference Example A to be mentioned below can be produced according to Reference Example of WO99/46424 and Reference Example B can be produced according to Example of WO99/46424.

Reference Example A

Reference Example A1 ethyl 2-sulfo-1-cyclohexene-1-carboxylate

Reference Example A2 ethyl 2-chlorosulfonyl-1-cyclohexene-1-carboxylate

Reference Example A3 ethyl 2-chlorosulfonyl-1-cyclopentene-1-carboxylate

Reference Example A4 ethyl 2-chlorosulfonyl-1-cycloheptene-1-carboxylate

Reference Example A5 6-[N-(4-chloro-2-fluorophenyl)sulfamoyl]-1-cyclohexene-1-carboxylic acid sodium salt Reference Example A6 1-(3-fluoro-4-nitrophenyl)-1H-1,2,4-triazole Reference Example A7 1-(4-amino-3-fluorophenyl)-1H-1,2,4-triazole Reference Example A8 methyl 4-benzyloxycarbonylamino-3-chlorobenzoate Reference Example A9 4-benzyloxycarbonylamino-3-chlorobenzoic acid Reference Example A10 tert-butyl N-(4-benzyloxycarbonylamino-3-chlorobenzoyl)glycinate Reference Example A11 tert-butyl N-(4-amino-3-chlorobenzoyl)glycinate Reference Example A12 6-[N-(2,4-difluorophenyl)sulfamoyl]-1-cyclohexene-1-carboxylic acid Reference Example A13 ethyl 2-mercapto-5-phenyl-1-cyclohexene-1-carboxylate Reference Example A14 2-chlorosulfonyl-5-phenyl-1-cyclohexene-1-carboxylate Reference Example A15 ethyl 5-tert-butyl-2-mercapto-1-cyclohexene-1-carboxylate Reference Example A16 ethyl 5-tert-butyl-2-chlorosulfonyl-1-cyclohexene-1-carboxylate Reference Example A17 ethyl 5,5-dimethyl-2-mercapto-1-cyclohexene-1-carboxylate Reference Example A18 ethyl 2-chlorosulfonyl-5,5-dimethyl-1-cyclohexene-1-carboxylate Reference Example B Reference Example B1 ethyl 6-[N-(4-chloro-2-fluorophenyl)sulfamoyl]-1-cyclohexene-1-carboxylate (compound 1)

Reference Example B2 ethyl 6-[N-(4-chloro-2-fluorophenyl)-N-methylsulfamoyl]-1-cyclohexene-1-carboxylate (compound 2)

Reference Example B3 ethyl 6-[N-(2,4-difluorophenyl)sulfamoyl]-1-cyclohexene-1-carboxylate (compound 3)

Reference Example B4 ethyl 6-[N-(2,6-diisopropylphenyl)sulfamoyl]-1-cyclohexene-1-carboxylate (compound 4)

Reference Example B5 ethyl 6-[N-(4-nitrophenyl)sulfamoyl]-1-cyclohexene-1-carboxylate (compound 5)

Reference Example B6 ethyl 6-(N-phenylsulfamoyl)-1-cyclohexene-1-carboxylate (compound 6) ethyl 2-(N-phenylsulfamoyl)-1-cyclohexene-1-carboxylate (compound 7)

Reference Example B7 ethyl 2-[N-(4-chloro-2-fluorophenyl)sulfamoyl]-1-cyclohexene-1-carboxylate (compound 9)

Reference Example B8 2-(4-methoxyphenyl)-4,5,6,7tetrahydro-1,2-benzisothiazol-3(2H)-one 1,1-dioxide (compound 67)

ethyl 2-[N-(4-methoxyphenyl)sulfamoyl]-1-cyclohexene-1-carboxylate (compound 8)

Reference Example B9 ethyl 6-[N-(2-fluorophenyl)sulfamoyl]-1-cyclohexene-1-carboxylate (compound 10)

Reference Example B10 ethyl 6-[N-(3-fluorophenyl)sulfamoyl]-1-cyclohexene-1-carboxylate (compound 11)

Reference Example B11 2-(4-fluorophenyl)-4,5,6,7-tetrahydro-1,2-benzisothiazol-3(2H)-one 1,1-dioxide (compound 68)

ethyl 6-[N-(4-fluorophenyl)sulfamoyl]-1-cyclohexene-1-carboxylate (compound 12)

ethyl 2-[N-(4-fluorophenyl)sulfamoyl]-1-cyclohexene-1-carboxylate (compound 18)

Reference Example B12 ethyl 6-[N-(2,6-difluorophenyl)sulfamoyl]-1-cyclohexene-1-carboxylate (compound 13)

Reference Example B13 ethyl 6-[N-(2,3-difluorophenyl)sulfamoyl]-1-cyclohexene-1-carboxylate (compound 14)

Reference Example B14 ethyl 6-[N-(2,5-difluorophenyl)sulfamoyl]-1-cyclohexene-1-carboxylate (compound 15)

Reference Example B15 ethyl 6-[N-(3,4-difluorophenyl)sulfamoyl]-1-cyclohexene-1-carboxylate (compound 16)

Reference Example B16 ethyl 6-[N-(3,5-difluorophenyl)sulfamoyl]-1-cyclohexene-1-carboxylate (compound 17)

Reference Example B17 1-ethyl 6-[N-(2,4-difluorophenyl)sulfamoyl]-1-cyclohexene-1-carboxylate (compound 19)

d-ethyl 6-[N-(2,4-difluorophenyl)sulfamoyl]-1-cyclohexene-1-carboxylate (compound 20)

Reference Example B18 ethyl 6-[N-(2-ethoxycarbonylphenyl)sulfamoyl]-1-cyclohexene-1-carboxylate (compound 21)

Reference Example B19 methyl 6-[N-(2,4-difluorophenyl)sulfamoyl]-1-cyclohexene-1-carboxylate (compound 22)

Reference Example B20 propyl 6-[N-(2,4-difluorophenyl)sulfamoyl]-1-cyclohexene-1-carboxylate (compound 23)

Reference Example B21 methyl 6-[N-(4-chloro-2-fluorophenyl)sulfamoyl]-1-cyclohexene-1-carboxylate (compound 24)

Reference Example B22 isopropyl 6-[N-(2,4-difluorophenyl)sulfamoyl]-1-cyclohexene-1-carboxylate (compound 25)

Reference Example B23 ethyl 6-[N-(2-methoxycarbonylphenyl)sulfamoyl]-1-cyclohexene-1-carboxylate (compound 26)

Reference Example B24 ethyl 6-[N-(2-fluoro-4-methylphenyl)sulfamoyl]-1-cyclohexene-1-carboxylate (compound 27)

Reference Example B25 ethyl 6-[N-(2-chlorophenyl)sulfamoyl]-1-cyclohexene-1-carboxylate (compound 28)

Reference Example B26 ethyl 6-[N-(2-chloro-4-fluorophenyl)sulfamoyl]-1-cyclohexene-1-carboxylate (compound 29)

Reference Example B27 ethyl 6-[N-(4-chlorophenyl)sulfamoyl]-1-cyclohexene-1-carboxylate (compound 30)

Reference Example B28 ethyl 6-[N-(2,3,4-trifluorophenyl)sulfamoyl]-1-cyclohexene-1-carboxylate (compound 31)

Reference Example B29 isobutyl 6-[N-(2,4-difluorophenyl)sulfamoyl]-1-cyclohexene-1-carboxylate (compound 32)

Reference Example B30 butyl 6-[N-(2,4-difluorophenyl)sulfamoyl]-1-cyclohexene-1-carboxylate (compound 33)

Reference Example B31 ethyl 6-[N-(4-bromo-2-fluorophenyl)sulfamoyl]-1-cyclohexene-1-carboxylate (compound 34)

Reference Example B32 ethyl 6-[N-(2,4-dichlorophenyl)sulfamoyl]-1-cyclohexene-1-carboxylate (compound 35)

Reference Example B33 ethyl 6-[N-(2-acetoxyphenyl)sulfamoyl]-1-cyclohexene-1-carboxylate (compound 36)

Reference Example B34 ethyl 6-[N-(3-chlorophenyl)sulfamoyl]-1-cyclohexene-1-carboxylate (compound 37)

Reference Example B35 ethyl 6-[N-(2,3-dichlorophenyl)sulfamoyl]-1-cyclohexene-1-carboxylate (compound 38)

Reference Example B36 ethyl 6-[N-(2-ethylphenyl)sulfamoyl]-1-cyclohexene-1-carboxylate (compound 39)

Reference Example B37 ethyl 6-[N-[4-(2H-1,2,3-triazol-2-yl)phenyl]sulfamoyl]-1-cyclohexene-1-carboxylate (compound 40)

Reference Example B38 ethyl 6-[N-(2,5-dichlorophenyl)sulfamoyl]-1-cyclohexene-1-carboxylate (compound 41)

Reference Example B39 ethyl 6-[N-(2-trifluoromethoxyphenyl)sulfamoyl]-1-cyclohexene-1-carboxylate (compound 42)

Reference Example B40 ethyl 6-[N-(2,4,5-trifluorophenyl)sulfamoyl]-1-cyclohexene-1-carboxylate (compound 43)

Reference Example B41 ethyl 6-[N-[4-(2H-tetrazol-2-yl)phenyl]sulfamoyl]-1-cyclohexene-1-carboxylate (compound 44)

Reference Example B42 ethyl 6-[N-(2-chloro-4-methylphenyl)sulfamoyl]-1-cyclohexene-1-carboxylate (compound 45)

Reference Example B43 ethyl 6-[N-(4-fluoro-2-methylphenyl)sulfamoyl]-1-cyclohexene-1-carboxylate (compound 46)

Reference Example B44 ethyl 6-[N-(2,6-dichlorophenyl)sulfamoyl]-1-cyclohexene-1-carboxylate (compound 47)

Reference Example B45 ethyl 6-[N-[4-(1H-tetrazol-1-yl)phenyl]sulfamoyl]-1-cyclohexene-1-carboxylate (compound 48)

Reference Example B46 ethyl 6-[N-(4-(1H-1,2,3-triazol-1-yl)phenyl]sulfamoyl]-1-cyclohexene-1-carboxylate (compound 49)

Reference Example B47 ethyl 6-[N-(2-trifluoromethylphenyl)sulfamoyl]-1-cyclohexene-1-carboxylate (compound 50)

Reference Example B48 ethyl 6-[N-(4-methoxycarbonylphenyl)sulfamoyl]-1-cyclohexene-1-carboxylate (compound 51)

Reference Example B49 benzyl 6-[N-(2,4-difluorophenyl)sulfamoyl]-1-cyclohexene-1-carboxylate (compound 52)

Reference Example B50 ethyl 6-[N-[4-[2,3-bis(tert-butoxycarbonyl)guanidinomethyl]phenyl]sulfamoyl]-1-cyclohexene-1-carboxylate (compound 53)

Reference Example B51 ethyl 6-[N-(2-chloro-4-methoxycarbonylphenyl)sulfamoyl]-1-cyclohexene-1-carboxylate (compound 54)

Reference Example B52 ethyl 6-[N-(2-chloro-4-cyanophenyl)sulfamoyl]-1-cyclohexene-1-carboxylate (compound 55)

Reference Example B53 2-hydroxyethyl 6-[N-(2,4-difluorophenyl)sulfamoyl]-1-cyclohexene-1-carboxylate (compound 56)

Reference Example B54 ethyl 6-[N-[2-fluoro-4-(1H-1,2,4-triazol-1-yl)phenyl]sulfamoyl]-1-cyclohexene-1-carboxylate (compound 57)
Reference Example B55 ethyl 2-[N-(2,4-difluorophenyl)sulfamoyl]-1-cyclopentene-1-carboxylate (compound 66)
ethyl 5-[N-(2,4-difluorophenyl)sulfamoyl]-1-cyclopentene-1-carboxylate (compound 58)
Reference Example B56 tert-butyl [6-[N-(2,4-difluorophenyl)sulfamoyl]-1-cyclohexen-1-yl]carbonyloxyacetate (compound 59)
Reference Example B57 [6-[N-(2,4-difluorophenyl)sulfamoyl]-1-cyclohexen-1-yl]carbonyloxyacetic acid (compound 60)
Reference Example B58 ethyl 7-[N-(2,4-difluorophenyl)sulfamoyl]-1-cycloheptene-1-carboxylate (compound 61)
Reference Example B59 ethyl 6-[N-[2-chloro-4-(N-tert-butoxycarbonylmethylcarbamoyl)phenyl]sulfamoyl]-1-cyclohexene-1-carboxylate (compound 62)
Reference Example B60 ethyl 6-[N-[2-chloro-4-(N-ethoxycarbonylmethylcarbamoyl)phenyl]sulfamoyl]-1-cyclohexene-1-carboxylate (compound 63)
Reference Example B61 ethyl 5-[N-(2-chloro-4-fluorophenyl)sulfamoyl]-1-cyclopentene-1-carboxylate (compound 64).
Reference Example B62 2-[4-(2,2,3,3,3-pentafluoropropoxy)phenyl]-4,5,6,7-tetrahydro-1,2-benzisothiazol-3(2H)-one 1,1-dioxide (compound 69)
Reference Example B63 ethyl 7-[N-(2-chloro-4-fluorophenyl)sulfamoyl]-1-dycloheptene-1-carboxylate (compound 65)
Reference Example B64 2-(2,4-difluorophenyl)-5,6,7,7a-tetrahydro-1,2-benzisothiazol-3(2H)-one 1,1-dioxide (compound 70)
Reference Example B65 ethyl 6-[N-(2-chloro-4-fluorophenyl)sulfamoyl]-1-cyclohexene-1-carboxylate (compound 29)
Reference Example B66 1-ethyl 6-[N-(2-chloro-4-fluorophenyl)sulfamoyl]-1-cyclohexene-1-carboxylate (compound 71)
d-ethyl 6-[N-(2-chloro-4-fluorophenyl)sulfamoyl]-1-cyclohexene-1-carboxylate (compound 72)
Reference Example B67 ethyl 6-[N-(2-bromo-4-fluorophenyl)sulfamoyl]-1-cyclohexene-1-carboxylate (compound 73)
Reference Example B68 ethyl 6-[N-(4-bromo-2-chlorophenyl)sulfamoyl]-1-cyclohexene-1-carboxylate (compound 74)
Reference Example B69 high polarity diastereomer (compound 75) and low polarity diastereomer (compound 76) of ethyl 6-[N-(2,4-difluorophenyl)sulfamoyl]-3-phenyl-1-cyclohexene-1-carboxylate
Reference Example B70 high polarity diastereomer (compound 77) and low polarity diastereomer (compound 78) of ethyl 6-[N-(2-chloro-4-fluorophenyl)sulfamoyl]-3-phenyl-1-cyclohexene-1-carboxylate
Reference Example B71 high polarity diastereomer (compound 79) and low polarity diastereomer (compound 80) of ethyl 6-[N-(2,4-difluorophenyl)sulfamoyl]-3-tert-butyl-1-cyclohexene-1-carboxylate
Reference Example B72 high polarity diastereomer (compound 81) and low polarity diastereomer (compound 82) of ethyl 6-[N-(2-chloro-4-fluorophenyl)sulfamoyl]-3-tert-butyl-1-cyclohexene-1-carboxylate
Reference Example B73 ethyl 6-[N-(2,4-difluorophenyl)sulfamoyl]-3,3-dimethyl-1-cyclohexene-1-carboxylate (compound 83)
Reference Example B74 ethyl 6-[N-(2-chloro-4-fluorophenyl)sulfamoyl]-3,3-dimethyl-1-cyclohexene-1-carboxylate (compound 84)
Reference Example B75 ethyl 3-bromo-6-[N-(2,4-difluorophenyl)sulfamoyl]-1-cyclohexene-1-carboxylate (compound 85)

Specific examples are shown in Tables 1-12.

TABLE 1

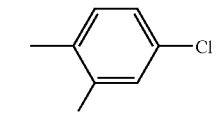

| Compound No. | $R^1$ | $R^2$ | Ar | n |
|---|---|---|---|---|
| 1 | $C_2H_5$ | H | 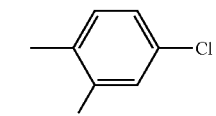 4-Cl, 2-F phenyl | 2 |
| 2 | $C_2H_5$ | $CH_3$ | 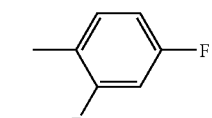 4-Cl, 2-F phenyl | 2 |
| 3 | $C_2H_5$ | H | 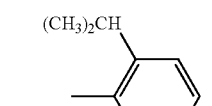 4-F, 2-F phenyl | 2 |
| 4 | $C_2H_5$ | H | 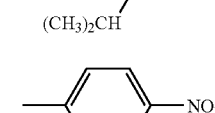 2,6-di(isopropyl)phenyl | 2 |
| 5 | $C_2H_5$ | H | 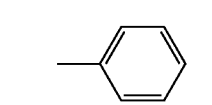 4-$NO_2$ phenyl | 2 |
| 6 | $C_2H_5$ | H | 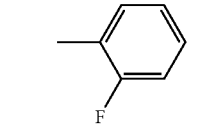 phenyl | 2 |
| 10 | $C_2H_5$ | H | 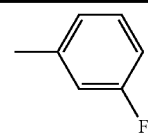 3-F phenyl | 2 |

TABLE 2

| 11 | $C_2H_5$ | H | 3-F phenyl | 2 |

TABLE 2-continued
| 12 | C₂H₅ | H | 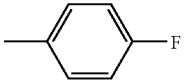 | 2 |
| 13 | C₂H₅ | H | 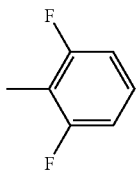 | 2 |
| 14 | C₂H₅ | H | 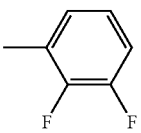 | 2 |
| 15 | C₂H₅ | H | 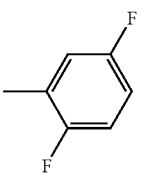 | 2 |
| 16 | C₂H₅ | H | 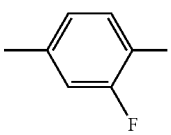 | 2 |
| 17 | C₂H₅ | H | 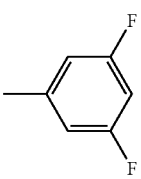 | 2 |
| 19 (l-compound) | C₂H₅ | H | 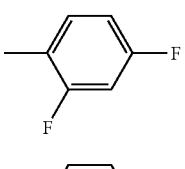 | 2 |
| 20 (d-compound) | C₂H₅ | H | 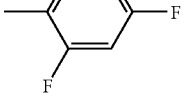 | 2 |
TABLE 3
| 21 | C₂H₅ | H |  | 2 |
| 22 | CH₃ | H | 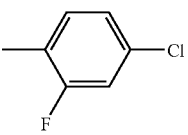 | 2 |
TABLE 3-continued
| 23 | (CH₂)₂CH₃ | H | 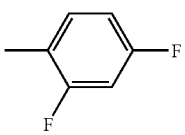 | 2 |
| 24 | CH₃ | H | 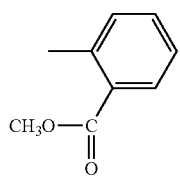 | 2 |
| 25 | CH(CH₃)₂ | H | 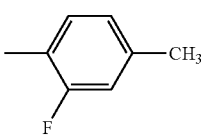 | 2 |
| 26 | C₂H₅ | H | 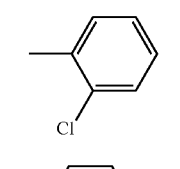 | 2 |
| 27 | C₂H₅ | H | 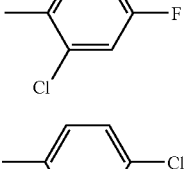 | 2 |
| 28 | C₂H₅ | H | 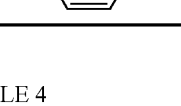 | 2 |
| 29 | C₂H₅ | H | 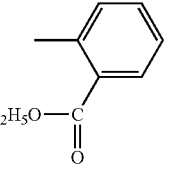 | 2 |
| 30 | C₂H₅ | H | 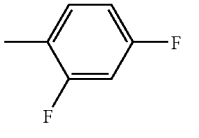 | 2 |
TABLE 4
| 31 | C₂H₅ | H |  | 2 |
| 32 | CH₂CH(CH₃)₂ | H | 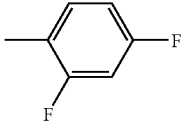 | 2 |
| 33 | (CH₂)₃CH₃ | H | 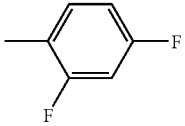 | 2 |

TABLE 4-continued

| | | | | |
|---|---|---|---|---|
| 34 | C₂H₅ | H | 4-bromo-2-fluorophenyl (methyl substituted) | 2 |
| 35 | C₂H₅ | H | 2,4-dichlorophenyl (methyl substituted) | 2 |
| 36 | C₂H₅ | H | 2-acetylphenyl (methyl substituted) | 2 |
| 37 | C₂H₅ | H | 3-chlorophenyl (methyl substituted) | 2 |
| 38 | C₂H₅ | H | 2,3-dichlorophenyl (methyl substituted) | 2 |
| 39 | C₂H₅ | H | 2-ethylphenyl (methyl substituted) | 2 |
| 40 | C₂H₅ | H | 4-(2H-1,2,3-triazol-2-yl)phenyl (methyl substituted) | 2 |

TABLE 5

| | | | | |
|---|---|---|---|---|
| 41 | C₂H₅ | H | 2,5-dichlorophenyl (methyl substituted) | 2 |
| 42 | C₂H₅ | H | 2-(trifluoromethoxy)phenyl (methyl substituted) | 2 |
| 43 | C₂H₅ | H | 2,4,5-trifluorophenyl (methyl substituted) | 2 |

TABLE 5-continued

| | | | | |
|---|---|---|---|---|
| 44 | C₂H₅ | H | 4-(1H-tetrazol-1-yl)phenyl (methyl substituted) | 2 |
| 45 | C₂H₅ | H | 3-chloro-4-methylphenyl (methyl substituted) | 2 |
| 46 | C₂H₅ | H | 4-fluoro-2-methylphenyl (methyl substituted) | 2 |
| 47 | C₂H₅ | H | 2,6-dichlorophenyl (methyl substituted) | 2 |
| 48 | C₂H₅ | H | 4-(1H-tetrazol-1-yl)phenyl (methyl substituted) | 2 |
| 49 | C₂H₅ | H | 4-(1H-1,2,3-triazol-1-yl)phenyl (methyl substituted) | 2 |
| 50 | C₂H₅ | H | 2-(trifluoromethyl)phenyl (methyl substituted) | 2 |

TABLE 6
| # | R1 | R2 | Ar | n |
|---|---|---|---|---|
| 51 | C$_2$H$_5$ | H | 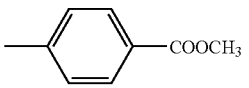 4-methyl, COOCH$_3$ | 2 |
| 52 | CH$_2$-phenyl | H | 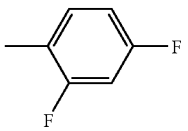 2-methyl, 3-F, 5-F | 2 |
| 53 | C$_2$H$_5$ | H | 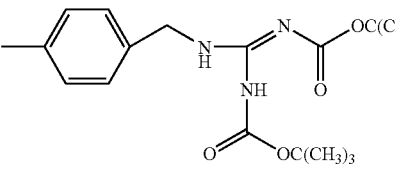 4-methylbenzyl-NH-C(=N-COOC(CH$_3$)$_3$)-NH-COOC(CH$_3$)$_3$ | 2 |
| 54 | C$_2$H$_5$ | H | 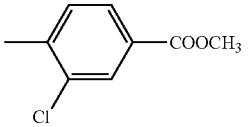 4-methyl, 3-Cl, COOCH$_3$ | 2 |
| 55 | C$_2$H$_5$ | H | 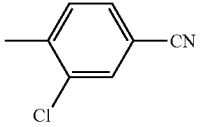 4-methyl, 3-Cl, CN | 2 |
| 56 | (CH$_2$)$_2$OH | H | 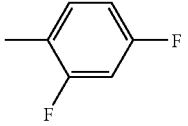 2-methyl, 3-F, 5-F | 2 |
| 57 | C$_2$H$_5$ | H | 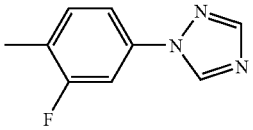 4-methyl, 3-F, 1,2,4-triazolyl | 2 |
| 58 | C$_2$H$_5$ | H | 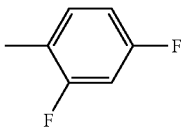 2-methyl, 3-F, 5-F | 1 |
| 59 | CH$_2$COOC(CH$_3$)$_3$ | H | 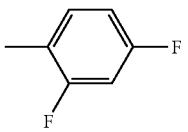 2-methyl, 3-F, 5-F | 2 |
| 60 | CH$_2$COOH | H | 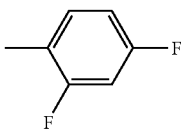 2-methyl, 3-F, 5-F | 2 |
TABLE 7
| # | R1 | R2 | Ar | n |
|---|---|---|---|---|
| 61 | C$_2$H$_5$ | H | 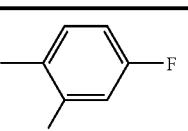 2-methyl, 3-F, 5-F | 3 |
| 62 | C$_2$H$_5$ | H | 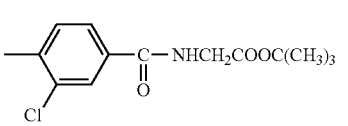 4-methyl, 3-Cl, C(=O)-NHCH$_2$COOC(CH$_3$)$_3$ | 2 |

TABLE 7-continued

| | | | | |
|---|---|---|---|---|
| 63 | $C_2H_5$ | H | 4-methyl-3-chloro-phenyl-C(O)-NHCH$_2$COOC$_2$H$_5$ | 2 |
| 64 | $C_2H_5$ | H | 2-chloro-4-fluoro-methylphenyl | 1 |
| 65 | $C_2H_5$ | H | 2-chloro-4-fluoro-methylphenyl | 3 |
| 71 (l-compound) | $C_2H_5$ | H | 2-chloro-4-fluoro-methylphenyl | 2 |
| 72 (d-compound) | $C_2H_5$ | H | 2-chloro-4-fluoro-methylphenyl | 2 |
| 73 | $C_2H_5$ | H | 2-bromo-4-fluoro-methylphenyl | 2 |
| 74 | $C_2H_5$ | H | 3-chloro-4-methyl-bromo-phenyl | 2 |

TABLE 8

Structure:

$$\text{(CH}_2)_n\text{ with C=C bearing ethyl groups, C(O)OR}^1\text{ and SO}_2\text{NH-Ar}$$

| Compound No. | $R^1$ | Ar | n |
|---|---|---|---|
| 7 | $C_2H_5$ | phenyl | 2 |
| 8 | $C_2H_5$ | 4-methoxyphenyl | 2 |
| 9 | $C_2H_5$ | 4-chloro-3-fluoro-phenyl | 2 |

TABLE 8-continued

| Compound No. | $R^1$ | Ar | n |
|---|---|---|---|
| 18 | $C_2H_5$ | 4-fluorophenyl | 2 |
| 66 | $C_2H_5$ | 2,4-difluorophenyl | 1 |

TABLE 9

Structure: bicyclic with C=O, N-Ar, SO$_2$, cyclohexene ring with two methyl groups

| Compound No. | | Ar |
|---|---|---|
| 67 | cyclohexene-dimethyl | 4-methoxyphenyl |
| 68 | cyclohexene-dimethyl | 4-fluorophenyl |
| 69 | cyclohexene-dimethyl | 4-OCH$_2$CF$_2$CF$_3$-phenyl |
| 70 | cyclohexene-dimethyl | 2,4-difluorophenyl |

TABLE 10

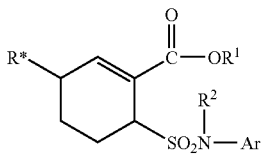

| Compound No. | R¹ | R² | R* | Ar | |
|---|---|---|---|---|---|
| 75 (high polarity diastereomer) | $C_2H_5$ | H | | phenyl | 2,4-difluorophenyl |
| 76 (low polarity diastereomer) | $C_2H_5$ | H | | phenyl | 2,4-difluorophenyl |
| 77 (high polarity diastereomer) | $C_2H_5$ | H | | phenyl | 2-chloro-4-fluorophenyl |
| 78 (low polarity diastereomer) | $C_2H_5$ | H | | phenyl | 2-chloro-4-fluorophenyl |
| 79 (high polarity diastereomer) | $C_2H_5$ | H | $C(CH_3)_3$ | | 3,4-difluorophenyl |
| 80 (low polarity diastereomer) | $C_2H_5$ | H | $C(CH_3)_3$ | | 3,4-difluorophenyl |
| 81 (high polarity diastereomer) | $C_2H_5$ | H | $C(CH_3)_3$ | | 3-chloro-4-fluorophenyl |

TABLE 11

| 82 (low polarity diastereomer) | $C_2H_5$ | H | $C(CH_3)_3$ | | 3-chloro-4-fluorophenyl |
| 85 | $C_2H_5$ | H | Br | | 3,4-difluorophenyl |

TABLE 12

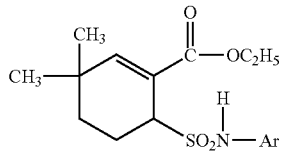

| Compound No. | Ar |
|---|---|
| 83 | 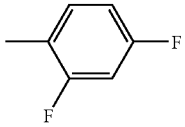 2,4-difluorophenyl |
| 84 | 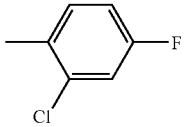 2-chloro-4-fluorophenyl |

Example 1

| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | dimyristoylphosphatidylglycerol | 1 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dimyristoylphosphatidylglycerol (2 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 μm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 2

| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | dimyristoylphosphatidylglycerol | 2 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dimyristoylphosphatidylglycerol (4 mg) are dissolved/dispersed in distilled water (125 ml) at 60°

C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 μm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 3

| 1) | compound 72 of Reference Example B66 | 1000 mg |
|---|---|---|
| 2) | soybean oil | 20 g |
| 3) | purified egg yolk lecithin | 1.2 g |
| 4) | glycerine | 2.25 g |
| 5) | dimyristoylphosphatidylglycerol | 5 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dimyristoylphosphatidylglycerol (10 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 μm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 4

| 1) | compound 72 of Reference Example B66 | 1000 mg |
|---|---|---|
| 2) | soybean oil | 20 g |
| 3) | purified egg yolk lecithin | 1.2 g |
| 4) | glycerine | 2.25 g |
| 5) | dimyristoylphosphatidylglycerol | 10 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dimyristoylphosphatidylglycerol (20 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 μm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 5

| 1) | compound 72 of Reference Example B66 | 1000 mg |
|---|---|---|
| 2) | soybean oil | 20 g |
| 3) | purified egg yolk lecithin | 1.2 g |
| 4) | glycerine | 2.25 g |
| 5) | dimyristoylphosphatidylglycerol | 20 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dimyristoylphosphatidylglycerol (40 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 μm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 6

| 1) | compound 72 of Reference Example B66 | 1000 mg |
|---|---|---|
| 2) | soybean oil | 20 g |
| 3) | purified egg yolk lecithin | 1.2 g |
| 4) | glycerine | 2.25 g |
| 5) | dipalmitoylphosphatidylglycerol | 1 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dipalmitoylphosphatidylglycerol (2 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 μm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 7

| 1) | compound 72 of Reference Example B66 | 1000 mg |
|---|---|---|
| 2) | soybean oil | 20 g |
| 3) | purified egg yolk lecithin | 1.2 g |

-continued

| | | | |
|---|---|---|---|
| 4) | glycerine | 2.25 | g |
| 5) | dipalmitoylphosphatidylglycerol | 2 | mg |
| 6) | distilled water total amount | 100 | ml |

Compound 72 (2000 mg) of Reference Example B66 is dissolved in soybean oil (40 g). Glycerine (4.5 g), purified egg yolk lecithin (2.4 g) and dipalmitoylphosphatidylglycerol (4 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 μm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 8

| | | | |
|---|---|---|---|
| 1) | compound 72 of Reference Example B66 | 1000 | mg |
| 2) | soybean oil | 20 | g |
| 3) | purified egg yolk lecithin | 1.2 | g |
| 4) | glycerine | 2.25 | g |
| 5) | dipalmitoylphosphatidylglycerol | 5 | mg |
| 6) | distilled water total amount | 100 | ml |

Compound 72 (2000 mg) of Reference Example B66 is dissolved in soybean oil (40 g). Glycerine (4.5 g), purified egg yolk lecithin (2.4 g) and dipalmitoylphosphatidylglycerol (10 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 μm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 9

| | | | |
|---|---|---|---|
| 1) | compound 72 of Reference Example B66 | 1000 | mg |
| 2) | soybean oil | 20 | g |
| 3) | purified egg yolk lecithin | 1.2 | g |
| 4) | glycerine | 2.25 | g |
| 5) | dipalmitoylphosphatidylglycerol | 10 | mg |
| 6) | distilled water total amount | 100 | ml |

Compound 72 (2000 mg) of Reference Example B66 is dissolved in soybean oil (40 g). Glycerine (4.5 g), purified egg yolk lecithin (2.4 g) and dipalmitoylphosphatidylglycerol (20 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 μm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 10

| | | | |
|---|---|---|---|
| 1) | compound 72 of Reference Example B66 | 1000 | mg |
| 2) | soybean oil | 20 | g |
| 3) | purified egg yolk lecithin | 1.2 | g |
| 4) | glycerine | 2.25 | g |
| 5) | dipalmitoylphosphatidylglycerol | 20 | mg |
| 6) | distilled water total amount | 100 | ml |

Compound 72 (2000 mg) of Reference Example B66 is dissolved in soybean oil (40 g). Glycerine (4.5 g), purified egg yolk lecithin (2.4 g) and dipalmitoylphosphatidylglycerol (40 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer. (Mizuho) at 15000 psi pressure for 40 minutes, the crude emulsion is finely emulsified. The obtained emulsion composition is passed through a membrane filter (Millipore Sterivex-HV) having a pore size of 0.45 μm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 11

| | | | |
|---|---|---|---|
| 1) | compound 72 of Reference Example B66 | 1000 | mg |
| 2) | soybean oil | 20 | g |
| 3) | purified egg yolk lecithin | 1.2 | g |
| 4) | glycerine | 2.25 | g |
| 5) | distearoylphosphatidylglycerol | 1 | mg |
| 6) | distilled water total amount | 100 | ml |

Compound 72 (2000 mg) of Reference Example B66 is dissolved in soybean oil (40 g). Glycerine (4.5 g), purified egg yolk lecithin (2.4 g) and distearoylphosphatidylglycerol (2 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 μm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 12

| | | |
|---|---|---|
| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | distearoylphosphatidylglycerol | 2 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and distearoylphosphatidylglycerol (4 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 μm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 13

| | | |
|---|---|---|
| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | distearoylphosphatidylglycerol | 5 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and distearoylphosphatidylglycerol (10 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 μm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 14

| | | |
|---|---|---|
| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | distearoylphosphatidylglycerol | 10 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and distearoylphosphatidylglycerol (20 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 μm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 15

| | | |
|---|---|---|
| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | distearoylphosphatidylglycerol | 20 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and distearoylphosphatidylglycerol (40 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 μm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 16

| | | |
|---|---|---|
| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | dioleoylphosphatidylglycerol | 1 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dioleoylphosphatidylglycerol (2 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 µm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 17

| 1) | compound 72 of Reference Example B66 | 1000 mg |
|---|---|---|
| 2) | soybean oil | 20 g |
| 3) | purified egg yolk lecithin | 1.2 g |
| 4) | glycerine | 2.25 g |
| 5) | dioleoylphosphatidylglycerol | 2 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dioleoylphosphatidylglycerol (4 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 µm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 18

| 1) | compound 72 of Reference Example B66 | 1000 mg |
|---|---|---|
| 2) | soybean oil | 20 g |
| 3) | purified egg yolk lecithin | 1.2 g |
| 4) | glycerine | 2.25 g |
| 5) | dioleoylphosphatidylglycerol | 5 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dioleoylphosphatidylglycerol (10 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 µm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 19

| 1) | compound 72 of Reference Example B66 | 1000 mg |
|---|---|---|
| 2) | soybean oil | 20 g |
| 3) | purified egg yolk lecithin | 1.2 g |
| 4) | glycerine | 2.25 g |
| 5) | dioleoylphosphatidylglycerol | 10 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dioleoylphosphatidylglycerol (20 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 µm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 20

| 1) | compound 72 of Reference Example B66 | 1000 mg |
|---|---|---|
| 2) | soybean oil | 20 g |
| 3) | purified egg yolk lecithin | 1.2 g |
| 4) | glycerine | 2.25 g |
| 5) | dioleoylphosphatidylglycerol | 20 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dioleoylphosphatidylglycerol (40 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 µm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 21

| 1) | compound 72 of Reference Example B66 | 1000 mg |
|---|---|---|
| 2) | soybean oil | 20 g |
| 3) | purified egg yolk lecithin | 1.2 g |

| | | | |
|---|---|---|---|
| 4) | glycerine | 2.25 | g |
| 5) | oleoylpalmitoylphosphatidylglycerol | 1 | mg |
| 6) | distilled water total amount | 100 | ml |

Compound 72 (2000 mg) of Reference Example B66 is dissolved in soybean oil (40 g). Glycerine (4.5 g), purified egg yolk lecithin (2.4 g) and oleoylpalmitoylphosphatidylglycerol (2 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 μm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 22

| | | | |
|---|---|---|---|
| 1) | compound 72 of Reference Example B66 | 1000 | mg |
| 2) | soybean oil | 20 | g |
| 3) | purified egg yolk lecithin | 1.2 | g |
| 4) | glycerine | 2.25 | g |
| 5) | oleoylpalmitoylphosphatidylglycerol | 2 | mg |
| 6) | distilled water total amount | 100 | ml |

Compound 72 (2000 mg) of Reference Example B66 is dissolved in soybean oil (40 g). Glycerine (4.5 g), purified egg yolk lecithin (2.4 g) and oleoylpalmitoylphosphatidylglycerol (4 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 μm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 23

| | | | |
|---|---|---|---|
| 1) | compound 72 of Reference Example B66 | 1000 | mg |
| 2) | soybean oil | 20 | g |
| 3) | purified egg yolk lecithin | 1.2 | g |
| 4) | glycerine | 2.25 | g |
| 5) | oleoylpalmitoylphosphatidylglycerol | 5 | mg |
| 6) | distilled water total amount | 100 | ml |

Compound 72 (2000 mg) of Reference Example B66 is dissolved in soybean oil (40 g). Glycerine (4.5 g), purified egg yolk lecithin (2.4 g) and oleoylpalmitoylphosphatidylglycerol (10 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 μm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 24

| | | | |
|---|---|---|---|
| 1) | compound 72 of Reference Example B66 | 1000 | mg |
| 2) | soybean oil | 20 | g |
| 3) | purified egg yolk lecithin | 1.2 | g |
| 4) | glycerine | 2.25 | g |
| 5) | oleoylpalmitoylphosphatidylglycerol | 10 | mg |
| 6) | distilled water total amount | 100 | ml |

Compound 72 (2000 mg) of Reference Example B66 is dissolved in soybean oil (40 g). Glycerine (4.5 g), purified egg yolk lecithin (2.4 g) and oleoylpalmitoylphosphatidylglycerol (20 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 μm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 25

| | | | |
|---|---|---|---|
| 1) | compound 72 of Reference Example B66 | 1000 | mg |
| 2) | soybean oil | 20 | g |
| 3) | purified egg yolk lecithin | 1.2 | g |
| 4) | glycerine | 2.25 | g |
| 5) | oleoylpalmitoylphosphatidylglycerol | 20 | mg |
| 6) | distilled water total amount | 100 | ml |

Compound 72 (2000 mg) of Reference Example B66 is dissolved in soybean oil (40 g). Glycerine (4.5 g), purified egg yolk lecithin (2.4 g) and oleoylpalmitoylphosphatidylglycerol (40 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 µm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 26

| | | |
|---|---|---|
| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | dioctanoylphosphatidic acid | 1 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dioctanoylphosphatidic acid (2 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 µm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 27

| | | |
|---|---|---|
| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | dioctanoylphosphatidic acid | 2 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dioctanoylphosphatidic acid (4 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 µm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 28

| | | |
|---|---|---|
| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | dioctanoylphosphatidic acid | 5 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dioctanoylphosphatidic acid (10 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 µm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 29

| | | |
|---|---|---|
| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | dioctanoylphosphatidic acid | 10 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dioctanoylphosphatidic acid (20 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 µm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 30

| | | |
|---|---|---|
| 1) | compound 72 of Reference Example B66 | 1000 mg |
| 2) | soybean oil | 20 g |
| 3) | purified egg yolk lecithin | 1.2 g |

-continued

| 4) | glycerine | 2.25 g |
| 5) | dioctanoylphosphatidic acid | 20 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dioctanoylphosphatidic acid (40 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 μm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 31

| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | didecanoylphosphatidic acid | 1 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and didecanoylphosphatidic acid (2 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 μm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 32

| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | didecanoylphosphatidic acid | 2 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and didecanoylphosphatidic acid (4 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 μm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 33

| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | didecanoylphosphatidic acid | 5 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and didecanoylphosphatidic acid (10 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 μm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 34

| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | didecanoylphosphatidic acid | 10 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and didecanoylphosphatidic acid (20 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 μm, and filled in 2 ml ampoules by 2 ml. After nitrogen displacement, the ampoules are heat-sealed. The ampoules are sterilized in an autoclave at

Example 35

| | | |
|---|---|---|
| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | didecanoylphosphatidic acid | 20 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and didecanoylphosphatidic acid (40 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 µm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 36

| | | |
|---|---|---|
| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | dilauroylphosphatidic acid | 1 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dilauroylphosphatidic acid (2 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 µm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 37

| | | |
|---|---|---|
| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | dilauroylphosphatidic acid | 2 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dilauroylphosphatidic acid (4 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 µm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 38

| | | |
|---|---|---|
| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | dilauroylphosphatidic acid | 5 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dilauroylphosphatidic acid (10 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 µm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 39

| | | |
|---|---|---|
| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | dilauroylphosphatidic acid | 10 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dilauroylphosphatidic acid (20 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 µm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 40

| 1) | compound 72 of Reference Example B66 | 1000 mg |
|---|---|---|
| 2) | soybean oil | 20 g |
| 3) | purified egg yolk lecithin | 1.2 g |
| 4) | glycerine | 2.25 g |
| 5) | dilauroylphosphatidic acid | 20 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dilauroylphosphatidic acid (40 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 µm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 41

| 1) | compound 72 of Reference Example B66 | 1000 mg |
|---|---|---|
| 2) | soybean oil | 20 g |
| 3) | purified egg yolk lecithin | 1.2 g |
| 4) | glycerine | 2.25 g |
| 5) | dimyristoylphosphatidic acid | 1 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dimyristoylphosphatidic acid (2 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 µm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 42

| 1) | compound 72 of Reference Example B66 | 1000 mg |
|---|---|---|
| 2) | soybean oil | 20 g |
| 3) | purified egg yolk lecithin | 1.2 g |
| 4) | glycerine | 2.25 g |
| 5) | dimyristoylphosphatidic acid | 2 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dimyristoylphosphatidic acid (4 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 µm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 43

| 1) | compound 72 of Reference Example B66 | 1000 mg |
|---|---|---|
| 2) | soybean oil | 20 g |
| 3) | purified egg yolk lecithin | 1.2 g |
| 4) | glycerine | 2.25 g |
| 5) | dimyristoylphosphatidic acid | 5 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dimyristoylphosphatidic acid (10 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 µm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 44

| 1) | compound 72 of Reference Example B66 | 1000 mg |
|---|---|---|
| 2) | soybean oil | 20 g |
| 3) | purified egg yolk lecithin | 1.2 g |

-continued

| | | |
|---|---|---|
| 4) | glycerine | 2.25 g |
| 5) | dimyristoylphosphatidic acid | 10 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dimyristoylphosphatidic acid (20 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 μm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 45

| | | |
|---|---|---|
| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | dimyristoylphosphatidic acid | 20 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dimyristoylphosphatidic acid (40 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 μm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 46

| | | |
|---|---|---|
| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | dipalmitoylphosphatidic acid | 1 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dipalmitoylphosphatidic acid (2 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 μm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 47

| | | |
|---|---|---|
| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | dipalmitoylphosphatidic acid | 2 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dipalmitoylphosphatidic acid (4 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 μm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 48

| | | |
|---|---|---|
| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | dipalmitoylphosphatidic acid | 5 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dipalmitoylphosphatidic acid (10 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 μm, and filled in 2 ml ampoules by 2 ml. After nitrogen displacement, the ampoules are heat-sealed. The ampoules are sterilized in an autoclave at

Example 49

| | | |
|---|---|---|
| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | dipalmitoylphosphatidic acid | 10 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dipalmitoylphosphatidic acid (20 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 µm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 50

| | | |
|---|---|---|
| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | dipalmitoylphosphatidic acid | 20 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dipalmitoylphosphatidic acid (40 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 µm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 51

| | | |
|---|---|---|
| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | distearoylphosphatidic acid | 1 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and distearoylphosphatidic acid (2 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 µm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 52

| | | |
|---|---|---|
| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | distearoylphosphatidic acid | 2 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and distearoylphosphatidic acid (4 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 µm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 53

| | | |
|---|---|---|
| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | distearoylphosphatidic acid | 5 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and distearoylphosphatidic acid (10 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 µm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 54

| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | distearoylphosphatidic acid | 10 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and distearoylphosphatidic acid (20 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 µm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 55

| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | distearoylphosphatidic acid | 20 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and distearoylphosphatidic acid (40 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 µm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 56

| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | dioleoylphosphatidic acid | 1 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dioleoylphosphatidic acid (2 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 µm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 57

| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | dioleoylphosphatidic acid | 2 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dioleoylphosphatidic acid (4 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 µm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 58

| 1) | compound 72 of Reference Example B66 | 1000 mg |
| 2) | soybean oil | 20 g |
| 3) | purified egg yolk lecithin | 1.2 g |

-continued

| 4) | glycerine | 2.25 g |
| 5) | dioleoylphosphatidic acid | 5 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dioleoylphosphatidic acid (10 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 μm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 59

| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | dioleoylphosphatidic acid | 10 mg |
| 6) | distilled water total amount | 100 ml |

Compound 72 (2000 mg) of Reference Example B66 is dissolved in soybean oil (46 g). Glycerine (4.5 g), purified egg yolk lecithin (2.4 g) and dioleoylphosphatidic acid (20 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 μm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 60

| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | dioleoylphosphatidic acid | 20 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dioleoylphosphatidic acid (40 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 μm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 61

| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | dipalmitoylphosphatidylserine | 1 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dipalmitoylphosphatidylserine (2 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 μm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 62

| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | dipalmitoylphosphatidylserine | 2 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dipalmitoylphosphatidylserine (4 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 μm, and filled in 2 ml ampoules by 2 ml. After nitrogen displacement, the ampoules are heat-sealed. The ampoules are sterilized in an autoclave at

Example 63

| | | |
|---|---|---|
| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | dipalmitoylphosphatidylserine | 5 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dipalmitoylphosphatidylserine (10 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 μm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 64

| | | |
|---|---|---|
| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | dipalmitoylphosphatidylserine | 10 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dipalmitoylphosphatidylserine (20 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 μm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 65

| | | |
|---|---|---|
| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | dipalmitoylphosphatidylserine | 20 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dipalmitoylphosphatidylserine (40 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 μm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 66

| | | |
|---|---|---|
| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | dioleoylphosphatidylserine | 1 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dioleoylphosphatidylserine (2 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 μm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 67

| | | |
|---|---|---|
| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | dioleoylphosphatidylserine | 2 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dioleoylphosphatidylserine (4 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 µm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 68

| 1) | compound 72 of Reference Example B66 | 1000 mg |
|---|---|---|
| 2) | soybean oil | 20 g |
| 3) | purified egg yolk lecithin | 1.2 g |
| 4) | glycerine | 2.25 g |
| 5) | dioleoylphosphatidylserine | 5 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dioleoylphosphatidylserine (10 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 µm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 69

| 1) | compound 72 of Reference Example B66 | 1000 mg |
|---|---|---|
| 2) | soybean oil | 20 g |
| 3) | purified egg yolk lecithin | 1.2 g |
| 4) | glycerine | 2.25 g |
| 5) | dioleoylphosphatidylserine | 10 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dioleoylphosphatidylserine (20 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 µm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 70

| 1) | compound 72 of Reference Example B66 | 1000 mg |
|---|---|---|
| 2) | soybean oil | 20 g |
| 3) | purified egg yolk lecithin | 1.2 g |
| 4) | glycerine | 2.25 g |
| 5) | dioleoylphosphatidylserine | 20 mg |
| 6) | distilled water total amount | 100 ml |

Compound 72 (2000 mg) of Reference Example B66 is dissolved in soybean oil (40 g). Glycerine (4.5 g), 15' purified egg yolk lecithin (2.4 g) and dioleoylphosphatidylserine (40 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water.

Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 µm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 71

| 1) | compound 72 of Reference Example B66 | 1000 mg |
|---|---|---|
| 2) | soybean oil | 20 g |
| 3) | purified egg yolk lecithin | 1.2 g |
| 4) | glycerine | 2.25 g |
| 5) | dimyristoylphosphatidylglycerol | 200 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dimyristoylphosphatidylglycerol (400 mg) were dissolved/dispersed in distilled water (125 ml) at 60° C. These are mixed and roughly emulsified in a homogenizer Polytron (ULTRA TURRAX) at 16,000/min for 1 min. The volume was adjusted to 200 ml in a measuring cylinder with distilled water. Using a high pressure homogenizer microfluidizer (Mizuho) at 15000 psi pressure for 40 minutes, the crude emulsion was finely emulsified. The obtained emulsion composition was passed through a membrane filter (Millipore Sterivex-HV) having a pore size of 0.45 µm, and filled in 2 ml ampoules by 2 ml. After nitrogen displacement, the ampoules were heat-sealed. The ampoules were sterilized in an autoclave at 121° C. for 15 min to give an emulsion composition having the above-mentioned formulation.

Example 72

| 1) | compound 72 of Reference Example B66 | 1000 mg |
|---|---|---|

-continued

| | | |
|---|---|---|
| 2) | soybean oil | 20 g |
| 3) | purified egg yolk lecithin | 1.2 g |
| 4) | glycerine | 2.25 g |
| 5) | dipalmitoylphosphatidylglycerol | 200 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dipalmitoylphosphatidylglycerol (400 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 µm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 73

| | | |
|---|---|---|
| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | distearoylphosphatidylglycerol | 200 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and distearoylphosphatidylglycerol (400 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 µm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 74

| | | |
|---|---|---|
| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | dioleoylphosphatidylglycerol | 200 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dioleoylphosphatidylglycerol (400 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 µm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 75

| | | |
|---|---|---|
| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | oleoylpalmitoylphosphatidylglycerol | 200 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and oleoylpalmitoylphosphatidylglycerol (400 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 µm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 76

| | | |
|---|---|---|
| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | dioctanoylphosphatidic acid | 200 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dioctanoylphosphatidic acid (400 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 µm, and filled in 2 ml ampoules by 2 ml. After nitrogen displacement, the ampoules

Example 77

| | | |
|---|---|---|
| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | didecanoylphosphatidic acid | 200 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and didecanoylphosphatidic acid (400 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 µm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 78

| | | |
|---|---|---|
| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | dilauroylphosphatidic acid | 200 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dilauroylphosphatidic acid (400 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 µm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 79

| | | |
|---|---|---|
| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | dimyristoylphosphatidic acid | 200 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dimyristoylphosphatidic acid (400 mg) are dissolved/dispersed in distilled water (125 ml) at 60° C.; These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 µm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 80

| | | |
|---|---|---|
| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | dipalmitoylphosphatidic acid | 200 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dipalmitoylphosphatidic acid (400 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 µm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 81

| | | |
|---|---|---|
| 1) | compound 72 of Reference Example B66 | 1000 mg |
| 2) | soybean oil | 20 g |
| 3) | purified egg yolk lecithin | 1.2 g |
| 4) | glycerine | 2.25 g |
| 5) | distearoylphosphatidic acid | 200 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and distearoylphosphatidic acid (400 mg)

are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 μm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 82

| 1) | compound 72 of Reference Example B66 | 1000 mg |
|---|---|---|
| 2) | soybean oil | 20 g |
| 3) | purified egg yolk lecithin | 1.2 g |
| 4) | glycerine | 2.25 g |
| 5) | dioleoylphosphatidic acid | 200 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dioleoylphosphatidic acid (400 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 μm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 83

| 1) | compound 72 of Reference Example B66 | 1000 mg |
|---|---|---|
| 2) | soybean oil | 20 g |
| 3) | purified egg yolk lecithin | 1.2 g |
| 4) | glycerine | 2.25 g |
| 5) | dipalmitoylphosphatidylserine | 200 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dipalmitoylphosphatidylserine (400 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 μm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 84

| 1) | compound 72 of Reference Example B66 | 1000 mg |
|---|---|---|
| 2) | soybean oil | 20 g |
| 3) | purified egg yolk lecithin | 1.2 g |
| 4) | glycerine | 2.25 g |
| 5) | dioleoylphosphatidylserine | 200 mg |
| 6) | distilled water total amount | 100 ml |

Compound 72 (2000 mg) of Reference Example B66 is dissolved in soybean oil (40 g). Glycerine (4.5 g), purified egg yolk lecithin (2.4 g) and dioleoylphosphatidylserine (400 mg) are dissolved/dispersed in distilled water (125 ml) at 60° C. These are mixed and roughly emulsified in a homogenizer Polytron (ULTRA TURRAX) at 16,000/min for 1 min. The volume is adjusted to 200 ml in a measuring cylinder with distilled water. Using a high pressure homogenizer microfluidizer (Mizuho) at 15000 psi pressure for 40 minutes, the crude emulsion is finely emulsified. The obtained emulsion composition is passed through a membrane filter (Millipore Sterivex-HV) having a pore size of 0.45 μm, and filled in 2 ml ampoules by 2 ml. After nitrogen displacement, the ampoules are heat-sealed. The ampoules are sterilized in an autoclave at 121° C. for 15 min to give an emulsion composition having the above-mentioned formulation.

Example 85

| 1) | compound 72 of Reference Example B66 | 1000 mg |
|---|---|---|
| 2) | soybean oil | 20 g |
| 3) | purified egg yolk lecithin | 1.2 g |
| 4) | glycerine | 2.25 g |
| 5) | dimyristoylphosphatidylglycerol | 50 mg |
| 6) | distilled water total amount | 100 ml |

Compound 72 (9452 mg) of Reference Example B66 was dissolved in soybean oil (180 g). Glycerine (20.24 g), purified egg yolk lecithin (10.812 g) and dimyristoylphosphatidylglycerol (452 mg) were dissolved/dispersed in distilled water (560 ml) at 60° C. These were mixed and roughly emulsified in a homogenizer Polytron (ULTRA TURRAX) at 16,000/min for 3 min. The volume was adjusted to 900 ml in a measuring cylinder with distilled water. Using a high pressure homogenizer microfluidizer (Mizuho) at 8000 psi pressure by 6 pass, the crude emulsion was finely emulsified. The obtained emulsion composition was passed through a membrane filter (Acrodisc Gelman) having a pore size of 5 μm, and filled in 20 ml vials by 20 ml. After nitrogen displacement, the vials were tightly sealed. The vials were sterilized in an autoclave at 121° C. for 15 min to give an emulsion composition having the above-mentioned formulation.

Example 86

| 1) | compound 72 of Reference Example B66 | 1000 mg |
|---|---|---|
| 2) | soybean oil | 20 g |
| 3) | purified egg yolk lecithin | 1.2 g |

| | | | |
|---|---|---|---|
| 4) | glycerine | 2.25 | g |
| 5) | dimyristoylphosphatidylglycerol | 100 | mg |
| 6) | distilled water total amount | 100 | ml |

Compound 72 (9451 mg) of Reference Example B66 was dissolved in soybean oil (180 g). Glycerine (20.25 g), purified egg yolk lecithin (10.813 g) and dimyristoylphosphatidylglycerol (905 mg) were dissolved/dispersed in distilled water (560 ml) at 60° C. These were mixed and roughly emulsified in a homogenizer Polytron (ULTRA TURRAX) at 16,000/min for 3 min. The volume was adjusted to 900 ml in a measuring cylinder with distilled water. Using a high pressure homogenizer microfluidizer (Mizuho) at 8000 psi pressure by 6 pass, the crude emulsion was finely emulsified. The obtained emulsion composition was passed through a membrane filter (Acrodisc Gelman) having a pore size of 5 µm, and filled in 20 ml vials by 20 ml. After nitrogen displacement, the vials were tightly sealed. The vials were sterilized in an autoclave at 121° C. for 15 min to give an emulsion composition having the above-mentioned formulation.

Example 87

| | | | |
|---|---|---|---|
| 1) | compound 72 of Reference Example B66 | 1000 | mg |
| 2) | soybean oil | 20 | g |
| 3) | purified egg yolk lecithin | 1.2 | g |
| 4) | glycerine | 2.25 | g |
| 5) | dimyristoylphosphatidylglycerol | 200 | mg |
| 6) | distilled water total amount | 100 | ml |

Compound 72 (3155 mg) of Reference Example B66 was dissolved in soybean oil (60 g). Glycerine (6.76 g), purified egg yolk lecithin (3.645 g) and dimyristoylphosphatidylglycerol (610 mg) were dissolved/dispersed in distilled water (188 ml) at 60° C. These were mixed and roughly emulsified in a homogenizer Polytron (ULTRA TURRAX) at 16,000/min for 3 min. The volume was adjusted to 300 ml in a measuring cylinder with distilled water. Using a high pressure homogenizer microfluidizer (Mizuho) at 15000 psi pressure by 25 pass, the crude emulsion was finely emulsified. The obtained emulsion composition was passed through a membrane filter (Millipore Sterivex-HV) having a pore size of 0.45 µm, and filled in 30 ml vials by 30 ml. After nitrogen displacement, the vials were tightly sealed. The vials were sterilized in an autoclave at 121° C. for 15 min to give an emulsion composition having the above-mentioned formulation.

Example 88

| | | | |
|---|---|---|---|
| 1) | compound 72 of Reference Example B66 | 1000 | mg |
| 2) | soybean oil | 20 | g |
| 3) | purified egg yolk lecithin | 1.2 | g |
| 4) | glycerine | 2.25 | g |
| 5) | dimyristoylphosphatidylglycerol | 500 | mg |
| 6) | distilled water total amount | 100 | ml |

Compound 72 (9452 mg) of Reference Example B66 was dissolved in soybean oil (180 g). Glycerine (20.25 g), purified egg yolk lecithin (10.813 g) and dimyristoylphosphatidylglycerol (4506 mg) were dissolved/dispersed in distilled water (560 ml) at 60° C. These were mixed and roughly emulsified in a homogenizer Polytron (ULTRA TURRAX) at 16,000/min for 3 min. The volume was adjusted to 900 ml in a measuring cylinder with distilled water. Using a high pressure homogenizer microfluidizer (Mizuho) at 8000 psi pressure by 6 pass, the crude emulsion was finely emulsified. The obtained emulsion composition was passed through a membrane filter (Acrodisc Gelman) having a pore size of 5 µm, and filled in 20 ml vials by 20 ml. After nitrogen displacement, the vials were tightly sealed. The vials were sterilized in an autoclave at 121° C. for 15 min to give an emulsion composition having the above-mentioned formulation.

Example 89

| | | | |
|---|---|---|---|
| 1) | compound 72 of Reference Example B66 | 1000 | mg |
| 2) | soybean oil | 20 | g |
| 3) | purified egg yolk lecithin | 1.2 | g |
| 4) | glycerine | 2.25 | g |
| 5) | dimyristoylphosphatidylglycerol | 500 | mg |
| 6) | distilled water total amount | 100 | ml |

Compound 72 (9452 mg) of Reference Example B66 was dissolved in soybean oil (180 g). Glycerine (20.26 g), purified egg yolk lecithin (8.119 g) and dimyristoylphosphatidylglycerol (4512 mg) were dissolved/dispersed in distilled water (560 ml) at 60° C. These were mixed and roughly emulsified in a homogenizer Polytron (ULTRA TURRAX) at 16,000/min for 3 min. The volume was adjusted to 900 ml in a measuring cylinder with distilled water. Using a high pressure homogenizer microfluidizer (Mizuho) at 8000 psi pressure by 6 pass, the crude emulsion was finely emulsified. The obtained emulsion composition was passed through a membrane filter (Acrodisc Gelman) having a pore size of 5 µm, and filled in 20 ml vials by 20 ml. After nitrogen displacement, the vials were tightly sealed. The vials were sterilized in an autoclave at 121° C. for 15 min to give an emulsion composition having the above-mentioned formulation.

Example 90

| | | | |
|---|---|---|---|
| 1) | compound 72 of Reference Example B66 | 500 | mg |
| 2) | soybean oil | 20 | g |
| 3) | purified egg yolk lecithin | 1.2 | g |
| 4) | glycerine | 2.25 | g |
| 5) | dimyristoylphosphatidylglycerol | 200 | mg |
| 6) | distilled water total amount | 100 | ml |

Compound 72 (4725 mg) of Reference Example B66 was dissolved in soybean oil (180 g). Glycerine (20.26 g), purified egg yolk lecithin (10.811 g) and dimyristoylphosphatidylglycerol (1811 mg) were dissolved/dispersed in distilled water (560 ml) at 60° C. These were mixed and roughly emulsified in a homogenizer Polytron (ULTRA TURRAX) at 16,000/min for 3 min. The volume was adjusted to 900 ml in a measuring cylinder with distilled water. Using a high pressure homogenizer microfluidizer (Mizuho) at 8000 psi pressure by 6 pass, the crude emulsion was finely emulsified. The obtained emulsion composition was passed through a membrane filter (Acrodisc Gelman) having a pore size of 5 µm, and filled in 20 ml vials by 20 ml. After nitrogen displacement, the vials were tightly sealed. The vials were sterilized in an autoclave at 121° C. for 15 min to give an emulsion composition having the above-mentioned formulation.

Example 91

| 1) | compound 72 of Reference Example B66 | 1000 mg |
|---|---|---|
| 2) | soybean oil | 20 g |
| 3) | purified egg yolk lecithin | 1.2 g |
| 4) | glycerine | 2.25 g |
| 5) | dimyristoylphosphatidylglycerol | 200 mg |
| 6) | distilled water total amount | 100 ml |

Compound 72 (421 mg) of Reference Example B66 was dissolved in soybean oil (8.03 g). Glycerine (0.91 g), purified egg yolk lecithin (0.48 g) and dimyristoylphosphatidylglycerol (80.1 mg) were dissolved/dispersed in distilled water (30 ml) at 60° C. These were mixed and roughly emulsified in a homogenizer Polytron (ULTRA TURRAX) at 16,000/min for 3 min. The volume was adjusted to 40 ml in a measuring cylinder with distilled water. Using a high pressure homogenizer MicronLab40 (APV Gaulin) at 800 bar pressure by 12 pass, the crude emulsion was finely emulsified. The obtained emulsion composition was passed through a membrane filter (Millipore Millex-SV) having a pore size of 5 µm, and filled in 20 ml vials by 15 ml. After nitrogen displacement, the vials were tightly sealed. The vials were sterilized in an autoclave at 121° C. for 15 min to give an emulsion composition having the above-mentioned formulation.

Example 92

| 1) | compound 72 of Reference Example B66 | 1000 mg |
|---|---|---|
| 2) | soybean oil | 20 g |
| 3) | purified egg yolk lecithin | 1.2 g |
| 4) | glycerine | 2.25 g |
| 5) | dipalmitoylphosphatidylglycerol | 200 mg |
| 6) | distilled water total amount | 100 ml |

Compound 72 (421 mg) of Reference Example B66 was dissolved in soybean oil (8.05 g). Glycerine (0.90 g), purified egg yolk lecithin (0.48 g) and dipalmitoylphosphatidylglycerol (81.2 mg) were dissolved/dispersed in distilled water (30 ml) at 60° C. These were mixed and roughly emulsified in a homogenizer Polytron (ULTRA TURRAX) at 16,000/min for 3 min. The volume was adjusted to 40 ml in a measuring cylinder with distilled water. Using a high pressure homogenizer MicronLab40 (APV Gaulin) at 800 bar pressure by 12 pass, the crude emulsion was finely emulsified. The obtained emulsion composition was passed through a membrane filter (Millipore Millex-SV) having a pore size of 5 µm, and filled in 20 ml vials by 15 ml. After nitrogen displacement, the vials were tightly sealed. The vials were sterilized in an autoclave at 121° C. for 15 min to give an emulsion composition having the above-mentioned formulation.

Example 93

| 1) | compound 72 of Reference Example B66 | 1000 mg |
|---|---|---|
| 2) | soybean oil | 20 g |
| 3) | purified egg yolk lecithin | 1.2 g |
| 4) | glycerine | 2.25 g |
| 5) | distearoylphosphatidylglycerol | 200 mg |
| 6) | distilled water total amount | 100 ml |

Compound 72 (420 mg) of Reference Example B66 was dissolved in soybean oil (8.01 g). Glycerine (0.90 g), purified egg yolk lecithin (0.49 g) and distearoylphosphatidylglycerol (79.9 mg) were dissolved/dispersed in distilled water (30 ml) at 60° C. These were mixed and roughly emulsified in a homogenizer Polytron (ULTRA TURRAX) at 16,000/min for 3 min. The volume was adjusted to 40 ml in a measuring cylinder with distilled water. Using a high pressure homogenizer MicronLab40 (APV Gaulin) at 800 bar pressure by 12 pass, the crude emulsion was finely emulsified. The obtained emulsion composition was passed through a membrane filter (Millipore Millex-SV) having a pore size of 5 µm, and filled in 20 ml vials by 15 ml. After nitrogen displacement, the vials were tightly sealed. The vials were sterilized in an autoclave at 121° C. for 15 min to give an emulsion composition having the above-mentioned formulation.

Experiment 1 NO Production-Inhibiting Effect

Mouse macrophage cell line RAW264.7 was used as an iNOS-inducible cell and a test compound was examined for its % inhibition of NO production. The test compound was dissolved at 10 mM in N,N-dimethylformamide and diluted with an RPMI-1640 medium at the concentration of 0.1 mM. The concentration was further adjusted using the medium so that a final concentration ranging from 10 µM to 10 nM could be obtained by a 10-fold serial dilution and the test compound was added to a culture medium. On the day before the experiment, the cell was adjusted at $5 \times 10^5$/ml in an RPMI-1640 medium supplemented with 10% inactivated fetal calf serum and inoculated to a 96-well microplate at $1 \times 10^5$ cells/0.2 ml per well. After incubating at 37° C. under an atmosphere of 5% $CO_2$/95% air overnight, the test compound adjusted as described above was added and then LPS and interferon gamma were added at the final concentrations of 5 ng/ml and 1 U/ml, respectively. After further incubating overnight, culture supernatants were examined for the concentration of nitrite ion (stable metabolite of NO) which was used as an index for the NO production. The nitrite ion concentration was determined by adding 25 µl of 20 µg/ml of 2,3-diaminonaphthalene (DAN) to 50 µl of the culture supernatant, followed by incubating at room temperature for 10 minutes, followed by adding 25 µl of 0.5 N NaOH, followed by determining a fluorescence at 450 nm (excitation wavelength: 365 nm). The results are shown in Tables 13-15. An $IC_{50}$ represents the concentration of the test compound which inhibits 50% of the NO production.

TABLE 13

| Compound No. | $IC_{50}$ (µM) |
|---|---|
| 1 | 0.12-0.32 |
| 2 | 1.1 |
| 3 | 0.013-0.039 |
| 4 | 2.6 |
| 5 | 3.7 |
| 6 | 0.59 |
| 7 | 4.0 |
| 8 | 4.8 |
| 9 | 4.1 |
| 10 | 0.058 |
| 11 | 0.31 |
| 12 | 0.18 |
| 13 | 0.46 |

TABLE 13-continued

| Compound No. | IC$_{50}$ (µM) |
|---|---|
| 14 | 0.59 |
| 15 | 0.28 |
| 16 | 0.18 |
| 17 | 2.6 |
| 18 | 4.4 |
| 19 | 2.0 |
| 20 | 0.005 |
| 21 | 2.4 |
| 22 | 0.18 |
| 23 | 0.027 |
| 24 | 0.78 |
| 25 | 0.32 |
| 26 | 3.3 |

TABLE 14

| | |
|---|---|
| 27 | 0.25 |
| 28 | 0.029 |
| 29 | 0.0093 |
| 30 | 0.54 |
| 31 | 0.23 |
| 32 | 0.23 |
| 33 | 0.26 |
| 34 | 0.35 |
| 35 | 0.082 |
| 36 | 1.5 |
| 37 | 0.13 |
| 38 | 0.041 |
| 39 | 0.32 |
| 40 | 2.5 |
| 41 | 0.24 |
| 42 | 1.1 |
| 43 | 0.073 |
| 44 | 3.7 |
| 45 | 0.027 |
| 46 | 0.054 |
| 47 | 0.048 |
| 48 | 3.8 |
| 49 | 5.6 |
| 50 | 2.0 |
| 51 | 4.0 |
| 52 | 4.3 |
| 53 | 2.4 |
| 54 | 2.3 |

TABLE 15

| | |
|---|---|
| 55 | 3.3 |
| 56 | 1.0 |
| 57 | 4.6 |
| 58 | 0.39 |
| 59 | 0.54 |
| 60 | 7.9 |
| 61 | 2.8 |
| 62 | 3.8 |
| 63 | 8.4 |
| 64 | 0.25 |
| 65 | 0.32 |
| 66 | 8.1 |
| 67 | 6.0 |
| 68 | 5.1 |
| 69 | 6.8 |
| 70 | 0.35 |

In Tables 13-15, Compounds 1 and 3 were tested 7 and 9 times, respectively, and the minimum and the maximum of the IC$_{50}$ were indicated.

Any of the test compounds exhibited a potent inhibitory effect on the NO production by RAW264.7 cell, revealing that an inventive derivative had an excellent NO production-inhibiting effect.

Experiment 2 Cytokine Production-Inhibiting Effect

Using mouse macrophage cell line RAW264.7, a test compound was examined for its % inhibition of a cytokine production. The test compound was dissolved at 10 mM in N,N-dimethylformamide and diluted with an RPMI-1640 medium at the concentration of 0.1 mM. The concentration was further adjusted using the medium so that a final concentration ranging from 10 µM to 10 nM could be obtained by a 10-fold serial dilution and the test compound was added to a culture medium. On the day before the experiment, the cell was adjusted at 5×10$^5$/ml in an RPMI-1640 medium supplemented with 10% inactivated fetal calf serum and inoculated to a 96-well microplate at 1×10$^5$ cells/0.2 ml per well. After incubating at 37° C. under an atmosphere of 5% CO$_2$/95% air overnight, the test compound adjusted as described above was added and then LPS and interferon-gamma were added at the final concentrations of 5 ng/ml and 1 U/ml, respectively. After further incubating overnight, culture supernatants were examined for the concentrations of TNF-α and IL-6. IL-1α was determined using 1.0 µg/ml of LPS in the absence of interferon gamma under otherwise similar conditions. Each cytokine was determined using an assay kit manufactured by Amersham. The results are shown in Table 16. An IC$_{50}$ represents the concentration of the test compound which inhibits 50% of the cytokine production.

TABLE 16

| | IC$_{50}$ (µM) | | |
|---|---|---|---|
| Compound No. | TNF-α | IL-1α | IL-6 |
| 1 | 0.20 | 0.39 | 0.061 |
| | 0.53 | | 0.014 |

In Table 16, TNF-α and IL-6 were tested twice and each IC$_{50}$ was indicated.

Experiment 3 Effect on Increase in Blood Nitric Oxide level

When NO is produced in vivo as a result of a defense mechanism against infection or immune abnormality, it is readily metabolized to nitrous acid or nitric acid, resulting in an increase in blood nitric oxide concentration (NOx). Accordingly, an experimental animal was used to examine the effect of test compounds on the increase in the blood NOx level.

Female BALB/c mice (6 weeks old) were purchased and acclimatized for 1 week and assigned to the groups in each of which 6 to 8 animals were included. In a treatment group, 30 mg/kg of a test compound suspended in a 0.5% aqueous solution of methyl cellulose was given orally. In a control group, the vehicle was given similarly. After 1 hour, LPS (10 mg/kg) was given intraperitoneally to each animal in the treatment and control groups, and the blood was taken 6 hours after the LPS administration and examined for the serum concentration of nitrite ion+nitrate ion. The nitrate ion was converted into the nitrite ion using a nitrate reductase, and the measured values, which was obtained by the fluorescent method using DAN described above, were represented as the total nitrite ion concentration. A % inhibition in a treatment group when compared with the control group is shown in Table 17.

TABLE 17

| Compound No. | NO$_x$ inhibition (%) in blood |
|---|---|
| 1 | 76 |
| 3 | 90 |

TABLE 17-continued

| Compound No. | NO$_x$ inhibition (%) in blood |
|---|---|

Experiment 4 Effect on Increase in Blood Cytokine Level

As a result of a defense mechanism against an infection or an immune abnormality, various in vivo cytokines are produced. Accordingly, an experimental animal model was used to examine the effect of a test compound on the increase in the blood cytokine level.

Female BALB/c mice (6 weeks old) were purchased and acclimatized for 1 week and assigned to the groups in each of which 6 to 8 animals were included. In a treatment group, 30 mg/kg of a test compound suspended in a 0.5% aqueous solution of methyl cellulose was given orally. In a control group, the vehicle was given similarly. After 1 hour, LPS (10 mg/kg) was given intraperitoneally to each animal in the treatment and control groups, and the blood was taken 1 hour after the LPS administration and examined for the serum concentrations of TNF-α. IL-1α, IL-1β and IL-6 concentrations were determined using the serum from the blood taken 6 hours after the LPS administration. A % inhibition in a treatment group when compared with the control group is shown in Table 18. Each cytokine was determined using an assay kit manufactured by Amersham.

TABLE 18

| Compound No. | cytokine inhibition (%) in blood | | | |
|---|---|---|---|---|
| | TNF-α | IL-1α | IL-1β | IL-6 |
| 1 | 98 | 97 | 73 | 89 |

As evident from Table 18, Compound (I) has an excellent inhibitory effect on NO production, inhibitory effect on cytokine production, inhibitory effect on the increase of nitric oxide concentration in blood and inhibitory effect on the increase of cytokine concentration.

The composition and the system of the present invention contain an anionic synthetic phospholipid and a naturally-occurring phospholipid in specific proportions and have a pH adjusted to not more than about 6. Therefore, the inventive Compound, which is a main ingredient, a salt thereof and a prodrug therefor, and the composition and the system of the present invention have superior stability, even after sterilization in an autoclave etc.

Moreover, the composition and the system of the present invention can increase the concentration of the inventive Compound, a salt thereof and a prodrug therefor, and by controlling the particle size of the disperse phase particles, retentivity in blood, blood vessel permeability and migration into inflammatory sites can be enhanced. As a result, pharmacokinetics and biodistribution of the inventive Compound, a salt thereof and a prodrug therefor can be improved and targeting becomes possible, which in turn makes effective administration of the drug with suppressed side effect attainable. Therefore, the composition and the system of the present invention are useful for the treatment of the target disease particularly by intravenous administration.

The invention claimed is:

1. An emulsion composition comprising
   (1) a compound of the formula:

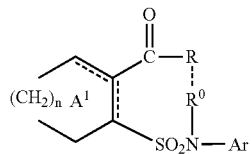

(I)

wherein R represents
   an optionally substituted aliphatic hydrocarbon group,
   an optionally substituted aromatic hydrocarbon group,
   an optionally substituted heterocyclic group,
   a group represented by the formula: OR$^1$
      wherein R$^1$ represents a hydrogen atom or an optionally substituted aliphatic hydrocarbon group,
   or a group represented by the formula:

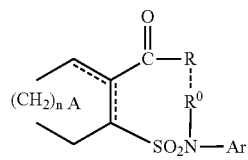

(Iaa)

wherein R$^{1b}$ and R$^{1c}$ are each independently
   a hydrogen atom or an optionally substituted aliphatic hydrocarbon group,
R$^0$ represents a hydrogen atom or an optionally substituted aliphatic hydrocarbon group,
or taken together, R and R$^0$ represent a bond,

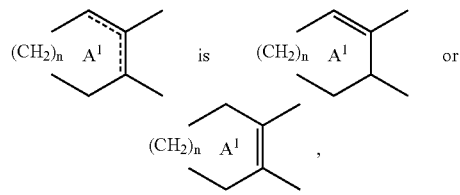

wherein n is an integer of 1 to 4,
ring A$^1$ is a cycloalkene optionally substituted by 1 to 4 substituents selected from the group consisting of
   (i) an aliphatic hydrocarbon group optionally having substituents,
   (ii) an aromatic hydrocarbon group optionally having substituents,
   (iii) a group represented by the formula: OR$^1$
      wherein R$^1$ represents a hydrogen atom or an aliphatic hydrocarbon group optionally having substituents, and
   (iv) a halogen atom,
Ar represents an optionally substituted aromatic hydrocarbon group,
a salt thereof or a prodrug therefor,
(2) an anionic synthetic phospholipid in a proportion of about 0.1 to about 0.2% weight per total volume relative to the composition in total, and
(3) a naturally-occurring phospholipid in a proportion of about 0.1 to about 10% weight per total volume relative to the composition in total,
wherein the emulsion has a pH of not more than about 6.

2. The composition of claim 1 wherein R, $R^1$, $R^{1b}$, $R^{1c}$, $R^0$, $A^1$ and Ar may be substituted with one to four substituents, each substituent independently selected from the group Q consisting of (i) a 5- to 8-membered ring or condensed ring substituent group containing 1 to 4 hetero atoms selected from the group consisting of nitrogen atom which is optionally oxidized, oxygen atom and sulfur atom, wherein said ring is optionally substituted by 1 to 3 substituents selected from the group consisting of $C_{1-4}$ alkyl, hydroxy, oxo and $C_{1-4}$ alkoxy, (ii) oxo substituent group,
(iii) hydroxyl substituent group,
(iv) $C_{1-6}$ alkoxy substituent group,
(v) $C_{3-10}$ cycloalkyloxy substituent group,
(vi) $C_{6-10}$ aryloxy substituent group,
(vii) $C_{7-19}$ aralkyloxy substituent group,
(viii) a 5- to 8-membered ring or condensed ring-oxy substituent group containing 1 to 4 hetero atoms selected from the group consisting of nitrogen atom which is optionally oxidized, oxygen atom and sulfur atom, wherein said ring-oxy substituent group is optionally substituted by 1 to 3 substituents selected from the group consisting of $C_{1-4}$ alkyl, hydroxy, oxo and $C_{1-4}$ alkoxy, (ix) $C_{1-6}$ alkylthio substituent group wherein the sulfur atom may be optionally oxidized,
(x) $C_{3-10}$ cycloalkylthio substituent group wherein the sulfur atom may be optionally oxidized,
(xi) $C_{6-10}$ arylthio substituent group wherein the sulfur atom may be optionally oxidized,
(xii) $C_{7-19}$ aralkylthio substituent group wherein the sulfur atom may be optionally oxidized,
(xiii) a 5- to 8-membered ring or condensed ring-thio substituent group containing 1 to 4 hetero atoms selected from the group consisting of nitrogen atom which is optionally oxidized, oxygen atom and sulfur atom, wherein said ring-thio substituent group is optionally substituted by 1 to 3 substituents selected from the group consisting of $C_{1-4}$ alkyl, hydroxy, oxo and $C_{1-4}$ alkoxy, (xiv) a 5- to 8-membered ring or condensed ring-sulfinyl substituent group containing 1 to 4 hetero atoms selected from the group consisting of nitrogen atom which is optionally oxidized, oxygen atom and sulfur atom, wherein said ring-sulfinyl substituent group is optionally substituted by 1 to 3 substituents selected from the group consisting of $C_{1-4}$ alkyl, hydroxy, oxo and $C_{1-4}$ alkoxy, (xv) a 5- to 8-membered ring group or a condensed ring-sulfonyl group containing 1 to 4 hetero atoms selected from the group consisting of nitrogen atom which is optionally oxidized, oxygen atom and sulfur atom, wherein said ring-sulfonyl substituent group is optionally substituted by 1 to 3 substituents selected from the group consisting of $C_{1-4}$ alkyl, hydroxy, oxo and $C_{1-4}$ alkoxy, (xvi) nitro substituent group,
(xvii) halogen atom,
(xviii) cyano substituent group,
(xix) carboxyl substituent group,
(xx) $C_{1-10}$ alkoxy-carbonyl substituent group,
(xxi) $C_{3-6}$ cycloalkyloxy-carbonyl substituent group,
(xxii) $C_{6-10}$ aryloxy-carbonyl substituent group,
(xxiii) $C_{7-19}$ aralkyloxy-carbonyl substituent group,
(xxiv) a 5- to 8-membered ring or condensed ring-oxycarbonyl substituent group containing 1 to 4 hetero atoms selected from the group consisting of nitrogen atom which is optionally oxidized, oxygen atom and sulfur atom, wherein said ring-oxycarbonyl substituent group is optionally substituted by 1 to 3 substituents selected from the group consisting of $C_{1-4}$ alkyl, hydroxy, oxo and $C_{1-4}$ alkoxy, (xxv) $C_{6-10}$ arylcarbonyl substituent group,
(xxvi) $C_{1-6}$ alkanoyl substituent group,
(xxvii) $C_{3-5}$ alkenoyl substituent group,
(xxviii) $C_{6-10}$ aryl-carbonyloxy substituent group,
(xxix) $C_{2-6}$ alkanoyloxy substituent group,
(xxx) $C_{3-5}$ alkenoyloxy substituent group,
(xxxi) carbamoyl substituent group or cyclic aminocarbonyl substituent group optionally substituted by 1 or 2 substituents selected from the group consisting of $C_{1-4}$ alkyl, phenyl, $C_{1-7}$ acyl and $C_{1-4}$ alkoxy-phenyl,
(xxxii) thiocarbamoyl substituent group optionally substituted by 1 or 2 substituents selected from the group consisting of $C_{1-4}$ alkyl and phenyl,
(xxxiii) carbamoyloxy substituent group optionally substituted by 1 or 2 substituents selected from the group consisting of $C_{1-4}$ alkyl and phenyl,
(xxxiv) $C_{1-6}$ alkanoylamino substituent group,
(xxxv) $C_{6-10}$ aryl-carbonylamino substituent group,
(xxxvi) $C_{1-10}$ alkoxy-carboxamide substituent group,
(xxxvii) $C_{6-10}$ aryloxy-carboxamide substituent group,
(xxxviii) $C_{7-19}$ aralkyloxy-carboxamide substituent group,
(xxxix) $C_{1-10}$ alkoxy-carbonyloxy substituent group,
(xl) $C_{6-10}$ aryloxy-carbonyloxy substituent group,
(xli) $C_{7-19}$ aralkyloxy-carbonyloxy substituent group,
(xlii) $C_{3-10}$ cycloalkyloxy-carbonyloxy substituent group,
(xliii) ureido substituent group optionally substituted by 1 to 3 substituents selected from the group consisting of $C_{1-4}$ alkyl and phenyl, and
(xliv) $C_{6-10}$ aryl substituent group optionally having 1 to 4 substituents selected from the group consisting of $C_{1-4}$ alkyl and phenyl.

3. The composition of claim 1, wherein R is
(1) ① linear or branched $C_{1-20}$ alkyl, ② $C_{3-10}$ cycloalkyl, ③ $C_{4-12}$ cycloalkylalkyl, ④ lower ($C_{3-6}$) alkenyl group or ⑤ lower ($C_{3-6}$) alkynyl group optionally having 1 to 4 substituents each independently selected from the group Q;
wherein when two substituents from group Q substitute said linear or branched $C_{1-20}$ alkyl, $C_{3-10}$ cycloalkyl, $C_{4-12}$ cycloalkylalkyl, $C_{3-6}$ alkenyl or $C_{3-6}$ alkynyl, said substituents may be linked to form a ring;
(2) $C_{6-14}$ aromatic hydrocarbon group optionally having 1 to 5 substituents selected from the group consisting of halogen atom, $C_{1-4}$ alkyl group, $C_{1-4}$ alkoxy group, $C_{1-4}$ alkoxy-carbonyl group, carboxyl group, nitro group, cyano group, hydroxyl group, $C_{1-4}$ alkanoylamino group, $C_{3-16}$ cycloalkyl group, $C_{6-10}$ aryl group, halogeno $C_{1-4}$ alkyl group, halogeno $C_{1-4}$ alkoxy group, $C_{1-4}$ alkylthio group, $C_{1-4}$ alkylsulfonyl group, $C_{1-4}$ alkanoyl group, 5-membered aromatic heterocyclic group, carbamoyl group, $C_{1-4}$ alkyl-carbamoyl group, $C_{1-4}$ alkoxy-carbonyl-$C_{1-4}$ alkyl-carbamoyl group and 1,3-diacylguanidino-$C_{1-4}$ alkyl group,
(3) a 5- to 8-membered ring or a condensed ring group containing 1 to 4 hetero atoms selected from the group consisting of nitrogen atom which is optionally oxidized, oxygen atom and sulfur atom, wherein said ring group optionally has 1 to 3 substituents selected from the group consisting of $C_{1-4}$ alkyl, hydroxy, oxo and $C_{1-4}$ alkoxy,
(4) a group of the formula —$OR^1$ wherein $R^1$ is
(i) hydrogen atom or (ii) ① linear or branched $C_{1-20}$ alkyl, ② $C_{3-10}$ cycloalkyl, ③ $C_{4-12}$ cycloalkylalkyl, ④ lower $C_{3-6}$ alkenyl group or ⑤ lower $C_{3-6}$ alkynyl group optionally having 1 to 4 substituents, each independently selected from the group Q;

wherein when two substituents from group Q substitute said linear or branched $C_{1-20}$ alkyl, $C_{3-10}$ cycloalkyl, $C_{4-12}$ cycloalkylalkyl, $C_{3-6}$ alkenyl or $C_{3-6}$ alkynyl, said substituents may be linked to form a ring; or (5) a group of the formula

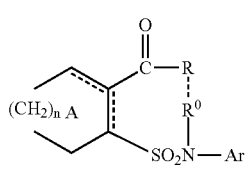

(Iaa)

wherein $R^{1b}$ and $R^{1c}$ are each independently a (i) hydrogen atom or (ii) ① linear or branched $C_{1-20}$ alkyl, ② $C_{3-10}$ cycloalkyl, ③ $C_{4-12}$ cycloalkylalkyl, ④ lower $C_{3-6}$ alkenyl group or ⑤ lower $C_{3-6}$ alkynyl group optionally substituted with 1 to 4 substituents each independently selected from the group Q;

wherein when two substituents from group Q substitute said linear or branched $C_{1-20}$ alkyl, $C_{3-10}$ cycloalkyl, $C_{4-12}$ cycloalkylalkyl, $C_{3-6}$ alkenyl or $C_{3-6}$ alkynyl, said substituents may be linked to form a ring;

$R^0$ represents a hydrogen atom, a linear or branched $C_{1-20}$ alkyl, a $C_{3-10}$ cycloalkyl, a $C_{4-12}$ cycloalkylalkyl, a lower ($C_{3-6}$) alkenyl group or a lower ($C_{3-6}$) alkynyl group, or R and $R^0$ represent a bond with each other, ring $A^1$ represents cycloalkene optionally substituted by 1 to 4 substituents, each independently selected from the group consisting of (1) linear or branched $C_{1-20}$ alkyl, $C_{3-10}$ cycloalkyl, $C_{4-12}$ cycloalkylalkyl, $C_{3-6}$ alkenyl or $C_{3-6}$ alkynyl;

optionally substituted with 1 to 4 substituents, each of said substituents independently selected from substituent group Q;

wherein when two substituents from group Q substitute said linear or branched $C_{1-20}$ alkyl, $C_{3-10}$ cycloalkyl, $C_{4-12}$ cycloalkylalkyl, $C_{3-6}$ alkenyl or $C_{3-6}$ alkynyl, said substituents may be linked to form a ring;

(2) a $C_{6-14}$ aromatic hydrocarbon group optionally having 1 to 5 substituents selected from the group consisting of halogen atom, $C_{1-4}$ alkyl group, $C_{1-4}$ alkoxy group, $C_{1-4}$ alkoxy-carbonyl group, carboxyl group, nitro group, cyano group, hydroxyl group, $C_{1-4}$ alkanoylamino group, $C_{3-6}$ cycloalkyl group, $C_{6-10}$ aryl group, halogeno $C_{1-4}$ alkyl group, halogeno $C_{1-4}$ alkoxy group, $C_{1-4}$ alkylthio group, $C_{1-4}$ alkylsulfonyl group, $C_{1-4}$ alkanoyl group, 5-membered aromatic heterocyclic group, carbamoyl group, $C_{1-4}$ alkyl-carbamoyl group, $C_{1-4}$ alkoxy-carbonyl-$C_{1-4}$ alkyl-carbamoyl group and 1,3-diacylguanidino-$C_{1-4}$ alkyl group;

(3) —$OR^1$ wherein $R^1$ is (i) hydrogen atom or (ii) ① linear or branched $C_{1-20}$ alkyl, ② $C_{3-10}$ cycloalkyl, ③ $C_{4-12}$ cycloalkylalkyl, ④ lower $C_{3-6}$ alkenyl group or ⑤ lower $C_{3-6}$ alkynyl group optionally having 1 to 4 substituents, each independently selected from the group Q;

wherein when two substituents from group Q substitute said linear or branched $C_{1-20}$ alkyl, $C_{3-10}$ cycloalkyl, $C_{4-12}$ cycloalkylalkyl, $C_{3-6}$ alkenyl or $C_{3-6}$ alkynyl, said substituents may be linked to form a ring;

(4) halogen atoms and,

Ar represents a $C_{6-14}$ aromatic hydrocarbon group optionally having 1 to 5 substituents selected from the group consisting of halogen atom, $C_{1-4}$ alkyl group, $C_{1-4}$ alkoxy group, $C_{1-4}$ alkoxycarbonyl group, carboxyl group, nitro group, cyano group, hydroxyl group, $C_{1-4}$ alkanoylamino group, $C_{3-6}$ cycloalkyl group, $C_{6-10}$ aryl group, halogeno $C_{1-4}$ alkyl group, halogeno $C_{1-4}$ alkoxy group, $C_{1-4}$ alkylthio group, $C_{1-4}$ alkylsulfonyl group, $C_{1-4}$ alkanoyl group, 5-membered aromatic heterocyclic group, carbamoyl group, $C_{1-4}$ alkyl-carbamoyl group, $C_{1-4}$ alkoxycarbonyl-$C_{1-4}$ alkyl-carbamoyl group and 1,3-diacylguanidino-$C_{1-4}$ alkyl group.

4. The composition of claim 1, wherein when two substituents from group Q substitute said linear or branched $C_{1-20}$ alkyl, $C_{3-10}$ cycloalkyl, $C_{4-12}$ cycloalkylalkyl, $C_{3-6}$ alkenyl or $C_{3-6}$ alkynyl, said substituents may be linked to form a ring;

wherein said ring is an indanyl group or a 1,2,3,4-tetrahydronaphthyl group;

and wherein said ring may be further substituted by 1 to 4 substituents each independently selected from group Q.

5. The composition of claim 1, wherein the compound is selected from the group consisting of d-ethyl 6-[N-(2-chloro-4-fluorophenyl)sulfamoyl]-1-cyclohexene-1-carboxylate, d-ethyl 6-[N-(2,4-difluorophenyl)sulfamoyl]-1-cyclohexene-1-carboxylate, ethyl 6-[N-(2-chlorophenyl)sulfamoyl]-1-cyclohexene-1-carboxylate and ethyl 6-[N-(2-chloro-4-methylphenyl)sulfamoyl]-1-cyclohexene-1-carboxylate, or a salt thereof.

6. The composition of claim 1, wherein said anionic synthetic phospholipid is a compound of the formula

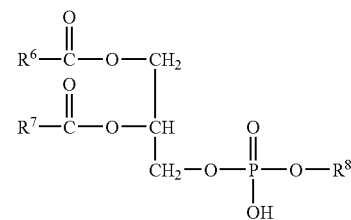

(II)

wherein $R^6$ and $R^7$ are the same or different and each is a $C_{7-20}$ chain hydrocarbon group, and $R^8$ is

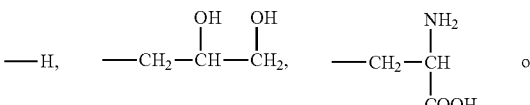

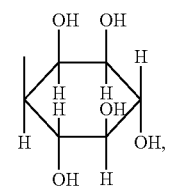

or a salt thereof.

7. The composition of claim 1, wherein said anionic synthetic phospholipid is a compound of the formula

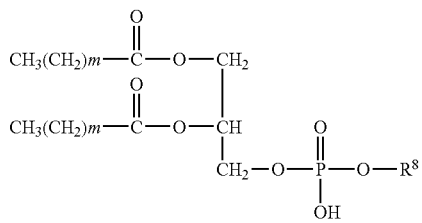

(III)

wherein m is an integer of 7-20, and $R^8$ is

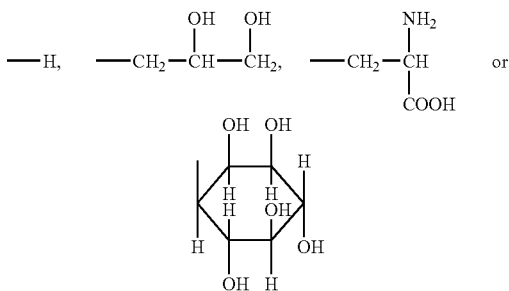

or a salt thereof.

8. The composition of claim 1, wherein said anionic synthetic phospholipid is selected from the group consisting of dimyristoylphosphatidylglycerol, dipalmitoylphosphatidylglycerol, distearoylphosphatidylglycerol, dioleoylphosphatidylglycerol, oleoylpalmitoylphosphatidylglycerol, dioctanoylphosphatidic acid, didecanoylphosphatidic acid, dilauroylphosphatidic acid, dimyristoylphosphatidic acid, dipalmitoylphosphatidic acid, diheptadecanoylphosphatidic acid, distearoylphosphatidic acid, dioleoylphosphatidic acid, arachidonylstearoylphosphatidic acid, dipalmitoylphosphatidylserine, dioleoylphosphatidylserine, dimyristoylphosphatidylinositol, dipalmitoylphosphatidylinositol, distearoylphosphatidylinositol, dioleoylphosphatidylinositol, dimyristoylphosphatidylserine and distearoylphosphatidylserine.

9. The composition of claim 1, wherein said anionic synthetic phospholipid is dimyristoylphosphatidylglycerol.

10. The composition of claim 1, wherein said naturally-occurring phospholipid is egg yolk lecithin or soybean lecithin.

11. The composition of claim 1, wherein said naturally-occurring phospholipid is egg yolk lecithin.

12. The composition of claim 1, wherein said anionic synthetic phospholipid is contained in a proportion of about 0.2% weight per total volume of the composition in total.

13. The composition of claim 1, wherein compound (I), a salt thereof or a prodrug therefor is in a proportion of about 0.001 to about 95 weight percent of the composition in total.

14. The composition of claim 1, wherein compound (I), a salt thereof or a prodrug therefor is in a proportion of about 0.01 to about 30 weight percent of the composition in total.

15. The composition of claim 1, which further comprises a component selected from the group consisting of oil, water and a combination thereof.

16. The composition of claim 15, wherein said oil is selected from the group consisting of vegetable oil, a partially hydrogenated vegetable oil, mono-acid glyceride, mixed acid glyceride and medium-size chain fatty acid glycerine ester.

17. The composition of claim 15, wherein said oil is a vegetable oil.

18. The composition of claim 17, wherein said vegetable oil is selected from the group consisting of soybean oil, cottonseed oil, rapeseed oil, peanut oil, safflower oil, sesame oil, rice bran oil, corn germ oil, sunflower oil, poppy oil and olive oil.

19. The composition of claim 17, wherein said vegetable oil is a soybean oil.

20. The composition of claim 15, wherein said oil is in a proportion of about 1 to about 30 weight percent of the composition in total.

21. The composition of claim 1, which further comprises glycerine.

22. The composition of claim 1, which is an oil-in-water composition.

23. The composition of claim 1, which has a pH from about 3 to about 6.

24. The composition of claim 1, which is for an injection.

25. A composition comprising:
0.1 to 3% weight per total volume of d-ethyl 6-[N-(2-chloro-4-fluorophenyl)sulfamoyl]-1-cyclohexene-1-carboxylate,
5 to 25% weight per total volume of soybean oil,
1 to 3% weight per total volume of egg yolk lecithin,
0.1 to 0.2% weight per total volume dimyristoyl phosphatidylglycerol and water, wherein the composition has a pH of not more than about 6.

26. A composition comprising:
0.1 to 3% weight per total volume of d-ethyl 6-[N-(2-chloro-4-fluorophenyl)sulfamoyl]-1-cyclohexene-1-carboxylate,
5 to 25% weight per total volume of soybean oil,
1 to 3% weight per total volume of egg yolk lecithin,
0.1 to 0.2% weight per total volume distearoyl phosphatidylglycerol and water, wherein the composition has a pH of not more than about 6.

27. A composition comprising:
1% weight per total volume of d-ethyl 6-[N-(2-chloro-4-fluorophenyl)sulfamoyl]-1-cyclohexene-1-carboxylate,
20% weight per total volume of soybean oil,
1.2% weight per total volume of egg yolk lecithin,
0.2% weight per total volume dimyristoyl phosphatidylglycerol and water, wherein the composition has a pH of not more than about 6.

28. A composition comprising:
1% weight per total volume of d-ethyl 6-[N-(2-chloro-4-fluorophenyl)sulfamoyl]-1-cyclohexene-1-carboxylate,
20% weight per total volume of soybean oil,
1.2% weight per total volume of egg yolk lecithin,
0.2% weight per total volume distearoyl phosphatidylglycerol and water, wherein the composition has a pH of not more than about 6.

29. The composition of claim 1, which comprises a disperse phase particle comprising anionic synthetic phospholipid, naturally-occurring phospholipid, an oil component and compound (I), a salt thereof or a prodrug therefor, and water wherein the disperse phase particle is dispersed.

30. The composition of claim 29, wherein the disperse phase has an average particle size of about 25 to about 500 nm.

31. The composition of claim 1, which is a nitric oxide or cytokine production inhibitor, or a nitric oxide inhibitor and a cytokine production inhibitor.

32. The composition of claim 1, which is an agent for treating cardiac disease, autoimmune disease, sepsis or septic shock.

33. A method for making an emulsion comprising the steps of:
(a) adding an anionic synthetic phospholipid in a proportion of about 0.1 to about 0.2% weight per total volume relative to the composition in total, and a naturally-occurring phospholipid to a compound represented by the formula:

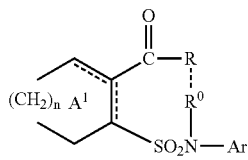
(I)

wherein R represents
an optionally substituted aliphatic hydrocarbon group,
an optionally substituted, aromatic hydrocarbon group,
an optionally substituted heterocyclic group,
a group represented by the formula: $OR^1$
wherein $R^1$ represents a hydrogen atom or an optionally substituted aliphatic hydrocarbon group,
or a group represented by the formula:

wherein $R^{1b}$ and $R^{1c}$ are each independently a hydrogen atom or an optionally substituted aliphatic hydrocarbon group,
$R^0$ represents a hydrogen atom or an optionally substituted aliphatic hydrocarbon group,
or taken together, R and $R^0$ represent a bond,

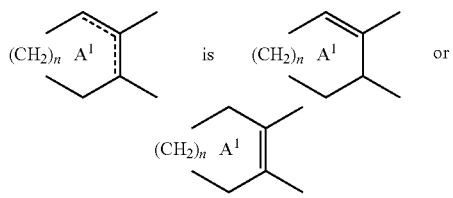

wherein n is an integer of 1 to 4,
ring $A^1$ is a cycloalkene optionally substituted by 1 to 4 substituents selected from the group consisting of
(i) an aliphatic hydrocarbon group optionally having substituents,
(ii) an aromatic hydrocarbon group optionally having substituents,
(iii) a group represented by the formula: $OR^1$
where $R^1$ represents a hydrogen atom or an aliphatic hydrocarbon group optionally having substituents, and
(iv) a halogen atom,
Ar represents an optionally substituted aromatic hydrocarbon group,
a salt thereof or a prodrug therefor, in oil and water to form an emulsion; and then,
(b) adjusting said emulsion to a pH of not more than 6 to form a stable emulsion.

34. The method of claim 33, whereby stability of said stable emulsion during autoclave sterilization is improved.

35. A method for treating cardiac disease, autoimmune disease, sepsis or septic shock, comprising administrating to a mammal in need thereof a pharmaceutically effective amount of the composition of claim 1.

36. A method of making a composition of claim 1 for manufacturing an agent for preventing or treating cardiac disease, autoimmune disease, sepsis or septic shock comprising introducing said compound of formula (I), said anionic synthetic phospholipid, and said naturally-occurring phospholipid under conditions sufficient to make an emulsion composition of claim 1.

* * * * *

UNITED STATES PATENT AND TRADEMARK OFFICE
CERTIFICATE OF CORRECTION

| | | |
|---|---|---|
| PATENT NO. | : 7,960,416 B2 | Page 1 of 1 |
| APPLICATION NO. | : 10/485637 | |
| DATED | : June 14, 2011 | |
| INVENTOR(S) | : Jun Sato et al. | |

It is certified that error appears in the above-identified patent and that said Letters Patent is hereby corrected as shown below:

Col. 122, claim 1, lines 20-25, replace the formula with the following:

Col. 125, claim 3, lines 15-20, replace the formula with the following:

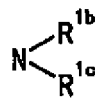

Signed and Sealed this
Twenty-ninth Day of November, 2011

David J. Kappos
*Director of the United States Patent and Trademark Office*